United States Patent
Li et al.

(10) Patent No.: US 11,512,132 B2
(45) Date of Patent: *Nov. 29, 2022

(54) ANTI-PD-L1 ANTIBODIES AND THEIR USE AS THERAPEUTICS AND DIAGNOSTICS

(71) Applicant: BEIGENE, LTD., Grand Cayman (KY)

(72) Inventors: Kang Li, Beijing (CN); Jing Song, Beijing (CN); Tong Zhang, Beijing (CN); Yucheng Li, Beijing (CN); Zhiying Ren, Beijing (CN); Yanshen Kang, Beijing (CN)

(73) Assignee: BEIGENE, LTD., Grand Cayman (KY)

(*) Notice: Subject to any disclaimer, the term of this patent is extended or adjusted under 35 U.S.C. 154(b) by 433 days.

This patent is subject to a terminal disclaimer.

(21) Appl. No.: 16/704,738

(22) Filed: Dec. 5, 2019

(65) Prior Publication Data

US 2020/0283527 A1  Sep. 10, 2020

Related U.S. Application Data

(63) Continuation of application No. 15/323,153, filed as application No. PCT/CN2015/083066 on Jul. 1, 2015, now Pat. No. 10,544,225.

(30) Foreign Application Priority Data

Jul. 3, 2014 (WO) ............. PCT/CN2014/081581

(51) Int. Cl.
*A61K 39/00* (2006.01)
*C07K 16/28* (2006.01)
*A61P 35/00* (2006.01)

(52) U.S. Cl.
CPC ......... *C07K 16/2827* (2013.01); *A61P 35/00* (2018.01); *C07K 16/2818* (2013.01); *A61K 2039/505* (2013.01); *C07K 2317/24* (2013.01); *C07K 2317/34* (2013.01); *C07K 2317/76* (2013.01); *C07K 2317/92* (2013.01); *C07K 2319/30* (2013.01)

(58) Field of Classification Search
CPC ............ C07K 16/2827; C07K 16/2818; C07K 2317/24; A61P 35/00; A61K 2039/505
See application file for complete search history.

(56) References Cited

U.S. PATENT DOCUMENTS

| | | | |
|---|---|---|---|
| 5,624,821 A | 4/1997 | Winter et al. |
| 5,629,204 A | 5/1997 | Honjo et al. |
| 5,648,260 A | 7/1997 | Winter et al. |
| 5,698,520 A | 12/1997 | Honjo et al. |
| 5,994,514 A | 11/1999 | Jardieu et al. |
| 6,165,745 A | 12/2000 | Ward et al. |
| 6,194,551 B1 | 2/2001 | Idusogie et al. |
| 6,528,624 B1 | 3/2003 | Idusogie et al. |
| 6,632,927 B2 | 10/2003 | Adair et al. |
| 6,737,056 B1 | 5/2004 | Presta |
| 6,808,710 B1 | 10/2004 | Wood et al. |
| 6,936,704 B1 | 8/2005 | Freeman et al. |
| 7,029,674 B2 | 4/2006 | Carreno et al. |
| 7,038,013 B2 | 5/2006 | Freeman et al. |
| 7,101,550 B2 | 9/2006 | Wood et al. |
| 7,122,637 B2 | 10/2006 | Presta |
| 7,297,775 B2 | 11/2007 | Idusogie et al. |
| 7,317,091 B2 | 1/2008 | Lazar et al. |
| 7,332,581 B2 | 2/2008 | Presta |
| 7,335,742 B2 | 2/2008 | Presta |
| 7,355,008 B2 | 4/2008 | Stavenhagen et al. |
| 7,364,731 B2 | 4/2008 | Idusogie et al. |
| 7,371,826 B2 | 5/2008 | Presta |
| 7,393,848 B2 | 7/2008 | Currie et al. |
| 7,414,171 B2 | 8/2008 | Honjo et al. |
| 7,416,726 B2 | 8/2008 | Ravetch |
| 7,488,802 B2 | 2/2009 | Collins et al. |
| 7,514,444 B2 | 4/2009 | Honigberg et al. |
| 7,563,869 B2 | 7/2009 | Honjo et al. |
| 7,595,048 B2 | 9/2009 | Honjo et al. |
| 7,597,889 B1 | 10/2009 | Armour et al. |
| 7,608,429 B2 | 10/2009 | Reilly et al. |
| 7,635,757 B2 | 12/2009 | Freeman et al. |
| 7,638,492 B2 | 12/2009 | Wood et al. |
| 7,655,783 B2 | 2/2010 | Reilly et al. |
| 7,670,600 B2 | 3/2010 | Dall'Acqua et al. |
| 7,718,662 B1 | 5/2010 | Chen et al. |
| 7,741,072 B2 | 6/2010 | Idusogie et al. |
| 7,790,858 B2 | 9/2010 | Presta |

(Continued)

FOREIGN PATENT DOCUMENTS

| | | |
|---|---|---|
| CN | 1753912 A | 3/2006 |
| CN | 1771231 A | 5/2006 |

(Continued)

OTHER PUBLICATIONS

International Search Report and Written Opinion for International Application No. PCT/CN2013/083467, dated Jun. 16, 2014, 9 pages.
Supplementary Partial European Search Report for European Application No. 13893636.4, dated Feb. 28, 2017, 13 pages.
Extended European Search Report for European Application No. 15815646.3, dated Dec. 21, 2017, 10 pages.
International Search Report and Written Opinion for International Application No. PCT/CN2015/083066, dated Sep. 24, 2015, 8 pages.
European Search Report for European Application No. 16167542.6, dated Nov. 14, 2016, 5 pages.

(Continued)

*Primary Examiner* — Sheela J. Huff
(74) *Attorney, Agent, or Firm* — Cooley LLP

(57) ABSTRACT

Provided are antibodies that specifically bind to Programmed Death-1 (PD1, Pdcd-1, or CD279) ligand (PD-L1) and inhibit PD-L1-mediated cellular signaling and activities in immune cells, antibodies binding to a set of amino acid residues required for its ligand binding, and uses of these antibodies to treat or diagnose cancer, infectious diseases or other pathological disorders modulated by PD-L1-mediated functions.

14 Claims, 9 Drawing Sheets

Specification includes a Sequence Listing.

(56) References Cited

U.S. PATENT DOCUMENTS

| | | | |
|---|---|---|---|
| 7,851,598 | B2 | 12/2010 | Davis |
| 7,863,419 | B2 | 1/2011 | Taylor et al. |
| 7,943,743 | B2 | 5/2011 | Korman et al. |
| 7,998,479 | B2 | 8/2011 | Honjo et al. |
| 8,008,449 | B2 | 8/2011 | Korman et al. |
| 8,084,620 | B2 | 12/2011 | Liu et al. |
| 8,088,905 | B2 | 1/2012 | Collins et al. |
| 8,168,179 | B2 | 5/2012 | Honjo et al. |
| 8,168,757 | B2 | 5/2012 | Finnefrock et al. |
| 8,217,149 | B2 | 7/2012 | Irving et al. |
| 8,246,955 | B2 | 8/2012 | Honjo et al. |
| 8,354,509 | B2 | 1/2013 | Carven et al. |
| 8,552,154 | B2 | 10/2013 | Freeman et al. |
| 8,617,546 | B2 | 12/2013 | Kang et al. |
| 8,728,474 | B2 | 5/2014 | Honjo et al. |
| 8,735,553 | B1 | 5/2014 | Li et al. |
| 8,779,105 | B2 | 7/2014 | Korman et al. |
| 8,911,726 | B2 | 12/2014 | Takahashi et al. |
| 8,945,561 | B2 | 2/2015 | Davis |
| 9,067,999 | B1 | 6/2015 | Honjo et al. |
| 9,073,994 | B2 | 7/2015 | Honjo et al. |
| 9,084,776 | B2 | 7/2015 | Korman et al. |
| 9,139,653 | B1 | 9/2015 | Campbell et al. |
| 9,175,082 | B2 | 11/2015 | Zhou et al. |
| 9,217,034 | B2 | 12/2015 | Li et al. |
| 9,447,106 | B2 | 9/2016 | Wang et al. |
| 9,492,540 | B2 | 11/2016 | Korman et al. |
| 9,556,188 | B2 | 1/2017 | Wang et al. |
| 9,624,298 | B2 | 4/2017 | Nastri et al. |
| 9,834,606 | B2 | 12/2017 | Li et al. |
| 9,920,123 | B2 | 3/2018 | Irving et al. |
| 9,988,450 | B2 | 6/2018 | Li et al. |
| 10,005,782 | B2 | 6/2018 | Wang et al. |
| 10,058,609 | B2 | 8/2018 | Zhou et al. |
| 10,487,147 | B2 | 11/2019 | Nastri et al. |
| 10,519,235 | B2 | 12/2019 | Li et al. |
| 10,544,225 | B2 | 1/2020 | Li et al. |
| 10,550,185 | B2 | 2/2020 | Bernett et al. |
| 10,570,139 | B2 | 2/2020 | Wang et al. |
| 10,793,632 | B2 | 10/2020 | Bernett et al. |
| 10,858,435 | B2 | 12/2020 | Finlay |
| 10,864,203 | B2 | 12/2020 | Song et al. |
| 10,927,117 | B2 | 2/2021 | Wang et al. |
| 11,142,528 | B2 | 10/2021 | Wang et al. |
| 11,186,637 | B2 | 11/2021 | Li et al. |
| 11,202,782 | B2 | 12/2021 | Wang et al. |
| 11,203,637 | B2 | 12/2021 | Zhang et al. |
| 11,377,449 | B2 | 7/2022 | Wang et al. |
| 2002/0094989 | A1 | 7/2002 | Hale et al. |
| 2004/0038339 | A1 | 2/2004 | Kufer et al. |
| 2005/0064514 | A1 | 3/2005 | Stavenhagen et al. |
| 2005/0202028 | A1 | 9/2005 | Ledbetter et al. |
| 2006/0121032 | A1 | 6/2006 | Dahiyat et al. |
| 2006/0134105 | A1 | 6/2006 | Lazar et al. |
| 2006/0178367 | A1 | 8/2006 | Currie et al. |
| 2006/0183746 | A1 | 8/2006 | Currie et al. |
| 2006/0263856 | A1 | 11/2006 | Gillies et al. |
| 2007/0160597 | A1 | 7/2007 | Lazar et al. |
| 2008/0076921 | A1 | 3/2008 | Honigberg et al. |
| 2008/0139582 | A1 | 6/2008 | Honigberg et al. |
| 2009/0068175 | A1 | 3/2009 | Lazar et al. |
| 2009/0105209 | A1 | 4/2009 | Dewdney et al. |
| 2009/0155256 | A1 | 6/2009 | Black et al. |
| 2009/0217401 | A1 | 8/2009 | Korman et al. |
| 2009/0318441 | A1 | 12/2009 | Brain et al. |
| 2010/0004231 | A1 | 1/2010 | Dewdney et al. |
| 2010/0016296 | A1 | 1/2010 | Singh et al. |
| 2010/0016301 | A1 | 1/2010 | Dewdney et al. |
| 2010/0029610 | A1 | 2/2010 | Singh et al. |
| 2010/0035841 | A1 | 2/2010 | Jankowski et al. |
| 2010/0087464 | A1 | 4/2010 | Mi et al. |
| 2010/0105676 | A1 | 4/2010 | Liu et al. |
| 2010/0144705 | A1 | 6/2010 | Miller |
| 2010/0151492 | A1 | 6/2010 | Ahmed et al. |
| 2010/0160292 | A1 | 6/2010 | Whitney et al. |
| 2010/0160303 | A1 | 6/2010 | Liu et al. |
| 2010/0197924 | A1 | 8/2010 | Gould et al. |
| 2010/0222325 | A1 | 9/2010 | Berthel et al. |
| 2010/0249092 | A1 | 9/2010 | Singh et al. |
| 2010/0254905 | A1 | 10/2010 | Honigberg et al. |
| 2010/0317834 | A1 | 12/2010 | Lazar et al. |
| 2011/0008369 | A1 | 1/2011 | Finnefrock et al. |
| 2011/0052584 | A1 | 3/2011 | Ravetch |
| 2011/0054151 | A1 | 3/2011 | Lazar et al. |
| 2011/0118233 | A1 | 5/2011 | Blomgren et al. |
| 2011/0124640 | A1 | 5/2011 | Liu et al. |
| 2011/0159023 | A1 | 6/2011 | Langermann |
| 2011/0171215 | A1 | 7/2011 | Davis et al. |
| 2011/0171220 | A1 | 7/2011 | Davis et al. |
| 2011/0177088 | A1 | 7/2011 | Olive et al. |
| 2011/0195068 | A1 | 8/2011 | Langermann et al. |
| 2011/0224235 | A1 | 9/2011 | Honigberg et al. |
| 2011/0271358 | A1 | 11/2011 | Freeman et al. |
| 2011/0287032 | A1 | 11/2011 | Lazar et al. |
| 2011/0301145 | A1 | 12/2011 | Barbosa, Jr. et al. |
| 2012/0028981 | A1 | 2/2012 | Miller |
| 2012/0040961 | A1 | 2/2012 | Gray et al. |
| 2012/0053189 | A1 | 3/2012 | Loury |
| 2012/0058996 | A1 | 3/2012 | Liu et al. |
| 2012/0076726 | A1 | 3/2012 | Gellerfors et al. |
| 2012/0077832 | A1 | 3/2012 | Witowski et al. |
| 2012/0082702 | A1 | 4/2012 | DeLucca et al. |
| 2012/0129852 | A1 | 5/2012 | Duan et al. |
| 2012/0157442 | A1 | 6/2012 | Bui et al. |
| 2012/0157443 | A1 | 6/2012 | Bui et al. |
| 2012/0232054 | A1 | 9/2012 | Moriarty et al. |
| 2012/0237522 | A1 | 9/2012 | Kang et al. |
| 2012/0251531 | A1 | 10/2012 | Baehner et al. |
| 2013/0004514 | A1 | 1/2013 | Zahn et al. |
| 2013/0079327 | A1 | 3/2013 | Yamamoto et al. |
| 2013/0089541 | A1 | 4/2013 | D'Angelo et al. |
| 2013/0096118 | A1 | 4/2013 | Liu et al. |
| 2013/0116213 | A1 | 5/2013 | Cha et al. |
| 2013/0259868 | A1 | 10/2013 | Roschke et al. |
| 2013/0261103 | A1 | 10/2013 | Currie et al. |
| 2013/0281432 | A1 | 10/2013 | Currie et al. |
| 2013/0309250 | A1 | 11/2013 | Cogswell et al. |
| 2014/0044738 | A1 | 2/2014 | Langermann et al. |
| 2014/0045833 | A1 | 2/2014 | Laurent et al. |
| 2014/0094459 | A1 | 4/2014 | Goldstein et al. |
| 2014/0107151 | A1 | 4/2014 | Goldstein et al. |
| 2014/0162316 | A1 | 6/2014 | O'Neil et al. |
| 2014/0162983 | A1 | 6/2014 | Hodous et al. |
| 2014/0221398 | A1 | 8/2014 | Goldstein et al. |
| 2014/0243306 | A1 | 8/2014 | Heng et al. |
| 2014/0243504 | A1 | 8/2014 | Davis et al. |
| 2014/0245468 | A1 | 8/2014 | McWhirter et al. |
| 2014/0271642 | A1 | 9/2014 | Murphy et al. |
| 2014/0314714 | A1 | 10/2014 | Honjo et al. |
| 2014/0341902 | A1 | 11/2014 | Maecker et al. |
| 2014/0356363 | A1 | 12/2014 | Zhou et al. |
| 2014/0377269 | A1 | 12/2014 | Mabry et al. |
| 2015/0044231 | A1 | 2/2015 | Kjaergaard et al. |
| 2015/0079109 | A1 | 3/2015 | Li et al. |
| 2015/0118222 | A1 | 4/2015 | Levy et al. |
| 2015/0125444 | A1 | 5/2015 | Tsui et al. |
| 2015/0210763 | A1 | 7/2015 | Kuramochi et al. |
| 2015/0259354 | A1 | 9/2015 | Wang et al. |
| 2015/0315274 | A1 | 11/2015 | Li et al. |
| 2015/0337053 | A1 | 11/2015 | McCarthy et al. |
| 2015/0353631 | A1 | 12/2015 | Buttini et al. |
| 2016/0083392 | A1 | 3/2016 | Wang et al. |
| 2017/0044260 | A1 | 2/2017 | Baruah et al. |
| 2017/0073349 | A1 | 3/2017 | Wang et al. |
| 2018/0037655 | A1 | 2/2018 | Hegde et al. |
| 2018/0215825 | A1 | 8/2018 | Li et al. |
| 2018/0251466 | A1 | 9/2018 | Wang et al. |
| 2018/0251551 | A1 | 9/2018 | Li et al. |
| 2019/0169201 | A1 | 6/2019 | Wang et al. |
| 2020/0030339 | A1 | 1/2020 | Wang et al. |
| 2020/0069666 | A1 | 3/2020 | Song et al. |
| 2020/0148690 | A1 | 5/2020 | Wang et al. |
| 2020/0181150 | A1 | 6/2020 | Wang et al. |
| 2020/0216535 | A1 | 7/2020 | Li et al. |

(56) References Cited

U.S. PATENT DOCUMENTS

| | | |
|---|---|---|
| 2020/0368237 A1 | 11/2020 | Hilger et al. |
| 2021/0040213 A1 | 2/2021 | Song et al. |
| 2021/0130363 A1 | 5/2021 | Wang et al. |
| 2021/0147543 A1 | 5/2021 | Wang et al. |
| 2021/0228553 A1 | 7/2021 | Song et al. |
| 2021/0230274 A1 | 7/2021 | Li et al. |
| 2021/0275530 A1 | 9/2021 | Hu et al. |
| 2021/0332049 A1 | 10/2021 | Guo et al. |
| 2022/0119524 A1 | 4/2022 | Li et al. |

FOREIGN PATENT DOCUMENTS

| | | |
|---|---|---|
| CN | 101104640 | 1/2008 |
| CN | 101213297 A | 7/2008 |
| CN | 101355965 A | 1/2009 |
| CN | 101899114 | 12/2010 |
| CN | 102245640 A | 11/2011 |
| CN | 102264762 A | 11/2011 |
| CN | 102656173 A | 9/2012 |
| CN | 104884458 A | 9/2015 |
| CN | 105531288 A | 4/2016 |
| CN | 106103485 A | 11/2016 |
| CN | 107011441 A | 8/2017 |
| CN | 107090041 A | 8/2017 |
| GB | 1412017 A | 10/1975 |
| JP | H07278148 A | 10/1995 |
| JP | 2006510582 A | 3/2006 |
| JP | 2008544755 A | 12/2008 |
| JP | 2009155338 A | 7/2009 |
| JP | 2010504324 A | 2/2010 |
| JP | 2010528993 A | 8/2010 |
| JP | 2012511329 A | 5/2012 |
| JP | 2012254092 A | 12/2012 |
| KR | 20080011428 A | 2/2008 |
| KR | 20100054780 A | 5/2010 |
| WO | WO 94/29351 | 12/1994 |
| WO | WO-0116138 A1 | 3/2001 |
| WO | WO-0119829 A2 | 3/2001 |
| WO | WO-0250071 A1 | 6/2002 |
| WO | WO-02072576 A1 | 9/2002 |
| WO | WO-03004497 A1 | 1/2003 |
| WO | WO-2004017908 A2 | 3/2004 |
| WO | WO-2005005429 A1 | 1/2005 |
| WO | WO-2005011597 A2 | 2/2005 |
| WO | WO-2005014599 A1 | 2/2005 |
| WO | WO-2005047290 A2 | 5/2005 |
| WO | WO 2005/077981 | 8/2005 |
| WO | WO-2006053121 A2 | 5/2006 |
| WO | WO-2006065946 A1 | 6/2006 |
| WO | WO 2006/084015 | 8/2006 |
| WO | WO-2006099075 A2 | 9/2006 |
| WO | WO 2006/121168 | 11/2006 |
| WO | WO-2006133396 A2 | 12/2006 |
| WO | WO 2007/005874 | 1/2007 |
| WO | WO-2007026720 A1 | 3/2007 |
| WO | WO-2007026950 A1 | 3/2007 |
| WO | WO-2007027594 A1 | 3/2007 |
| WO | WO-2007027729 A1 | 3/2007 |
| WO | WO 2007/067444 | 6/2007 |
| WO | WO-2007087068 A2 | 8/2007 |
| WO | WO 2007/136572 | 11/2007 |
| WO | WO-2007136790 A2 | 11/2007 |
| WO | WO-2008033834 A1 | 3/2008 |
| WO | WO-2008033854 A1 | 3/2008 |
| WO | WO-2008033857 A2 | 3/2008 |
| WO | WO-2008039218 A2 | 4/2008 |
| WO | WO-2008054827 A2 | 5/2008 |
| WO | WO-2008144253 A1 | 11/2008 |
| WO | WO 2008/145142 | 12/2008 |
| WO | WO 2008/156712 | 12/2008 |
| WO | WO-2009039397 A2 | 3/2009 |
| WO | WO-2009051822 A1 | 4/2009 |
| WO | WO-2009077334 A1 | 6/2009 |
| WO | WO-2009098144 A1 | 8/2009 |
| WO | WO-2009100309 A2 | 8/2009 |
| WO | WO-2009158571 A1 | 12/2009 |
| WO | WO-2010000633 A1 | 1/2010 |
| WO | WO-2010006947 A1 | 1/2010 |
| WO | WO-2010006970 A1 | 1/2010 |
| WO | WO-2010028236 A1 | 3/2010 |
| WO | WO-2010041549 A1 | 5/2010 |
| WO | WO-2010065898 A2 | 6/2010 |
| WO | WO-2010068788 A1 | 6/2010 |
| WO | WO-2010068806 A1 | 6/2010 |
| WO | WO-2010068810 A2 | 6/2010 |
| WO | WO 2010/077634 | 7/2010 |
| WO | WO 2010/089411 | 8/2010 |
| WO | WO-2010122038 A1 | 10/2010 |
| WO | WO-2011006074 A1 | 1/2011 |
| WO | WO-2011140488 A1 | 11/2011 |
| WO | WO-2011153514 A2 | 12/2011 |
| WO | WO-2012020008 A1 | 2/2012 |
| WO | WO-2012083370 A1 | 6/2012 |
| WO | WO 2012/135408 | 10/2012 |
| WO | WO 2012/145493 | 10/2012 |
| WO | WO-2012130831 A1 | 10/2012 |
| WO | WO-2012135801 A1 | 10/2012 |
| WO | WO-2012143522 A1 | 10/2012 |
| WO | WO-2012156334 A1 | 11/2012 |
| WO | WO-2012158795 A1 | 11/2012 |
| WO | WO 2012/175692 | 12/2012 |
| WO | WO-2013079174 A1 | 6/2013 |
| WO | WO 2013/173223 | 11/2013 |
| WO | WO-2013181634 A2 | 12/2013 |
| WO | WO 2014/055897 | 4/2014 |
| WO | WO 2014/100079 | 6/2014 |
| WO | WO-2014173289 A1 | 10/2014 |
| WO | WO 2015/035606 | 3/2015 |
| WO | WO-2015061752 A1 | 4/2015 |
| WO | WO-2015112900 A1 | 7/2015 |
| WO | WO 2016/000619 | 1/2016 |
| WO | WO-2016008411 A1 | 1/2016 |
| WO | WO-2016024228 A1 | 2/2016 |
| WO | WO-2016025720 A1 | 2/2016 |
| WO | WO-2016064649 A1 | 4/2016 |
| WO | WO-2016087994 A1 | 6/2016 |
| WO | WO-2016100914 A1 | 6/2016 |
| WO | WO-2016105582 A1 | 6/2016 |
| WO | WO-2017025016 A1 | 2/2017 |
| WO | WO-2017046746 A1 | 3/2017 |
| WO | WO-2017059224 A2 | 4/2017 |
| WO | WO-2018033135 A1 | 2/2018 |
| WO | WO-2018033853 A2 | 2/2018 |
| WO | WO-2018137681 A1 | 8/2018 |
| WO | WO-2018193105 A1 | 10/2018 |
| WO | WO-2019001417 A1 | 1/2019 |
| WO | WO-2019034009 A1 | 2/2019 |
| WO | WO-2019108795 A1 | 6/2019 |
| WO | WO-2019157353 A1 | 8/2019 |
| WO | WO-2019183226 A1 | 9/2019 |
| WO | WO-2020249001 A1 | 12/2020 |
| WO | WO-2020249002 A1 | 12/2020 |

OTHER PUBLICATIONS

Abdiche et al., "Assessing kinetic and epitopic diversity across orthogonal monoclonal antibody generation platforms," mABs (Feb.-Mar. 2016), 8(2):264-277.

Arlauckas, S. P. et al., "In vivo imaging reveals a tumor-associated macrophage-mediated resistance pathway in anti-PD-1 therapy," Sci. Transl. Med., 9, eaal3604 (May 2017).

Araki, K. et al., "Programmed cell death 1-directed immunotherapy for enhancing T-cell function," Cold Spring Harbor Symposia on Quantitative Biology, vol. LXXVIII, 239-247 (2013).

Ahmadzadeh, M. et al., "Tumor antigen-specific CD8 T cells infiltrating the tumor express high levels of PD-1 and are functionally impaired," Blood (Aug. 2009), 114(8):1537-1544. doi: 10.1182/blood-2008-12-195792. Epub May 7, 2009.

Berger, R. et al., "Phase I safety and pharmacokinetic study of CT-011, a humanized antibody interacting with PD-1, in patients with advanced hematologic malignancies," Clinical Cancer Research, 14(10):3044-3051 (May 2008).

(56) References Cited

OTHER PUBLICATIONS

Boyd et al., "Deep sequencing and human antibody repertoire analysis," Current Opinion in Immunology (Jun. 2016), 40:103-109. Epub Apr. 8, 2016.

Brahmer, J. R. et al., "Safety and Activity of Anti-PD-L1 Antibody in Patients with Advanced Cancer," N Engl J Med. (Jun. 2012), 366(26):2455-2465.

Brahmer, J. R. et al., "Phase I study of single-agent anti-programmed death-1 (MDX-1106) in refractory solid tumors: safety, clinical activity, pharmacodynamics, and immunologic correlates," J Clin Oncol. (Jul. 2010), 28(19):3167-3175.

Brand, F-X et al., "Prospect for anti-HER2 receptor therapy in breast cancer," Anticancer Research, 26:463-470 (2006).

Casset, F. et al., "A peptide mimetic of an anti-CD4 monoclonal antibody by rational design," Biochemical and Biophysical Research Communications, 307:198-205 (2003).

Chia-Jui, Y. et al., Abstract of "Preliminary results of a phase 1A/1B study of BGB-A317, an anti-PD-1 monoclonal antibody (mAb), in patients with advanced hepatocellular carcinoma (HCC)," Annals of Oncology (2017).

Clynes, R. A. et al., "Inhibitory Fc receptors modulate in vivo cytoxicity against tumor targets," Nat. Med. 6(4):443-446 (Apr. 2000).

Conroy, et al., "Antibodies: From novel repertoires to defining and refining the structure of biologically important targets," Methods (Mar. 2017); 116:12-22. Epub Jan. 11, 2017.

Dahan, R. et al., "FcγRs Modulate the Anti-tumor Activity of Antibodies Targeting the PD-1/PD-L1 Axis," Cancer Cell (Sep. 2015), 28(3):285-95. doi: 10.1016/j.ccell.2015.08.004.

Damschroder et al., "Analysis of human and primate CD2 molecules by protein sequence and epitope mapping with anti-human CD2 antibodies," Mol Immunol. (Aug. 2004), 41(10):985-1000.

Dorfman, D. M. et al., "Programmed death-1 (PD-1) is a marker of germinal center-associated T Cells and angioimmunoblastic T-cell lymphoma," American Journal of Surgical Pathology, 30(7):802-810 (Jul. 2006).

Ferrara et al., "Recombinant renewable polyclonal antibodies," mABs (2015); 7(1):32-41.

Fuller, M. J. et al., "Immunotherapy of chronic hepatitis C virus infection with antibodies against programmed cell death-1 (PD-1)," Proceedings of the National Academy of Sciences, 110(37):15001-15006 (Sep. 2013).

Gelderman, K. A. et al., "Complement function in mAb-mediated cancer immunotherapy," Trends in Immunology, 25(3):158-164 (Mar. 2004).

Hamid, O. et al., "Safety and tumor responses with lambrolizumab (Anti-PD-1) in melanoma," New England Journal of Medicine, 369(2):134-144 (Jul. 2013).

InvivoGen Insight, "IgG-Fc Engineering For Therapeutic Use," Apr./May 2006, 4 pages.

James, L. K. et al., "Potential Mechanisms for IgG4 Inhibition of Immediate Hypersensitivity Reactions," Curr Allergy Asthma Rep. 2016; 16: 23. Published online Feb. 18, 2016. doi: 10.1007/s11882-016-0600-2.

Jiao, Y. et al., "Advances in the research of the anti-cancer agent—Raf kinase inhibitor," Strait Pharmaceutical Journal, vol. 19, No. 8, 2007, pp. 1-5 (with English Abstract).

Khan et al., "Cross-neutralizing anti-HIV-1 human single chain variable fragments (scFvs) against CD4 binding site and N332 glycan identified from a recombinant phage library," Scientific Reports (2017); Article No. 45163, 12 pages.

Könitzer et al., "Generation of a highly diverse panel of antagonistic chicken monoclonal antibodies against the GIP receptor," mABs (Apr. 2017), 9(3):536-549. Epub Jan. 5, 2017.

Lund, J. et al., "Multiple interactions of IgG with its core oligosaccharide can modulate recognition by complement and human Fc gamma receptor I and influence the synthesis of its oligosaccharide chains," J Immunol. (Dec. 1996), 157(11):4963-4969.

Panka, D. J. et al., "Variable region framework differences result in decreased or increased affinity of variant anti-digoxin antibodies," May 1988, Proc. Natl. Acad. Sci. USA, 85:3080-3084.

Parola et al., "Integrating high-throughput screening and sequencing for monoclonal antibody discovery and engineering," Immunology (Jan. 2018), 153(1):31-41. Epub Oct. 30, 2017.

De Pascalis, R. et al., "Grafting of 'Abbreviated' Complementarity-Determining Regions Containing Specificity-Determining Residues Essential for Ligand Contact to Engineer a Less Immunogenic Humanized Monoclonal Antibody," The Journal of Immunology, vol. 169, pp. 3076-3084 (2002).

Paul, W. E. (Ed.), Chap. 9, Structure and Function of Immunoglobulins, In: Fundamental Immunology, Third Edition, pp. 292-295, 1993.

Presta, L. G. et al., "Engineering therapeutic antibodies for improved function," Biochemical Society Transactions (2002) vol. 30, Part 4, pp. 487-490.

Rudikoff, S. et al., "Single amino acid substitution altering antigen-binding specificity," Proc. Natl. Acad. Sci. USA, 79:1979-1983 (Mar. 1982).

Sequence Alignment, 2014, 1 page.

Sheehan et al., "Phage and Yeast Display," Microbial. Spectr. (2015); 3(1):AID-0028-2014; 17 pages.

Shields, R. L. et al., "High Resolution Mapping of the Binding Site on Human IgG1 for FcγRI, FcγRII, FcγRIII, and FcRn and Design of IgG1 Variants with Improved Binding to the FcγR," The Journal of Biological Chemistry, 276(9):6591-6604 (2001).

Smith, K. G. et al., "FcγRIIB in autoimmunity and infection: evolutionary and therapeutic implications," Nat Rev Immunol., May 2010, 10(5):328-43.

Stave, J. W. et al., "Antibody and antigen contact residues define epitope and paratope size and structure," The Journal of Immunology, vol. 191, Jan. 2013, pp. 1428-1435.

Strome, S. E. et al., "A Mechanistic Perspective of Monoclonal Antibodies in Cancer Therapy Beyond Target-Related Effects," The Oncologist, 2007; 12:1084-1095.

Sznol, M. et al., "Antagonist antibodies to PD-1 and B7-H1 (PD-L1) in the treatment of advanced human cancer," Clinical Cancer Research, 19(5):1021-1034 (Mar. 2013).

Van Regenmortel, M. H. V., "Development of a Preventive HIV Vaccine Requires Solving Inverse Problems Which Is Unattainable by Rational Vaccine Design," Front Immunol., 8:2009 (Jan. 2018). eCollection 2017.

Wang, C. et al., "In Vitro Characterization of the Anti-PD-1 Antibody Nivolumab, BMS-936558, and In Vivo Toxicology in Non-Human Primates," Cancer Immunol Res; 2(9):846-856 (Sep. 2014).

Wherry, E. J., "T cell exhaustion," Nature Immunology 12(6):492-499 (2011). Published online May 18, 2011.

Wu, H. et al., "Humanization of a murine monoclonal antibody by simultaneous optimization of framework and CDR residues," Journal of Molecular Biology, 294(1):151-162 (Nov. 1999).

Xu, D. et al., "In vitro characterization of five humanized OKT3 effector function variant antibodies," Cell Immunol. (Feb. 2000), 200(1):16-26.

Zhou et al., "Structural Repertoire of HIV-1-Neutralizing Antibodies Targeting the CD4 Supersite in 14 Donors," Cell (Jun. 2015), 161(6):1280-1292.

Lee et al., "Molecular-level analysis of the serum antibody repertoire in young adults before and after seasonal influenza vaccination," Nat Med. (Dec. 2016), 22(12):1456-1464. Epub Nov. 7, 2016.

Balar, A. et al., "Pembrolizumab (pembro) as first-line therapy for advanced/unresectable or metastatic urothelial cancer: Preliminary results from the phase 2 KEYNOTE-052 study," Annals of Oncology 27 (Supplement 6): vi552-vi587, 2016.

Balbach, S. et al, "Pharmaceutical evaluation of early development candidates: 'The 100 mg-approach'," International Journal of Pharmaceutics, (2004), 275, pp. 1-12.

Beigene Co., Ltd., "Phase I Clinical Research to Evaluate Safety, Tolerability and Pharmacokinetics/Pharmacodynamics Characteristics of BTK Inhibitor, BGB-3111, in Treating Chinese B Lymphocyte Tumor Patients," [Online], May 2016, Retrieved from the

(56) References Cited

OTHER PUBLICATIONS

Internet: http://www.chinadrugtrials.org.cn/clinicaltrials.searchlistdetail. dhtml, Retrieved on: Mar. 21, 2022, 17 pages (with Machine Translation).
Beigene, "Efficacy and Safety of Zanubrutinib in Relapsed or Refractory Chronic Lymphocytic Leukemia/Small Lymphocytic Lymphoma," [Online], Jul. 2017, Retrieved from the Internet: https://clinicaltrials.gov/ct2/show/NCT03206918, Retrieved on: Apr. 4, 2022, 7 pages.
Bellmunt, J. et al., "Keynote-045: open-label, phase II study of pembrolizumab versus investigator's choice of paclitaxel, docetaxel, or vinflunine for previously treated advanced urothelial cancer," Journal for ImmunoTherapy of Cancer, 2016, 4(Suppl. 2):91, Presented at 31st Society for Immunotherapy of Cancer Annual Meeting, Nov. 9-13, 2016, National Harbor, MD, 1 page.
Bellmunt, J. et al., "Pembrolizumab as Second-Line Therapy for Advanced Urothelial Carcinoma," N. Engl. J. Med., vol. 376, No. 11, Mar. 2017, pp. 1015-1026.
Bellmunt, J. et al., "Randomized Phase III Study Comparing Paclitaxel/Cisplatin/Gemcitabine and Gemcitabine/Cisplatin in Patients with Locally Advanced or Metastatic Urothelial Cancer Without Prior Systemic Therapy: EORTC Intergroup Study 30987," J Clin Oncol., Apr. 1, 2012;30(10):1107-1113.
Benson, D. M., Jr. et al., "The PD-1/PD-L1 axis modulates the natural killer cell versus multiple myeloma effect: a therapeutic target for CT-011, a novel monoclonal anti-PD-1 antibody," Blood, 116(13):2286-2294 (Sep. 2010).
Bradshaw, J. M., "The Src, Syk, and Tec family kinases: distinct types of molecular switches," Cell Signal., Aug. 2010, 22(8)1175-1184.
Caira, M. R. et al., "Crystalline polymorphism of organic compounds," Topics in Current Chemistry, Jan. 1, 1998, vol. 19, pp. 163-208.
Cartigny, D. et al., "General Asymmetric Hydrogenation of 2-Alkyl- and 2-Aryl-Substituted Quinoxaline Derivatives Catalyzed by Iridium-Difluorphos: Unusual Halide Effect and Synthetic Application," J. Org. Chem., Apr. 2012, vol. 77, No. 10, pp. 4544-4556.
Conley, M. E. et al., "Primary B Cell Immunodeficiencies: Comparisons and Contrasts," Annu. Rev. Immunol., 27:199-227 (2009).
Davis, R. E. et al., "Chronic active B-cell-receptor signaling in diffuse large B-cell lymphoma," Nature 463:88-92 (2010).
De Toni, E. N. et al., "Tapering of Immunosuppression and Sustained Treatment With Nivolumab in a Liver Transplant Recipient," Gastroenterology, May 2017;152(6):1631-1633. doi: 10.1053/j. gastro.2017.01.063.
Desai, J. et al., "Updated safety, efficacy, and pharmacokinetics (PK) results from the phase I study of BGB-A317, an anti-programmed death-1 (PD-1) mAb in patients with advanced solid tumors," J. Immunother. Cancer, 2016; 4(Suppl 1):P154, 2 pages.
El-Khoueiry, A. B. et al., "Nivolumab in patients with advanced hepatocellular carcinoma (CheckMate 040): an open-label, non-comparative, phase 1/2 dose escalation and expansion trial," Lancet (Jun. 2017) vol. 389, No. 10088, pp. 2492-2502.
Extended European Search Report for European Application No. 14787642.9, dated Jan. 26, 2016, 5 pages.
Extended European Search Report for European Application No. 17841107.0, dated Feb. 21, 2020, 12 pages.
Extended European Search Report for European Application No. 17841172.4, dated Mar. 5, 2020, 6 pages.
Extended European Search Report for European Application No. 18744173.8, dated Oct. 21, 2020, 12 pages.
Extended European Search Report for European Application No. 18823691.3, dated Feb. 22, 2021, 9 pages.
Galsky, M. D. et al.," Effectiveness of Adjuvant Chemotherapy for Locally Advanced Bladder Cancer," J Clin Oncol. Mar. 10, 2016;34(8):825-832.
Gurcan, H. M. et al., "A review of the current use of rituximab in autoimmune diseases," Int. Immunopharmacol., Jan. 2009, 9(1):10-25.
Hackam, D. G. et al., "Translation of research evidence from animals to humans," JAMA, 296(14):1731-1732 (2006).
Hirayama, Y., "Handbook for organic compound crystal—Principle and know-how," 2008, 28 pages.
"History of Changes for Study: NCT02690558. Phase 2 Study Of Pembrolizumab In Combination With Gemcitabine And Cisplatin As Neoadjuvant Therapy," NCT02690558, Mar. 10, Mar. 2017, Retrieved from the Internet: URL:https://clinicaltrials.gov/ct2/history/NCT02690558?V_4=View#StudyPageTop, 5 pages.
Humphries, L. A. et al., "Tec kinases mediate sustained calcium influx via site-specific tyrosine phosphorylation of the phospholipase Cgamma Src homology 2-Src homology 3 linker," J. Biol.Chem., Sep. 2004, 279(36):37651-37661.
International Search Report and Written Opinion for International Application No. PCT/CN2014/075943, dated Jul. 18, 2014, 10 pages.
International Search Report and Written Opinion for International Application No. PCT/CN2017/098023, dated Nov. 16, 2017, 10 pages.
International Search Report and Written Opinion for International Application No. PCT/CN2018/074108, dated Apr. 23, 2018, 12 pages.
International Search Report and Written Opinion for International Application No. PCT/CN2018/092827, dated Sep. 29, 2018, 14 pages.
International Search Report and Written Opinion for International Application No. PCT/CN2018/100145, dated Nov. 14, 2018, 8 pages.
International Search Report and Written Opinion for International Application No. PCT/CN2020/095352, dated Sep. 16, 2020, 23 pages.
International Search Report and Written Opinion for International Application No. PCT/CN2020/095353, dated Sep. 15, 2020, 23 pages.
International Search Report and Written Opinion for International Application No. PCT/IB2017/054955, dated Sep. 10, 2018, 16 pages.
International Search Report and Written Opinion for International Application No. PCT/US2018/063068, dated Feb. 27, 2019, 7 pages.
International Search Report and Written Opinion for International Application No. PCT/US2019/017313, dated Jun. 25, 2019, 16 pages.
Jenkins, S. M. et al., "Substituent variation in azabicyclic triazole- and tetrazole-based muscarinic receptor ligands," J. Med. Chem., 35(13):2392-2406 (1992).
Jie, L., "Deuterated Drugs Progress," Chemical Engineering Design Communication Medicine and Chemical Industry, 2016, vol. 42, No. 4, p. 199.
Jordan, V. C., "Tamoxifen: A most unlikely pioneering medicine," Nature Reviews: Drug Discovery, 2:205-213 (2003).
Kersseboom, R. et al., "Constitutive activation of Bruton's tyrosine kinase induces the formation of autoreactive IgM plasma cells," Eur. J. Immunol. 40:2643-2654, 2010.
Khan, W. N., "Regulation of B lymphocyte development and activation by Bruton's tyrosine kinase," Immunol. Res., 23(2/3):147-156 (2001).
Kim, K.-H. et al., "Imidazo[1,5-a]quinoxalines as irreversible BTK inhibitors for the treatment of rheumatoid arthritis," Bioorg. Med. Chem. Lett., 21:6258-6263 (2011).
Kourtzelis, I., et al., "The Dual Role of Complement in Cancer and its Implication in Anti-Tumor Therapy," Annals of Translational Medicine, 2016, vol. 4(14), 14 pages.
Kudo, M., Immune Checkpoint Blockade in Hepatocellular Carcinoma: 2017 Update, Liver Cancer, Nov. 2016; 6(1):1-12.
Kudo, M., "Immune Checkpoint Inhibition in Hepatocellular Carcinoma: Basics and Ongoing Clinical Trials," Oncology, 2017;92 Suppl 1:50-62. doi: 10.1159/000451016. Epub Feb. 2, 2017.
Li, N. et al., "BGB-3111 is a novel and highly selective Bruton's tyrosine kinase (BTK) inhibitor," Cancer Center, vol. 75, No. 15, Supp. 1, Abstract No. 2597, 106th Annual Meeting of the American Association for Cancer Research, AACR 2015, Philadelphia, PA, United States, Aug. 2015, 2 pages.

(56) References Cited

OTHER PUBLICATIONS

Lou, Y. et al., "Bruton's tyrosine kinase inhibitors: Approaches to potent and selective inhibition, preclinical and clinical evaluation for inflammatory diseases and B cell malignancies," J. Med. Chem., 55(10):4539-4550 (2012).

Luo, J. et al., "Modern Physical Pharmaceutics Theory and Practice," Shang Hai Science and Technology Literature Publishing House, Apr. 2005, pp. 293-295.

MedChemExpress, "Zanubrutinib," Product Data Sheet, Retrieved from the Internet: www.medchemexpress.com, Retrieved Aug. 17, 2021, 2 pages.

Mohamed, A. J. et al., "Bruton's tyrosine kinase (Btk): function, regulation, and transformation with special emphasis on the PH domain," Immunol. Rev., 228:58-73 (2009).

Office Action for Japanese Application No. 2019-508889, dated Jun. 22, 2021, 7 pages.

Pan, Z, "Bruton's tyrosine kinase as a drug discovery target," Drug News Perspect, 21(7):357-362 (2008).

Pan, Z. et al., "Discovery of Selective Irreversible Inhibitors for Bruton's Tyrosine Kinase," ChemMedChem 2007, vol. 2, pp. 58-61.

Piao, C-Y et al., "Lamivudine treatment in patients with HBV-related hepatocellular carcinoma—using an untreated, matched control cohort," Acta Med. Okayama, vol. 59, No. 5, pp. 217-224 (2005).

Plimack, E. R. et al., "Pembrolizumab (MK-3475) for advanced urothelial cancer: Updated results and biomarker analysis from KEYNOTE-012," J. Clin. Oncol., vol. 33, Issue 15 Suppl., May 2015, Abstract 4502, 2 pages.

Rokosz, L. L. et al., "Kinase inhibitors as drugs for chronic inflammatory and immunological diseases: progress and challenges," Expert Opin. Ther. Targets, 12(7):883-903 (2008).

Samonakis, D. N. et al., "Systemic treatment for hepatocellular carcinoma: Still unmet expectations," World J Hepatol., Jan. 2017; 9(2):80-90.

Sharma, P. et al., "Efficacy and safety of nivolumab monotherapy in metastatic urothelial cancer (mUC): Results from the phase I/II CheckMate 032 study," J. Clin. Oncol., vol. 34, No. 15 Suppl., May 2016, p. 4501.

Sharma, P. et al., "Nivolumab monotherapy in recurrent metastatic urothelial carcinoma (CheckMate 032): a multicentre, open-label, two-stage, multi-arm, phase 1/2 trial," Lancet Oncol., Nov. 2016, vol. 17, No. 11, pp. 1590-1598.

Shioji, Y., "Production Technology of Solid Preparations," Tokyo, CMC Publication, Jan. 27, 2003, Popular Edition, pp. 9 and 12-13.

Singhal, D. et al., "Drug polymorphism and dosage form design: a practical perspective," Advanced Drug Delivery Reviews, 56 (2004) pp. 335-347.

Smith, C. I. et al., "Expression of Bruton's agammaglobulinemia tyrosine kinase gene, BTK, is selectively down-regulated in T lymphocytes and plasma cells," J. Immunol., Jan. 1994, 152(2):557-565.

Takada, N., "Bulk Drug Form Screening and Selection at Drug Discovery Phase," Pharm Stage, Jan. 2007, vol. 6, No. 10, pp. 20-25.

Takayama, T. et al., "Effects of the novel and potent lymphocyte-specific protein tyrosine kinase inhibitor TKM0150 on mixed lymphocyte reaction and contact hypersensitivity in mice," Arzneimittelforschung, 60(5):282-285 (2010).

Takayama, T. et al., "Ring-fused pyrazole derivatives as potent inhibitors of lymphocyte-specific kinase (Lck): Structure, synthesis, and SAR," Bioorganic & Medicinal Chemistry Letters, 20(1):112-116 (Jan. 2010).

Tam, C. S. et al., "A head-to-head Phase III study comparing zanubrutinib versus ibrutinib in patients with Waldenström macroglobulinemia," Future Oncology, vol. 14, No. 22, Sep. 2018, pp. 2229-2237.

Topalian, S. L., "Safety, Activity, and Immune Correlates of Anti-PD-1 Antibody in Cancer," N. Engl. J. Med., Jun. 2012; vol. 366, No. 26, pp. 2443-2454.

Uckun, F. M. et al., "Bruton's tyrosine kinase as a new therapeutic target," Anti-Cancer Agents in Medicinal Chemistry, 7(6):624-632 (2007).

Vetrie, D. et al., "The gene involved in X-linked agammaglobulinaemia is a member of the src family of protein-tyrosine kinases," Nature, 361:226-233 (1993).

Wanich, N. et al., "High prevalence of hepatocellular carcinoma in patients with chronic hepatitis B infection in Thailand," Asian Pac J Cancer Prev, vol. 17, No. 6, pp. 2857-2860 (2016).

Wenzel, S-S et al., "MCL1 is deregulated in subgroups of diffuse large B-cell lymphoma," Leukemia, vol. 27, pp. 1381-1390 (2013).

Wilson, W. H. et al., "686—The Bruton's Tyrosine Kinase (Btk) Inhibitor, Ibrutinib (PCI-32765), Has Preferential Activity in the ABC Subtype of Relapsed/Refractory De Novo Diffuse Large B-Cell Lymphoma (DLBCL): Interim Results of a Multicenter, Open-Label, Phase2 Study," Poster #686, 54th American Society of Hematology (ASH) Annual Meeting Abstract (Dec. 10, 2012), 3 pages.

ANTI-PD-L1 ANTIBODIES AND THEIR USE AS THERAPEUTICS AND DIAGNOSTICS

SEQUENCE LISTING

The instant application contains a Sequence Listing which has been submitted in ASCII format via EFS-Web and is hereby incorporated by reference in its entirety. Said ASCII copy, created on Dec. 5, 2019 is named "BEIG_009_02US_SeqList.txt" and is 43.2 kilobytes in size.

INTRODUCTION

PD-L1 was initially cloned as a member (known as B7-H1) of B7 protein family (Doug et al., 1999 Nature Med 5:1365). It binds to Programmed Death-1 (PD-1) receptor and activates negative regulatory signaling pathway, inhibiting T-cell proliferation and activities (Freeman et. al. 2000 J Exp Med 192:1027). Therefore, it was also termed as PD-1 ligand 1 (PD-L1 or CD274). To date, two sequence-related ligands, PD-L1 (B7-H1) and PD-L2 (B7-DC), were identified that interact with PD-1, induce negative signal transduction and inhibit TCR and CD28 mediated T-cell activation, cell proliferation and secretion of growth factors and cytokines such as IL-2 and IFN-γ (Riley et. al. 2009 Immunol Rev 229:114).

Human PD-L1 gene encodes a full-length protein of 290 amino acid residues (NCBI accession NP_054862.1) with a leader peptide, which is removed after PD-L1 is expressed on cell surface as a mature protein. The calculated molecular weight of the full length PD-L1 is 33 kD. However, the observed molecular weight is around 50 kD due to glycosylation, based on Western blot data from ours and others.

PD-L1 was found constitutively expressed in human heart, lung, thymus and vascular endothelial cells, and expressed at a low level in many other human tissues and cell types including antigen presenting cells, peripheral blood monocytes and other immune cells (Freeman et. al. 2000 J Exp Med 192:1027; Eppihimer et. al. 2002 Microcirculation 9:133). When stimulated by IFN-γ, IL-12 and type I interferons, many of those cell types were found expressing increased level of PD-L1 (Bald et. al. 2014 Cancer Discov 4:674-687; Planes et. al. 2014 J Virol 88:6672-6689).

Aberrant up-regulation of PD-L1 expression in tumor cells were reported in varieties of cancers involved in different types of tissues and organs such as lung (Konishi et. al. 2004 Clin Cancer Res 10:5094), liver (Shi et. al. 2008 Int J Cancer 128:887; Gao et. al., 2009 Clin Cancer Res 15:971), stomach (Wu et. al. 2006 Acta Histochem 108:19), kidney (Thompson et. al. 2004 Proc Natl Acad Sci 101: 17174; Thompson et. al. 2007 Clin Cancer Res 13:1757), breast (Ghebeh et. al. 2006 Neoplasia 8:190), ovary (Hamanishi et. al. 2007 Proc Natl Acad Sci 104:3360), pancreas (Nomi et. al. 2007 Clin Cancer Res 13:2151), melanocytes (Hino et. al. 2010 Cancer 116:1757) and esophagus (Ohigashi et. al. 2005 Clin Cancer Res 11:2947). More frequently, the increased expression of PD-L1 in those cancers is associated to poor prognosis in patient survival outcome.

Blockade of PD-L1 engaging PD-1 receptor by B7-H1Ig or anti-PD-L1 antibody stimulated T-cell proliferation and functional activities (Dong et. al. 1999 Nature Med 5:1365; Freeman et. al. 2000 J Exp Med 192:1027; Tamura et. al. 2001 Blood 97:1809; Iwai et. al. 2002 PNAS 99:12293), enhanced immune responses against tumor growth and viral infection (Iwai et. al. 2002 PNAS 99:12293). Those observations suggested that inhibition of PD-L1/PD-1 signaling may activate immune responses not only against cancer cell growth, but also against viral infection and expansion in human. The prevalent hepatocyte infection viruses, HBV and HCV, induce overexpression of PD-1 ligands in hepatocytes and activate PD-1 signaling in T-effecter cells, resulting T-cell exhaustion and tolerance to the viral infection (Boni et. al. 2007 J Virol 81:4215; Golden-Mason et. al. 2008 J Immunol 180; 3637). Likewise, the popular HIV infection frequently evades human immune system by similar mechanism. Therapeutic modulation of PD-L1 induced signaling by antagonist molecules may revert immune cells from tolerance, and reactivated to eradicate cancer and chronic viral infection (Blank et. al. 2005 Cancer Immunol Immunother 54:307; Okazaki et. al. 2007 Int Immunol 19:813).

Recently, it is discovered that PD-L1 also specifically interacts to B7-1 (another B7 family member, also known as CD80) besides binding to PD-1 (Butte et. al. 2007 Immunity 27:111). Initial evidences indicated that interaction of PD-L1 to CD80 exerts negative regulation to T-cell function and activity, and blockage of PD-L1 and CD80 interaction in mice elicited stronger immune responses to OVA antigen challenge (Park et. al. 2010 Blood 116:1291). Therefore, simultaneously blocking PD-L1 binding to PD-1 and CD80 may exert additive or synergistic effect against cancer and viral infection.

SUMMARY OF THE INVENTION

The invention provides methods and compositions for immune-activation by inhibiting PD-L1-mediated signaling and function. In one aspect, the invention provides an antibody antigen binding domain which specifically binds human PD-L1, and comprises a complementarity determining region (CDR) sequence described herein. The CDRs are amenable to recombination into heavy chain variable region (Vh) and light chain variable regions (Vk) which comprise (CDR-H1, CDR-H2 and CDR-H3) and (CDR-L1, CDR-L2 and CDR-L3) sequences, respectively and retain PD-L1-specific binding and/or functionality.

In particular embodiments, the domain comprises CDR1, CDR2 and CDR3, in a combination selected from (a)-(r) as follows, wherein the antibody (Ab), heavy chain (HC) or light chain (LC) and CDR nomenclature system (Kabat, IMGT or composite) from which the CDR combinations derive are shown in the first column, and residues in bold text are Kabat system, and residues underlined are IMGT system:

| Ab, Chain | | System | CDR1 | CDR2 | CDR3 |
|---|---|---|---|---|---|
| mu333/ hu333-1A vh | a | Kabat | GFSLTSYGVH SEQ ID NO: 9, res. 6-10 | VIWAGGSTNYNSALMS SEQ ID NO: 10 | AKPYGNSAMDY SEQ ID NO: 11, res. 3-11 |
| | b | IMGT | SEQ ID NO: 9, res. 1-8 | SEQ ID NO: 10, res. 2-8 | SEQ ID NO: 11 |
| | c | Comp. | SEQ ID NO: 9 | SEQ ID NO: 10 | SEQ ID NO: 11 |

| Ab, Chain | | System | CDR1 | CDR2 | CDR3 |
|---|---|---|---|---|---|
| hu333-<br>2B/3A2<br>vh | d<br>e<br>f | Kabat<br>IMGT<br>Comp. | GFSLTSYGVH<br>SEQ ID NO: 9, res. 6-10<br>SEQ ID NO: 9, res. 1-8<br>SEQ ID NO: 9 | VIWAGGSTNYVDSVKG<br>SEQ ID NO: 24<br>SEQ ID NO: 24, res. 2-8<br>SEQ ID NO: 24 | AKPYGNSAMDY<br>SEQ ID NO: 11, res. 3-11<br>SEQ ID NO: 11<br>SEQ ID NO: 11 |
| hu333-<br>3C2/3H2<br>vh | g<br>h<br>i | Kabat<br>IMGT<br>Comp. | GFSLTSYGVH<br>SEQ ID NO: 9, res. 6-10<br>SEQ ID NO: 9, res. 1-8<br>SEQ ID NO: 9 | VIWAGGSTNYNSALMS<br>SEQ ID NO: 25<br>SEQ ID NO: 25, res. 2-8<br>SEQ ID NO: 25 | AKPYGNSAMDY<br>SEQ ID NO: 11, res. 3-11<br>SEQ ID NO: 11<br>SEQ ID NO: 11 |
| hu333-<br>4A2<br>vh | j<br>k<br>l | Kabat<br>IMGT<br>Comp. | GFSLTSYGVH<br>SEQ ID NO: 9, res. 6-10<br>SEQ ID NO: 9, res. 1-8<br>SEQ ID NO: 9 | VIWAGGSTNYNSALMS<br>SEQ ID NO: 24<br>SEQ ID NO: 24, res. 2-8<br>SEQ ID NO: 24 | AKPYGNSAMDY<br>SEQ ID NO: 26, res. 3-11<br>SEQ ID NO: 26<br>SEQ ID NO: 26 |
| hu333-<br>4B2<br>vh | m<br>n<br>o | Kabat<br>IMGT<br>Comp. | GFSLTSYGVH<br>SEQ ID NO: 9, res. 6-10<br>SEQ ID NO: 9, res. 1-8<br>SEQ ID NO: 9 | VIWAGGSTNYNSALMS<br>SEQ ID NO: 25<br>SEQ ID NO: 25, res. 2-8<br>SEQ ID NO: 25 | AKPYGNSAMDY<br>SEQ ID NO: 26, res. 3-11<br>SEQ ID NO: 26<br>SEQ ID NO: 26 |
| mu333/<br>hu333's<br>vk | p<br>q<br>r | Kabat<br>IMGT<br>Comp. | KASQDVGIVVA<br>SEQ ID NO: 12<br>SEQ ID NO: 12, res. 4-9<br>SEQ ID NO: 12 | WASIRHT<br>SEQ ID NO: 13<br>SEQ ID NO: 13, res. 1-3<br>SEQ ID NO: 13 | QQYSNYPLYT<br>SEQ ID NO: 14<br>SEQ ID NO: 14<br>SEQ ID NO: 14 |

In particular embodiments, the domain comprises a heavy chain variable region (Vh) comprising a CDR1, CDR2 and CDR3 combination selected from (a)-(o), and a light chain variable region (Vic) comprising a CDR1, CDR2 and CDR3 combination selected from (p)-(r), In particular embodiments, the domain comprises CDR1, CDR2 and CDR3, in a combination selected from (c), (f), (i), (l), (o) and (r), as follows:

| Ab, Chain | | CDR1 | CDR2 | CDR3 |
|---|---|---|---|---|
| mu333 vh | (c) | SEQ ID NO: 9 | SEQ ID NO: 10 | SEQ ID NO: 11 |
| hu333 2B/3A2 vh | (f) | SEQ ID NO: 9 | SEQ ID NO: 24 | SEQ ID NO: 11 |
| hu333 2C/3H2 vh | (i) | SEQ ID NO: 9 | SEQ ID NO: 25 | SEQ ID NO: 11 |
| hu333 4A2 vh | (l) | SEQ ID NO: 9 | SEQ ID NO: 24 | SEQ ID NO: 26 |
| hu333 42B vh | (o) | SEQ ID NO: 9 | SEQ ID NO: 25 | SEQ ID NO: 26 |
| hu333 vk | (r) | SEQ ID NO: 12 | SEQ ID NO: 13 | SEQ ID NO: 14 |

In particular embodiments, the domain comprises a heavy chain variable region (Vh) or a light chain variable region (Vk), comprising a sequence that is:

(SEQ ID NO: 6)
 mu333 vh;

(SEQ ID NC): 8)
 mu333 vk;

(SEQ ID NO: 15)
 hu333-1A vh:

(SEQ ID NO: 16)
 hu333-1A vk;

(SEQ ID NO: 17)
 hu333-2B vh;

(SEQ ID NO: 18)
 hu333-3A2 vh;

(SEQ ID NO: 19)
 hu333-3C2 vh;

(SEQ ID NO: 20)
 hu333-3H2 vh;

(SEQ ID NO: 21)
 hu333-4A2 vh;

(SEQ ID NO: 22)
 hu333-4B2 vh;
or (SEQ ID NO: 23)
 hu333-4B2 vk,

In particular embodiments, the domain comprises a heavy chain variable region (Vh) and a light chain variable region (Vk) comprising a sequence that is:

(SEQ ID NOS: 6 and 8)
 mu333 vh and vk;

(SEQ ID NOS: 15 and 16)
 hu333-1A vh and vk;

(SEQ ID NOS: 17 and 16)
 hu333-2B vh and vk;

(SEQ ID NOS: 18 and 23)
 hu333-3A2 vh and vk;

(SEQ ID NOS: 19 and 23)
 hu333-3C2 vh and vk;

(SEQ ID NOS: 20 and 23)
 hu333-3H2 vh and vk;

(SEQ ID NOS: 21. and 23)
 hu333-4A2 vh and vk;
or (SEQ ID NOS: 22 and 23)
 hu333-4B2 vh and vk.

In particular embodiments, the domain comprises comprising a heavy chain variable region (Vh) or a light chain variable region (Vk) comprising:

hu333-4B2 vh;           (SEQ ID NO: 22)
        or
        hu333-4B2 vk.           (SEQ ID NO: 23)

In particular embodiments, the domain comprises comprising a heavy chain variable region (Vh) and a light chain variable region (Vk) comprising:

hu333-4A2 vh and vk;    (SEQ ID NOS: 21 and 23)
        or
        hu333-4B2 vh and vk.    (SEQ ID NOS: 22 and 23)

In particular embodiments, the domain specifically binds PD-L1 residues: D26 and R113.

The invention also provides antibodies, particularly monoclonal antibodies, and F(ab) or F(ab)2 comprising a subject PD-L1 binding domain.

The invention also provides novel polynucleotides such as cDNAs and expression vectors, encoding a subject PD-L1 antigen binding domain, and cells comprising such polynucleotides, and non-human animals comprising such cells. The polynucleotides may be operably linked to a heterologous transcription regulating sequence for expression, and may be incorporated into such vectors, cells, etc.

The invention provides methods of using the subject domains by administering the domain to a person determined to have cancer or a viral infection or to otherwise be in need of PD-L1 antagonism.

The compositions of the invention are useful for the treatment of cancer, neurodegenerative and infectious, particularly viral, diseases and other conditions in which inappropriate or detrimental expression of the human PD-1 and/or is a component of the etiology or pathology of the condition. Hence, the invention provides methods for treating cancer or inhibiting tumor progression in a subject in need thereof with a subject anti-PD-L1 protein, and the humanized anti-PD-1 mAbs are used as therapeutic agents to treat human diseases that are involved in suppression of immune cells by PD-1 mediated intracellular signaling, leading to disease progression, particularly cancers and viral infections.

The invention further provides the use of subject polynucleotides for the manufacture of a medicament for treating cancer or inhibiting tumor progression in a subject.

The invention includes all combinations of the recited particular embodiments. Further embodiments and the full scope of applicability of the invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description. All publications, patents, and patent applications cited herein, including citations therein, are hereby incorporated by reference in their entirety for all purposes.

BRIEF DESCRIPTION OF THE DRAWINGS

In FIG. 2A, ELISA plate was coated by PD-L1/His at 100 ng per well. The binding signal strength in ELISA was indicated by direct $OD_{450}$ readings in y-axis. Concentrations of mAbs or mouse IgG were indicated by x-axis.

In FIG. 2B, HEK293/PD-L1 cells were stained with a serial dilution of murine anti-PD-L1 mAbs or control mouse IgG. The binding signal strength was indicated by MFI (mean fluorescence intensity) in FACS analyses. Concentrations of mAbs or mouse IgG were indicated by x-axis.

FIG. 13A: Binding activities to mutant PD-L1 by hu333-4B2-IgG1. FIG. 13B: Binding activities to mutant PD-L1 by Y1-IgG1.

FIG. 14A: Dose-dependent reaction curves of murine mAb or murine chimeric mAb binding to a mixture of human serum and PD-L1/His protein. Serial dilutions of PD-L1/His protein in PBS were coated onto 96-well MaxiSorp ELISA plate as indicated, and human serum pool (from three healthy donors) were added at a fixed final concentration of 5%. Three ug/mL indicated mAbs were added to each well and incubated for one hour at room temperature. FIG. 14B: Histogram showed the average OD450 readings of three data points in left side (coated mainly with human serum proteins and with very little PD-L1/His) of curves for each mAb and the negative control (without mAb).

DESCRIPTION OF PARTICULAR EMBODIMENTS OF THE INVENTION

Figure 1:
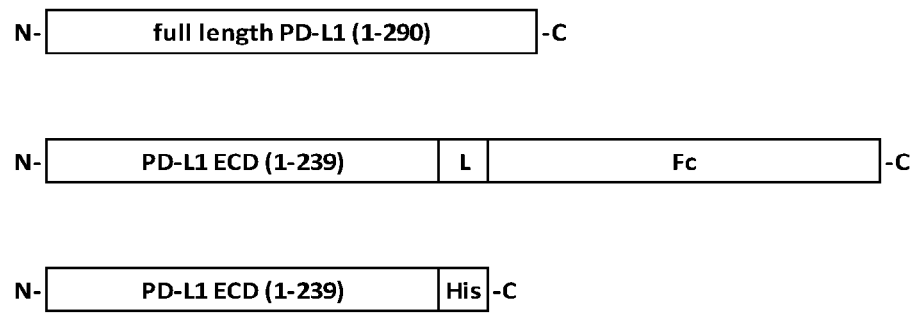
FIG. 1. Schematic presentation of full length PD-L1 (top), PD-L1/Fc (middle) and PDL1/His (bottom). ECD: extracellular domain. L: linker. Fc: γ4Fc fragment from human IgG4. H: His tag. N: N-terminus. C: C-terminus.

PD-L1 initiates inhibitory signaling in immune cells when engaged by its ligands, PD-L1 or PD-L2. In the cases of cancer outgrowth and viral infection, the activation of PD-1 signaling promotes immune tolerance, leading to the cancers or virus-infected cells escaping from immune surveillance and cancer metastasis or viral load increase. Inhibition of PD-L1 mediated cellular signaling by therapeutic agents can activate immune cells including T-cells, B-cells and NK cells, and therefore enhance immune cell functions inhibiting cancer cell growth or viral infection, and restore immune surveillance and immune memory function to treat such human diseases.

The invention provides antibodies whose functions are antagonistic to PD-L1-induced cellular signaling in immune cells. Murine anti-PD-L1 antibodies were humanized to a high degree of similarity to human antibodies in the framework regions. The full antibodies made in the modified human IgG variant format have a unique set of features in the aspects of effector functions and physicochemical properties. The disclosed anti-PD-L1 antibodies are suitable for therapeutic uses in cancer treatment, controlling viral infections and other human diseases that are mechanistically involved in exacerbated immune tolerance.

Unless the context indicates otherwise, the term "antibody" is used in the broadest sense and specifically covers antibodies (including full length monoclonal antibodies) and antibody fragments so long as they recognize PD-L1. An antibody molecule is usually monospecific, but may also be described as idiospecific, heterospecific, or polyspecific. Antibody molecules bind by means of specific binding sites to specific antigenic determinants or epitopes on antigens. "Antibody fragments" comprise a portion of a full length antibody, generally the antigen binding or variable region thereof. Examples of antibody fragments include Fab, Fab', F(ab').sub.2, and Fv fragments; diabodies; linear antibodies; single-chain antibody molecules; and multispecific antibodies formed from antibody fragments.

Natural and engineered antibody structures are well known in the art, e.g. Strohl et al., *Therapeutic antibody engineering: Current and future advances driving the strongest growth area in the pharmaceutical industry*, Woodhead Publishing Series in Biomedicine No. 11, October 2012; Holliger et al. Nature Biotechnol 23, 1126-1136 (2005); Chames et al. Br J Pharmacol. 2009 May; 157(2): 220-233.

Monoclonal antibodies (MAbs) may be obtained by methods known to those skilled in the art. See, for example Kohler et al (1975); U.S. Pat. No. 4,376,110; Ausubel et al (1987-1999); Harlow et al (1988); and Colligan et al (1993). The mAbs of the invention may be of any immunoglobulin class including IgG, IgM, IgE, IgA, and any subclass thereof. A hybridoma producing a mAb may be cultivated in vitro or in vivo. High titers of mAbs can be obtained in in vivo production where cells from the individual hybridomas are injected intraperitoneally into mice, such as pristine-primed Balb/c mice to produce ascites fluid containing high concentrations of the desired mAbs. MAbs of isotype IgM or IgG may be purified from such ascites fluids, or from culture supernatants, using column chromatography methods well known to those of skill in the art.

An "isolated polynucleotide" refers to a polynucleotide segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA, which is part of a hybrid gene encoding additional polypeptide sequence.

A "construct" means any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule where one or more polynucleotide molecule has been linked in a functionally operative manner, i.e. operably linked. A recombinant construct will typically comprise the polynucleotides of the invention operably linked to transcriptional initiation regulatory sequences that will direct the transcription of the polynucleotide in the intended host cell. Both heterologous and non-heterologous (i.e., endogenous) promoters can be employed to direct expression of the nucleic acids of the invention.

A "vector" refers any recombinant polynucleotide construct that may be used for the purpose of transformation, i.e. the introduction of heterologous DNA into a host cell. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors".

An "expression vector" as used herein refers to a nucleic acid molecule capable of replication and expressing a gene of interest when transformed, transfected or transduced into a host cell. The expression vectors comprise one or more phenotypic selectable markers and an origin of replication to ensure maintenance of the vector and to, if desired, provide amplification within the host. The expression vector further comprises a promoter to drive the expression of the polypeptide within the cells. Suitable expression vectors may be plasmids derived, for example, from pBR322 or various pUC plasmids, which are commercially available. Other expression vectors may he derived from bacteriophage, phagemid, or cosmid expression vectors.

| Description of Sequence Listing | |
| --- | --- |
| SEQ ID No. 1 | PD-L1 full length cDNA |
| SEQ ID No. 2 | PD-L1 full length PRT |
| SEQ ID No. 3 | PD-L1 ECD cDNA |
| SEQ ID No. 4 | PD-L1 ECD PRT |
| SEQ ID No. 5 | mu333 cDNA-Vh |
| SEQ ID No. 6 | mu333 pro-Vh |
| SEQ ID No. 7 | mu333 cDNA-Vk |
| SEQ ID No. 8 | mu333 pro-Vk |
| SEQ ID No. 9 | mu333 H-CDR1 |
| SEQ ID No. 10 | mu333 H-CDR2 |
| SEQ ID No. 11 | mu333 H-CDR3 |
| SEQ ID No. 12 | mu333 L-CDR1 |
| SEQ ID No. 13 | mu333 L-CDR2 |
| SEQ ID No. 14 | mu333 L-CDR3 |
| SEQ ID No. 15 | hu333-1A pro-vh |
| SEQ ID No. 16 | hu333-1A pro-vk |

-continued

| Description of Sequence Listing | |
| --- | --- |
| SEQ ID No. 17 | hu333-2B pro-vh |
| SEQ ID No. 18 | hu333-3A2 pro-vh |
| SEQ ID No. 19 | hu333-3C2 pro-vh |
| SEQ ID No. 20 | hu333-3H2 pro-vh |
| SEQ ID No. 21 | hu333-4A2 pro-vh |
| SEQ ID No. 22 | hu333-4B2 pro-vh |
| SEQ ID No. 23 | hu333-4B2 pro-vk |
| SEQ ID No. 24 | hu333-4A2 H-CDR2 |
| SEQ ID No. 25 | hu333-4B2 H-CDR2 |
| SEQ ID No. 26 | hu333-4B2 H-CDR3 |
| SEQ ID No. 27 | huIgG1wt pro |
| SEQ ID No. 28 | huIgG1mc pro |
| SEQ ID No. 29 | huIgG1mf pro |
| SEQ ID No. 30 | hu333-4A2-IgG1mc HC pro |
| SEQ ID No. 31 | hu333-4B2-IgG1mc HC pro |
| SEQ ID No. 32 | hu333-4B2-IgG1mf LC pro |
| SEQ ID No. 33 | hu333-4B2-IgG1mf HC pro |

EXAMPLES

Example 1. Generation of Anti-PD-L1 Monoclonal Antibody

Murine anti-human PD-L1 monoclonal antibodies (mAbs) were generated using hybridoma fusion technology (Kohler and Milstein 1975 Nature 256:495-497; Mechetner 2007 Methods Mol Biol 378:1-13) with modifications. MAbs with high binding activities in enzyme-linked immunosorbent assay (ELISA) and fluorescence-activated cell sorting (FACS) assay were selected for further characterization in cell-based functional assays.

PD-L1 and CD80 Recombinant Proteins

The full length human PD-L1 cDNA was synthesized by GeneScript (Nanjing, China) based on published sequence (NCBI reference sequence NM_014143.3) (SEQ. NO. 1 and 2). The extracellular domain consisting of amino acids (AA) 1-239 of human PD-L1 (SEQ. NO. 3 and 4) was PCR-amplified and subcloned into pcDNA3.1-based expression vector (Invitrogen, Carlsbad, Calif., USA) with C-terminus fused with either a Fc region of human IgG4 or a His tag, which resulted in two recombinant PD-L1 fusion constructs, PD-L1-ECD/Fc and PD-L1-ECD/His (abbreviated as PD-L1/Fc and PD-L1/His). The schematic diagram of the PD-L1 fusion proteins were shown in FIG. 1. The recombinant PD-L1 fusion proteins were expressed in 293-F cells (Cat. No. R79007, Invitrogen) by transient transfection according to manufacturer's instruction (Invitrogen). The conditioned media containing the secreted recombinant proteins was collected and cleared by centrifugation at 15000 g for 30 minutes. PD-L1/Fc was purified using a Protein G Sepharose Fast Flow column (Cat. No. 17061805, GE Life Sciences, Shanghai, China). PD-L1/His was purified through Ni-Sepharose Fast Flow affinity chromatography (Cat. No. 17531801, GE Life Sciences), followed by size exclusion chromatography using a HiLoad 16/60 Superdex 200 column (Cat. No. 17106901, GE Life Sciences). Both PD-L1/Fc and PD-L1/His proteins were dialyzed against phosphate buffered saline (PBS) and stored in −80° C. freezer in small aliquots.

Expression plasmid containing full-length human PD-1 cDNA was obtained from Origene (Cat. No. SC117011, NCBI Accession No: NM_005018.1, Beijing, China). The extracellular domain consisting of amino acid (AA) 1-168 of PD-1 was PCR-amplified, and subcloned in pcDNA3.1-based expression vector (Invitrogen, Carlsbad, Calif., USA)

with C-terminus fused to the Fc domain of human IgG4 heavy chain, abbreviated as PD-1/Fc.

The human CD80 (B7-1) cDNA was synthesized by GeneScript according to the published sequence (NCBI access number NM_005191.3). The extracellular domain (AA1-242) of CD80 was fused with human Fc at C-terminus and subcloned in a mammalian expression vector similar to the method described previously (U.S. Pat. No. 8,735,553). The fusion protein was named as CD80-ECD/Fc or CD80/Fc.

Stable Cell Line Expressing PD-L1

Stable cell line expressing human PD-L1 was established by transfection of pcDNA3.1 plasmid containing PD-L1 into HEK293 (ATCC, Manassas, Va., USA), and followed by selection with media containing 600 micrograms of hygromycin (Cat. No. 10687-010, Invitrogen) per milliliter. Single clones were isolated by picking up single colonies from culture-dish surface. All clones were screened by FACS analysis and Western blot using PD-L1 antibody (Cat. No. 17-5983, eBioscience, San Diego, USA), and the top expression clones were used for FACS binding analyses and functional assays.

Immunization and Hybridoma Clone Generation

Murine anti-human PD-L1 monoclonal antibodies were generated using the hybridoma fusion technology. All animal protocols were reviewed by and performed following BeiGene Animal Care and Use Procedure. Ten to twelve week-old Balb/c mice (HFK Bioscience, Beijing, China) were immunized three times (3 weeks apart between injections) subcutaneously and/or intra-peritoneally, each immunization was done with 100 uL of adjuvant (Cat. No. KX0210041, KangBiQuan, Beijing, China) containing 5-10 microgram of PD-L1/Fc. Two weeks after the $2^{nd}$ immunization, the mice sera were collected and evaluated for PD-L1 binding by ELISA and FACS. An example of such assay results were shown in Table 1 and Table 2. The mice with high anti-PD-L1 binding titers in sera were selected and boosted intraperitoneally with 50 micrograms of PD-L1/Fc in PBS. Three days after boosting, the splenocytes were isolated and fused with the murine myeloma cell line, SP2/0 (ATCC), using standard techniques (Mechetner et. al. 2007 Methods Mol Biol 378:1-13) with some modification.

TABLE 1

Binding activities of serial diluted mice sera to PD-L1/His protein in ELISA assay

| Mouse sera dilution factor | ELISA binding (OD450) | | |
|---|---|---|---|
| | Immunized mouse #1 | Immunized mouse #2 | Immunized mouse #3 |
| 1:300 | 5.749 | 5.546 | 5.586 |
| 1:900 | 5.651 | 4.978 | 4.453 |
| 1:8100 | 4.166 | 2.853 | 2.137 |
| 1:24300 | 2.641 | 1.539 | 0.896 |
| 1:72900 | 1.287 | 0.498 | 0.212 |
| 1:218700 | 0.282 | 0.065 | 0.056 |

TABLE 2

Binding activities of serial diluted mice sera to HEK293/PD-L1 cells in FACS assay

| Mouse sera dilution factor | FACS PD-L1ng (MFI) | | |
|---|---|---|---|
| | Immunized mouse #1 | Immunized mouse #2 | Immunized mouse #3 |
| 1:300 | 2657.7 | 1675.8 | 1499 |
| 1:900 | 1485.9 | 681.6 | 560.5 |
| 1:8100 | 355.6 | 274.7 | 175.7 |
| 1:24300 | 73.9 | 107.1 | 54.9 |
| 1:72900 | 33.9 | 26.9 | 19.8 |

Assess PD-L1 Binding Activity of Murine mAbs by ELISA and FACS

The supernatants of hybridoma clones were initially screened for PD-L1 binding activities by a modified ELISA assay (Flanagan 2007 Methods Mol Biol 378:33-52). Briefly, 50-200 nanograms of PD-L1/His were diluted in 50 microliters of PBS and coated in each well of 96-well ELISA plates (JinCanHua, Shenzhen, China). After blocking with 3% bovine serum albumin in TBST (20 mM Tris, 150 mM NaCl, 0.05% Tween20, pH7.5) and incubating with culture supernatants of hybridoma clones, the HRP-conjugated horse anti-mouse IgG antibody (Cat. No. 7076S, Cell Signaling Technology) and tetramethylbenzidine (TMB) (Cat. No. PA107-01, TianGen, Beijing, China) were used to detect binding signals by a plate reader (PHREAstar, BMG Labtech, Germany) as light absorbance at 450 nm. The ELISA-positive clones were further verified by fluorescence-activated cell sorting (FACS). PD-L1 expression cells, HEK293/PD-L1 ($10^5$ cells/well), were incubated with supernatants from hybridoma clones in V-bottom 96-well plates (Cat. No. 3897, Corning). The cell surface bound PD-L1 antibodies were detected with Dylight 649-conjugated goat anti-mouse IgG antibody (Cat. No. 405312, Biolegend, San Diego, Calif., USA) and cell fluorescence was monitored in a Guava EasyCyte 8HT flow cytometer (Millipore, USA).

The hybridoma clones that were positive in both ELISA and FACS assays were then tested in human immune cell-based functional assays to identify antibodies with good functional activities. The hybridoma clones with positive functional activities were further subcloned and characterized.

Subcloning and Hybridoma Cell Adaption to Serum Free or Low Serum Medium

The positive hybridoma clones from primary screening through ELISA, FACS and functional assays were subcloned by limiting dilution. Three subclones from each original clone were selected and confirmed in FACS and functional assays. The subclones selected through functional assays were defined as monoclonal antibody. The top subclones were adapted to grow in the CDM4MAB medium (Cat. No. SH30801.02, Hyclone) with 0-3% fetal bovine serum for purification and further characterizations.

Assesses of Binding Activities of Purified Antibodies

Hybridoma cells or 293-F cells transiently transfected with an antibody expression plasmid (Cat. No. R79007, Invitrogen) was cultured either in CDM4MAb medium (Cat. No. SH30801.02, Hyclone) or in Freestyle™ 293 Expression medium (Cat. No. 12338018, Invitrogen), and incubated in a CO2 incubator for 5 to 7 days at 37° C. The conditioned medium was collected through centrifugation at 10,000 g for 30 minutes to remove all cells and cell debris, and filtrated through a 0.22 μm membrane before purification. Murine or recombinant antibodies containing supernatants were applied and bound to a Protein A column (Cat. No. 17127901, GE Life Sciences) following the manufacturer's guide, washed with PBS, eluted in an acidic buffer (pH3.5) containing 20 mM citrate, 150 mM NaCl. The eluted materials were neutralized with 1M Tris pH8.0. The procedure usually yielded antibodies with purity above 90%. The Protein A-affinity purified antibodies were either dialyzed against PBS or further purified using a HiLoad 16/60 Superdex200 column (Cat. No. 17531801, GE Life Sciences) to remove aggregates. Protein concentrations were determined by measuring absorbance at 280 nm or by Bradford assay (Cat. No. 1856210, Thermo Scientific, Rockford, Ill., USA) using bovine IgG reference standard (Cat. No. 23212, Thermo Scientific). The final antibody preparations were stored in aliquots in −80° C. freezer.

Figure 2A:
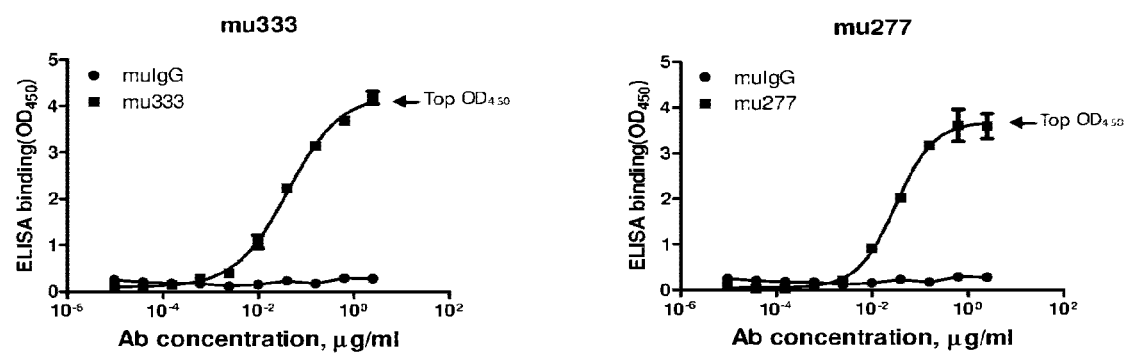
FIG. 2A and FIG. 2B: Dose-dependent binding to the purified human PD-L1/His in ELISA (FIG. 2A) or to cell surface expressed PD-L1 in FACS (FIG. 2B) by murine mAbs. The murine mAbs and mouse IgG as negative control were indicated at top-left corner of each figure.
Figure 2B:
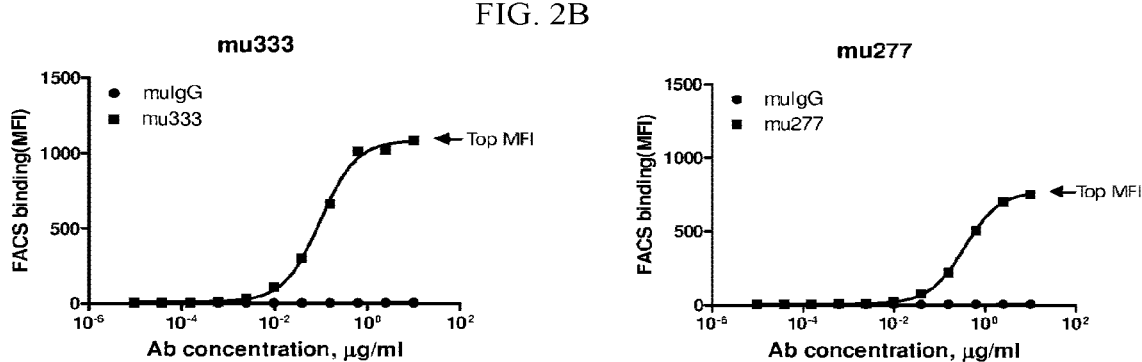

The binding activities of the purified monoclonal antibodies were evaluated in ELISA and FACS assays as described in previous sections. The dose-dependent binding curves in ELISA and FACS were used to compare mAb potency. The results of two representative murine mAbs were illustrated in FIG. 2A and FIG. 2B and Table 3. Murine mAb333 (mu333) has a dose-dependent binding activities with $EC_{50}$ (effective concentration at 50% activity) of 0.036 µg/mL and 0.099 µg/mL, respectively, in ELISA and FACS assays. Mu277 has a similar binding activity to Mu333 in ELISA ($EC_{50}$=0.031 µg/mL), but a lower binding activity in FACS ($EC_{50}$=0.371 µg/mL). In contrast, control mouse IgG (muIgG) had no bindings to PD-L1 in both assays.

TABLE 3

Dose-dependent binding of anti-PD-L1 mAbs in ELISA and FACS assays

| Antibody | ELISA $EC_{50}$ (µg/mL) | Top OD450 | FACS $EC_{50}$ (µg/mL) | Top MFI |
|---|---|---|---|---|
| mu333 | 0.036 | 4.026 | 0.099 | 1101 |
| mu277 | 0.031 | 3.730 | 0.371 | 793 |
| muIgG | N/A | N/A | N/A | N/A |

OD450: Absorbance signal at 450 nm in ELISA assay;
MFI: Mean fluorescence intensity from FACS analysis
N/A: Not applicable Example 2. Functional Activities of Anti-PD-L1 Antibodies Generation of Stable Cell Lines The stable cell lines for human T cell-based functional assays were essentially the same as described in U.S. Pat. No. 8,735,553. Briefly, a fusion protein expression plasmid, OS8, was generated containing a scFv of anti-human CD3 mAb OKT3 and a C-terminal domain of mouse CD8a which included transmembrane and cytoplasmic domains. OS8 could function as a membrane anchored T cell engager that directly activates T-cell receptor (TCR). A stable cell line that co-expresses both OS8 and PD-L1 was generated by co-transfection of two expression constructs in HEK293 cells followed by hygromycin or G418 selection for 10-14 days. This cell line was named as HEK293/OS8/PD-L1. Similarly, a human T-cell line, HuT78/PD-1, was generated that expresses human PD-1. And a reverse signaling human T-cell line, HuT78/P3Z, was generated by stable transfection with a chimeric PD-1 expression construct (named as P3Z) made by fusing the extracellular and transmembrane domains of human PD-1 to the cytoplasmic region of human CD3 chain. In this way, P3Z encoded a membrane bound receptor that would activate T cells upon ligation with PD-1 ligand (PD-L1 or PD-L2). Cell lines were cloned by limiting dilution as described previously (Fuller 2001 Curr Protoc Mol Biol, Chap 11, unit PD-L1.

Determination of PD-L1 Antibody Functions by IL-2 Release in HuT78/PD-1 Cells

To determine whether anti-PD-L1 antibodies can block the PD-1 signaling induced by PD-L1, HEK293/OS8/PD-L1 cells pre-incubated with anti-PD-L1 mAbs for 15 minutes prior to co-culture with HuT78/PD-1 cells (1-3×104 per well) in a flat bottom plate fed with 200 µl of RPMI1640 growth medium per well at 37° C. After 16-18 hours of co-culture, supernatants were collected. IL-2 was assayed by ELISA using human IL-2 Ready-Set-Go! ELISA kits (Cat. No. 88-7025, eBiosciences, San Diego, Calif.). In PD-L1-PD-1, blockade of PDanti-PD-L1 signaling with anti-PD-L1 antibodies resulted in enhanced TCR signaling and IL-2 production.

As shown in Table 4, supernatants of ELISA and FACS-binding positive hybridoma clones were screened in this functional assay. Although all the tested clones bound to PD-L1 in ELISA and FACS assays, only a few of them could block PD-L1-PD-1 signaling and resulted in increase of IL-2 production. The remaining clones resulted in either no increase or very little increase of IL-2 production compared to the negative control with fresh medium only. In this experiment, an OD450 reading cut off was set at 2.5, i.e. clones that stimulated 1L-2 production above this level were considered to have antagonist functions anti-PD-L1. A reference anti-PD-L1 mAb (named Y1) was synthesized based on the variable regions of the published data (US 2010/0203056 A1), and both human and mouse format of Y1 antibodies were generated by fusing Y1 variable regions with mouse or human IgG1 k constant regions to generate Y1-muIgG1 or Y1-huIgG1, respectively (collectively termed asY1-hIgG1). Y1-muIgG1's function was also confirmed in this assay.

TABLE 4

Functional screening of anti-PD-L1 hybridoma clones in HEK293/OS8/PD-L1 coculture with HuT78/PD-1*

| Sample/Clone ID | OD450 in IL-2 ELISA assay |
|---|---|
| negative control: medium only | 1.30 ± 0.06 |
| mu31 | 1.28 ± 0.03 |
| mu32 | 1.33 ± 0.02 |
| mu33 | 1.24 ± 0.01 |
| mu34 | 1.19 ± 0.12 |
| mu35 | 1.27 ± 0.02 |
| mu36 | 2.95 ± 0.22 |
| mu37 | 3.10 ± 0.11 |
| mu38 | 1.33 ± 0.44 |
| mu39 | 2.94 ± 0.45 |
| mu310 | 1.90 ± 0.01 |
| mu311 | 1.38 ± 0.08 |
| mu312 | 1.40 ± 0.07 |
| mu313 | 1.49 ± 0.07 |
| mu314 | 1.26 ± 0.01 |
| mu315 | 1.36 ± 0.11 |
| mu316 | 1.23 ± 0.12 |
| mu317 | 1.72 ± 0.12 |
| mu318 | 2.21 ± 0.06 |
| mu319 | 1.38 ± 0.05 |
| mu320 | 1.32 ± 0.10 |
| mu321 | 1.33 ± 0.02 |
| mu322 | 1.34 ± 0.10 |
| mu323 | 1.52 ± 0.06 |
| mu324 | 3.09 ± 0.11 |
| mu325 | 1.44 ± 0.02 |
| mu326 | 1.35 ± 0.19 |

TABLE 4-continued

Functional screening of anti-PD-L1 hybridoma clones
in HEK293/OS8/PD-L1 coculture with HuT78/PD-1*

| Sample/Clone ID | OD450 in IL-2 ELISA assay |
|---|---|
| mu327 | 2.55 ± 0.36 |
| mu328 | 3.10 ± 0.47 |
| mu329 | 1.43 ± 0.07 |
| mu330 | 1.46 ± 0.11 |
| mu331 | 1.37 ± 0.07 |
| mu332 | 1.44 ± 0.05 |
| mu333 | 3.01 ± 0.23 |
| mu334 | 3.22 ± 0.09 |
| mu335 | 3.03 ± 0.15 |
| mu336 | 3.12 ± 0.24 |
| mu337 | 1.28 ± 0.06 |
| mu338 | 1.34 ± 0.05 |

*Funcanti-PD-L1nes were showed in bold

Figure 3A:
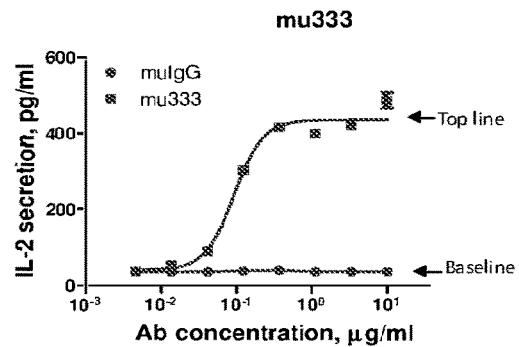
FIG. 3A and FIG. 3B: Dose-dependent response curves of murine anti-PD-L1 mAb-induced IL-2 secretion in HuT78/PD-1 cells after co-culture with HEK293/OS8/PD-L1 cells. Baseline: Average IL-2 release induced by mouse IgG (mIgG) at all tested concentrations. Each represents average of duplicate data points. Top line: Highest IL-2 release based on regression calculation by Prizm.
Figure 3B:
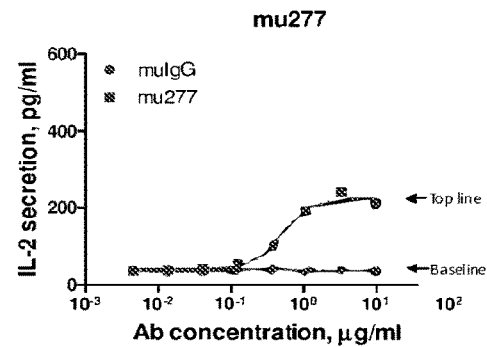
Figure 4A:
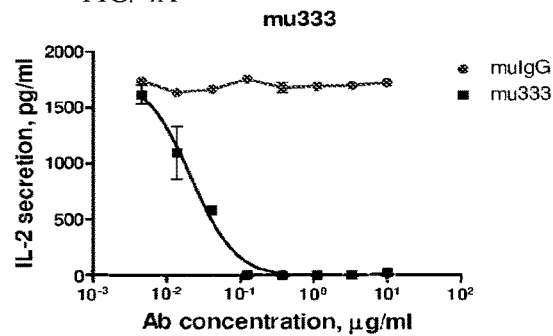
FIG. 4A and FIG. 4B: Dose-dependent response curves of murine anti-PD-L1 mAb-inhibited IL-2 secretion in HuT78/P3Z cells after co-culture with HEK293/PD-L1 cells. Engagement of PD-L1 and P3Z chimeric receptor leads to activation of P3Z chimeric receptor and IL-2 secretion.
Figure 4B:
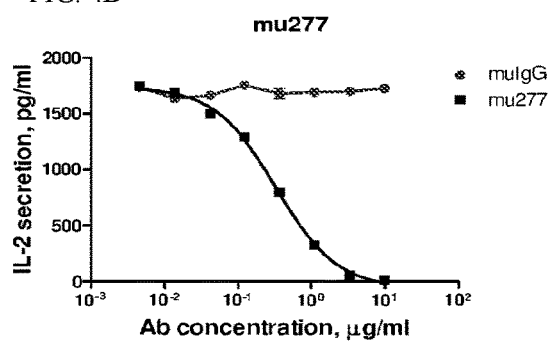

The purified murine anti-PD-L1 mAbs were compared in the same assay for quantitative assessments of the blocking activities. FIG. 3A and FIG. 3B: murine-anti-PD-L1 response curves of the representative murine-anti-PD-L1 mAbs. Table 5 summarized the $EC_{50}$ and the maximum IL-2 concentration these mAPD-L1-PD-induce. Mu333 was a potent antagonist of the PD-L1-PD-1 signaling, and induced significant IL-2 production with a very low $EC_{50}$. In contrast, one of the mAbs, mu277, had much weaker blocking activity than mu333, judged by the dose dependent response curve and the parameters of top line signal read-out and $EC_{50}$. As the negative control, muIgG could not block PD-L1/PD-1 signaling and stimulate IL-2 production.

TABLE 5

IL-2 release induced by anti-PD-L1 mAbs in HuT78/PD-1
cells co-cultured with HEK293/OS8/PD-L1 cells

| Antibody | Baseline (pg/mL) | Top line (pg/mL) | $EC_{50}$ (µg/mL) |
|---|---|---|---|
| mu333 | 37 | 436 | 0.092 |
| mu277 | 37 | 225 | 0.510 |
| muIgG | 37 | N/A | N/A |

Baseline: Average IL-2 release induced by muIgG at all tested concentrations, see FIG. 3A
Top line: Highest IL-2 release(pg/ml) based on regression calculation by Prizm Software, see FIG. 3A
N/A: Not applicable Determination of PD-L1 Antibody Functions by Reverse Signaling of IL-2 Release in HuT78/P3Z Cells In HuT78/P3Z cells, PD-1 mediated TCR signaling is reversed by design as described in the previous sections. In this assay, HEK293/PD-L1 cells were pre-incubated with purified PD-L1 antibodies for 15 minutes prior to co-culture with HuT78/P3Z cells in 96-well flat bottom plates at 37° C. After 16-18 hours of co-culture, supernatants were collected and IL-2 production was assayed by ELISA as described above.

Inhibitory activity of murine anti-PD-L1 mAbs was detected directly correlated to the decrease of IL-2 release in dose-dependent fashion. Consistent with the results shown above, mu333 had potent activities inhibiting TL-2 secretion by preventing PD-L1 engagement on P3Z chimeric receptor on HuT78 cells. As shown in Table 6 and FIG. 6A and FIG. 6B, mu333 was much more potent than mu277 in terms of $IC_{50}$ (the concentration of mAb at 50% inhibition of the maximum activity), consistent with the above results obtained with regular signaling in T-cell. The negative control, muIgG, could not inhibit PD-L1/P3Z induced IL-2 production.

TABLE 6

Inhibition of IL-2 secretion by anti-PD-L1 mAbs in
HuT78/P3Z cells co-cultured with HEK293/PD-L1 cells

| Antibody | $IC_{50}$ (µg/mL) | Maximum inhibition* |
|---|---|---|
| mu333 | 0.021 | 100% |
| mu277 | 0.331 | 100% |
| muIgG | N/A | N/A |

*Maximum inhibition was calculated as percentage (%) of inhibition with anti-PD-L1 mAbs added to the highest concentratPD-L10 µg/ml) in culture Competitive Inhibition of PD-1 Binding to Cell Surface-Expressed PD-L1

Figure 5A:
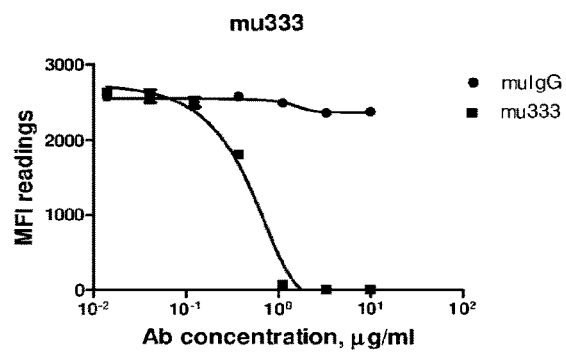
FIG. 5A and FIG. 5B: Dose-dependent competition curves of murine anti-PD-L1 mAbs against biotin-conjugated PD-1/Fc. Fixed amount of biotin-PD-1-ECD/Fc was mixed with increasing concentrations of anti-PD-L1 mAbs indicated in x-axis. Mean fluorescence intensity (MFI) analyzed by FACS was shown in y-axis. Mouse Gig (mug) was used as a negative control.
Figure 5B:
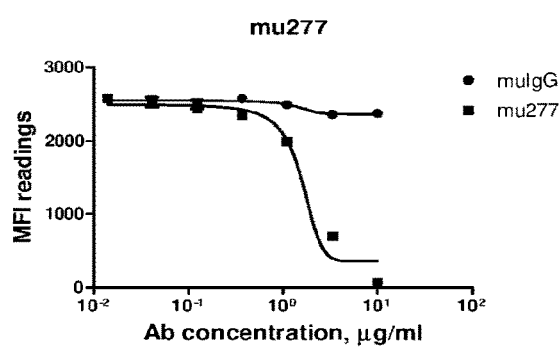

To determine whether anti-PD-L1 antibodies can compete with PD-1 binding to PD-L1, HEK293/PD-L1 cells (1×10$^5$ cells per well) were incubated with the mixture of PD-L1 antibodies and biotin-conjugated PD-1/Fc fusion protein in V-bottom 96-well plate. Biotinylation of PD-1/Fc was done using the EZ-Link Sulfo-NHS-LC-Biotin reagent according to manufacturer's instruction (Cat. No. 21327, Thermo Sci). Inhibition of PD-L1 and PD-1/Fc interaction by antibodies was assayed (Guava easyCyte 8HT Flow Cytometer, Millipore, USA) by mean fluorescence intensity (MFI) readout probed with Streptavidin-APC. Using this method, we evaluated functional strength of anti-PD-L1 mAbs. As shown in FIG. 5A and FIG. 5B and Table 7, the murine mAbs competitively bind to PD-L1, inhibiting WIFI readout elicited by Biotin-PD-1/Fc binding to cell surface PD-L1 in the FACS assay. Mu333 showed better inhibitory efficacy with an IC50 of 0.463 µg/mL, compared to an $IC_{50}$ of 2.172 µg/mL for mu277. In contrast, control antibody, murine IgG, had no such inhibitory effect (FIG. 5A, 5B).

TABLE 7

Inhibition of PD-1 binding to PD-L1 on HEK293 cells

| Antibody | $IC_{50}$ (µg/mL) | Maximum inhibition |
|---|---|---|
| mu333 | 0.463 | 100% |
| mu277 | 2.172 | 98% |
| muIgG | N/A | N/A |

Maximum inhibition was calculated as percentage (%) of inhibition with anti-PD-L1 mAbs added to the highest concentration(10 µg/ml);
N/A: not applicable Competitive Inhibition of CD80 Binding to Cell Surface PD-L1

Figure 6A:
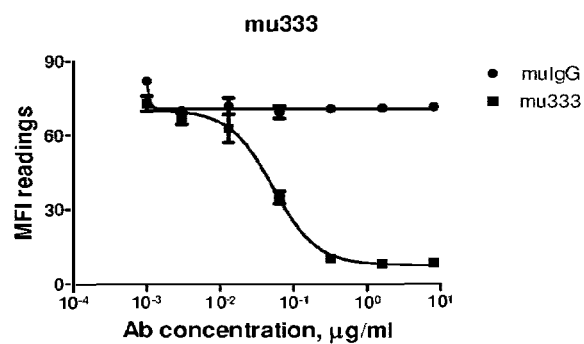
FIG. 6A and FIG. 6B: Dose-dependent competition curves of murine anti-PD-L1 mAbs against biotin-conjugated CD80/Fc. Fixed amount of biotin-CD80-ECD/Fc was mixed with increasing amount of anti-PD-L1 mAbs indicated in x-axis. Mean fluorescence intensity (MFI) analyzed by FACS was shown in y-axis. Mouse IgG (muIgG) was used as a negative control.
Figure 6B:
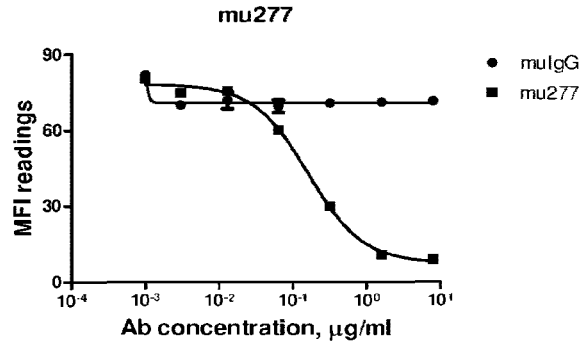

Besides interaction with PD-1, PD-L1 also binds to another B7 family protein, B7-1 or alternatively named as CD80 (Butte M. J. 2007 Immunity 27:111-122). To determine whether the anti-PD-L1 antibodies compete against the binding of CD80 (NCBI accession: NP_005182.1) to PD-L1, HEK293/PD-L1 cells were incubated with the mixture of PD-L1 antibodies and biotin-conjugated CD80/Fc fusion protein. In this assay, blockade of biotin-CD80/Fc binding to PD-L1 by anti-PD-L1 antibodies resulted in decreased binding signals (MFI readings). As shown in FIG. 6A and Table 8, mu333 competed off the binding of CD80 to PD-L1 with 100% of max inhibition and very low $IC_{50}$ (0.052 µg/mL), which compared to the $IC_{50}$ of 0.162 µg/mL for mu277. In contrast, murine IgG had no such competition effect (FIG. 6A, FIG. 6B).

TABLE 8

Inhibition of CD80 binding to cell surface expressed PD-L1 on HEK293 cells

| Antibody | IC$_{50}$ (μg/mL) | Maximum inhibition |
|---|---|---|
| mu333 | 0.052 | 100% |
| mu277 | 0.162 | 99% |
| muIgG | N/A | N/A |

Maximum inhibition was calculated as percentage (%) of inhibition with anti-PD-L1 mAbs added to the highest concentration(10 μg/ml) in culture;
N/A: not applicable

Example 3. Sequence Analysis of Murine Anti-PD-L1 Antibodies

Cloning and sequencing of variable regions from the selected murine hybridoma clones were done based on commonly used methods with some modifications (Kontermann and Dubel, 2010 Antibody Engineering, Vol 1:3-14). Briefly, hybridoma cells were harvested, washed with PBS and collected by centrifugation at 1500 rpm in a swing bucket rotor. Total cellular RNA was isolated using Ultrapure RNA kit (Cat. No. CW0581, CW Biotech, Beijing, China) following the manufacturer's protocol.

The 1$^{st}$ strand cDNA was synthesized using reverse transcriptase (Cat. No. AH301-02, TransGen, Beijing, China). PCR amplification of heavy chain (Vh) and light chain variable region (Vic) of murine mAb was performed using PCR reagent kit (Cat. No. AP221-12, TransGen, Beijing, China) and a set of primers specific for cloning of murine Vh and Vic as described (Brocks 2001 Mol Med 7:461-469). The PCR products were subcloned into the pEASY-Blunt cloning vector (Cat. No. CB101-02, TransGen) and subsequently sequenced by Genewiz (Beijing, China). The amino acid sequences of Vh and Vk were deduced from the DNA sequencing results.

The murine mAbs were analyzed by comparison of sequence homology, and grouped based on both sequence homology and epitope-mapping results (see Example 7). Complementary determinant regions (CDRs) were defined based on the Kabat (Wu and Kabat 1970 J. Exp. Med. 132:211-250) and IMGT (Lefranc 1999 Nucleic Acids Research 27:209-212) system by sequence annotation and by internet-based sequence analysis (www.imgt.org/IMGT_vquest/share/textes/index.html). Table 9 listed the CDRs of mu333 (SEQ. NO. 5-14), based on the definitions of Kabat and IMGT systems.

Example 4. Humanization of the Murine Anti-Human PD-L1 mAb

Simulation of 3D Structure of Murine mAb

The three dimensional structures were simulated for variable domain of mu333 in order to identify framework residues that might be important for supporting CDR loop structures. Potentially important framework residues were kept as the original murine residues in the first round antibody humanization. The previously established structural modeling method for antibodies (Morea et al. Methods 2000 20:267-279) was adopted to simulate 3D structure of anti-PD-L1 mAb mu333 based on the known canonical structures of antibodies (Al-Lazikani et al. 1997 Journal of Molecular Biology 273:927-948). Briefly, the sequence of each variable domain (Vk and Vh) of mu333 was blasted in the PDB database (Protein Data Bank, blast.ncbi.nlm.nib.gov/) to identify the most homologous antibody sequence with known high resolution structure (resolution less than 2.5 angstrom). Selected structure templates for modeling mu333 (listed in Table 10) had the same classes of canonical loop structures in L-CDR1, L-CDR2, L-CDR3, H-CDR1, and H-CDR2 to the mu333 to be modeled. As the templates for Vκ and Vh came from different immunoglobulins, they were packed together by a least-squares fit of the main chain atoms to form a hybrid structure of Vk-Vh interface residues, which was used as the templates for structural homology modeling by Swiss-model program (Kiefer et al. 2009 Nucleic Acids Research 37, D387-D392). Certain side chain conformation was adjusted while the main chain conformations were retained. At the sites where the parental structure and the modeled structure had the same residue, the side chain conformation was retained. At sites where the residues were different, side chain conformations were modeled on the basis of template structure, rotamer libraries and packing considerations. After homology modeling, PLOP program (Jacobson et al. 2002 Journal of Physical Chemistry 106:11673-11680) was used to refine the homology models to minimize all-atom energy and optimize Vk and Vh interface. This step was performed to improve the stereochemistry, especially in those regions where segments of structures coining from different antibodies had been joined together. The modeled 3D structure of mu333 variable domain was used to guide the structure-based humanization and engineering process.

TABLE 9

CDR sequences of mu333

| MAbs | CDR1 | SEQ ID NO | CDR2 | SEQ ID NO | CDR3 | SEQ ID NO |
|---|---|---|---|---|---|---|
| mu333, Vh | GFSLTSYGVH | 9 | VIWAGGSTNYNSALMS | 10 | AKPYGNSAMDY | 11 |
| mu333, Vk | KASQDVGIVVA | 12 | WASIRHT | 13 | QQYSNYPLYT | 14 |

Note:
CDR sequences in bold face are defined based on Kabat system; CDR sequences underlined are defined based on IMGT system.

TABLE 10

Structure templates used in antibody structure simulation

| Antibody chain | PDB code of template structure | Sequence identity | Sequence similarity |
|---|---|---|---|
| mu333 Vk | 1H8N | 92% | 94% |
| mu333 Vh | 3VFG | 88% | 91% |

MAb Humanization and Engineering

For humanization of the anti-PD-L1 mAb, human germline IgG genes were searched for sequences that sha1MGTigh degree of homology to the cDNA sequences of mu333 variable regions NCB1 lasting the human immunoglobulin gene database in IMGT (www.imgt.org/IMGT_v-quest/share/textes/index.html) and NCBI (www.ncbi.nlm.nih.gov/igblast/) websites. The human IGVH and IGVK genes that are present in human antibody repertoires with high frequency (Glanville 2009 PNAS 106:20216-20221) and are highly homologous to mu333 were selected as the templates for humanization.

Humanization was carried out by CDR-grafting (Methods in Molecular Biology, Vol 248: Antibody Engineering, Methods and Protocols, Humana Press) and the humanization antibodies (hu333s) were engineered as the human Fab format using an in-house developed expression vector. In the initial round of humanization, mutations from murine to human amino acid residues in framework regions were guided by the simulated 3D structure, and the murine framework residues of structural importance for supporting the canonical structures of CDRs were retained in the $1^{st}$ version of humanization antibody 333 (hu333-1A, SEQ. NO. 15-16). Specifically, CDRs of mu333 Vk were grafted into the framework of human germline variable gene IGVK1-5, and no murine framework residues were retained (SEQ NO 16). CDRs of mu333 Vh were grafted into the framework of human germline variable gene IGVH3-7, with 4 murine framework residues retained, $V_{24}$, $L_{67}$, $K_{71}$ and $V_{78}$ (SEQ NO 15). All grafted CDRs were based on the Kabat's CDR definition in hu333-1A (Table 9 and SEQ. NO. 15-16). In the following hu333 variants, only the N-terminal half of Kabat H-CDR2 was grafted, as only the N-terminal half was considered to be important for antigen binding according to the simulated 3D structure (Table 14).

Hu333-1A were constructed as human Fab format using in-house developed expression vectors that contain human IgG CH-1 and constant region of kappa chain, respectively, with easy adapting subcloning sites. The hu333-1A joined IgG2a-CH1 was tagged at C-terminus with a 8xHis peptide to facilitate purification. The C232S and C233S (Kabat residue numbering, Kabat et al. Sequence of proteins of immunologic interest, $5^{th}$ ed Bethesda, Md., NIH 1991) mutations were introduced in the IgG2 heavy chain to prevent disulfide bond exchange and stabilize human IgG2 in the IgG2a conformation (Lightle et al. 2010 Protein Sci 19(4): 753-762). Both constructs contained a signal peptide upstream of the Fab mature sequences. Secreted expression of hu333-1A Fab was achieved by co-transfection of the above two constructs into 293-F cells and cultured for 6-7 days before harvest. His8-tagged Fabs were purified from expression culture supernatants using a Ni-sepharose Fast Flow column (Cat. No. 17531801, GE Life Sciences) followed by size exclusion chromatography using a HiLoad 16/60 Superdex200 column (Cat. No. 17106901, GE Life Sciences). The purified Fabs were concentrated to 0.5-5 mg/mL in PBS and stored in aliquots in −80° C. freezer.

For affinity determinations of anti-PD-L1 Fabs, SPR assays were performed using BIAcore™ T-200 (GE Life Sciences). Briefly, human PD-L1/His was coupled to an activated CMS biosensor chip (Cat. No. BR100530, GE Life Sciences) to achieve approximately 100-200 response units (RU), followed by blocking un-reacted groups with 1M ethanolamine. A serial dilutions of 0.12 nM to 90 nM Fab samples were injected, mixed into the SPR running buffer (10 mM HEPES, 150 mM NaCl, 0.05% Tween20, pH7.4) at 30 μL/minute, and binding responses on human PD-L1/His were calculated by subtracting of RU from a blank flow-cell. Association rates ($k_{on}$) and dissociation rates ($k_{off}$) were calculated using the one-to-one Langmuir binding model (BIA Evaluation Software, GE Life Sciences). The equilibrium dissociation constant ($K_d$) was calculated as the ratio $k_{off}/k_{on}$.

Functional activities of hu333 Fabs were confirmed in PD-1 competition assays described in previous sections. Data from SPR measurement and functional assays were summarized in Table 11. Hu333-1A Fab had very high affinity ($K_d$=9.88 pM) to PD-L1 indicated by a fast $k_{on}$ ($1.61 \times 10^6$ $M^{-1}s^{-1}$) and very slow $k_{off}$ ($1.59 \times 10^{-5}$ $s^{-1}$). It was observed that there was very slow or virtually no dissociations of hu333-1A Fab from the coated PD-L1 during the 5-15 minutes of dissociation time in this experiment. It was apparent that the affinity of hu333-1A Fab to PD-L1 was close to the detection limit of the SPR technology. Such high affinity of hu333-1A Fab was consistent with the high potencies in all functional assays tested (Table 11).

Following on hu333-1A, we made individual mutations converting the four murine residues in framework region of Vh to corresponding human germline residues, respectively. At same time In order to further improve humanization level, we also changed the C-terminal part of H-CDR2 (Kabat's definition) from murine sequence to corresponding human germline residues (Table 14, hu333-2B). Specifications of the four humanization Fabs were hu333-2A ($V_{24}A$ in Vh), hu333-2B ($L_{67}F$ in Vh), hu333-2C ($K_{71}R$ in Vh) and hu333-2D ($V_{78}L$ in Vh), which are illustrated in Table 13 with H-CDR2 changes. All humanization mutations were made using primers containing mutations at specific positions and a site directed mutagenesis kit (Cat. No. FM111-02, TransGen, Beijing, China). The desired mutations were verified by sequencing analyses. These hu333 Fabs were expressed, purified and tested in binding and functional assays as described previously. Comparing to hu333-1A, hu333-2A, hu333-2C and hu333-2D had significantly reduced binding affinities and functionalities. Only hu333-2B (SEQ. NO. 16 and 17) had similar binding and functional activities to hu333-1A (Table 11). Taken together, hu333-2B (SEQ. NO. 16 and 17) reached a high level of humanization in the framework regions while maintained potent binding affinity and functional activities.

TABLE 11

Comparison of hu333-1A and hu333-2B Fabs by SPR and functional assays

| Assay/Parameter | | hu333-1A Fab | hu333-2B Fab |
|---|---|---|---|
| BiaCore SPR | $k_{on}$ ($M^{-1}s^{-1}$) | $1.61 \times 10^6$ | $1.36 \times 10^6$ |
| | $k_{off}$ ($S^{-1}$) * | $1.59 \times 10^{-5}$ | $2.09 \times 10^{-6}$ |
| | $K_d$ (pM) * | 9.88 | 1.54 |
| PD-1 binding competition (FACS) | $IC_{50}$(μg/ml) | 0.057 | 0.062 |
| | Max inhibition | 100% | 100% |
| CD80 binding | $IC_{50}$(μg/ml) | 0.049 | 0.055 |

TABLE 11-continued

Comparison of hu333-1A and hu333-2B
Fabs by SPR and functional assays

| Assay/Parameter | | hu333-1A Fab | hu333-2B Fab |
|---|---|---|---|
| competition (FACS) | Max inhibition | 99% | 99% |
| IL-2 release in HuT78/PD-1[#] | $EC_{50}$ (μg/ml) | 0.066 | 0.054 |
| | Top line (pg/ml) | 1369 | 1436 |
| IL-2 release in HuT78/P3Z[§] | $IC_{50}$ (μg/ml) | 0.012 | 0.011 |
| | Max inhibition | 100% | 100% |

\* $K_{off}$ might be slow to be accurately measured during the 5-15 min dissociation time in the SPR experiment. Therefore, the affinity might be too strong to be accurately determined using current instrument/experiment setting
[#]IL-2 release in HuT78/PD-1: IL-2 release induced by the Fabs in HuT78/PD-1 cells co-cultured with HEK293/OS8/PD-L1 cells
[§]IL-2 release in HuT78/P3Z: IL-2 release induced by the Fabs in HuT78/P3Z cells co-cultured with HEK293/PD-L1 cells To explore the best possible Vh and Vk sequence composition for hu333 that could be used as therapeutic antibody in human, we further engineered the hu333 by introducing mutations in CDRs and framework regions in considerations of the antibody's molecular properties, such as physiochemical stabilities, amino acid compositions, projected isoelectronic points (pIs), expression level, antibody-dependent cell-mediated cytotoxicity (ADCC) and complement-dependent cytotoxicity (CDC) while maintaining functional activities.

Deamination site $NS_{76-77}$ in Vh of hu333-1A was mutated to $NT_{76-77}$ to generate hu333-3A2 (SEQ. NO. 18 and 23). V60 of hu333-3A2-Vh was mutated to V60A, which is consistent to the consensus sequences of major human IGVH3 genes with reduced a surface-exposure of hydrophobicity. This mutant construct was given the code name hu333-3C2 (SEQ. NO. 19 and 23). Another deamination site $NS_{73-74}$ was mutated to $TS_{73-74}$ on the template of hu333-3C2, which is also consistent to the consensus sequences of major human IGVH3 genes. The latter one was named as hu333-3H2 (SEQ. NO. 20 and 23). As summarized in Table 12, hu333-3A2, hu333-3C2 and hu333-3H2 all retained the potent functional activity, only with slight variations in binding affinity. On the other hand, these engineered hu333 variants have better projected physiochemical properties.

To eliminate the last deamidation site in the CDR3 of Vh, we mutated $NS_{101-102}$ $TS_{101-102}$ on the templates of hu333-3A2 and hu333-3H2, respectively. The resulting humanization mAbs were constructed in human IgG1 Fab format, named as hu333-4A2 (SEQ. NO. 21 and 23) and hu333-4B2 (SEQ. NO. 22 and 23). The results from binding and functional assays indicated both hu333-4A2 and hu333-4B2 were very similar in affinity and functional activities such as blocking the PD-L1 binding to its targets (PD-1 and CD80) and inhibiting the PD-L1 and PD-1 mediated downstream signaling (Table 13 and Table 14). Several mutations made in the processes including hu333-3B2, -3D2, -3E2, -3G2 and -312 were dropped from further development for various considerations. The CDRs of the above mAbs were compared to those of mu333 were shown in Table 14.

TABLE 13

Comparison of hu333-4A2 and hu333-4B2
Fabs by SPR and functional assays

| Assay/Parameter | | hu333-4A2 Fab | hu333-4B2 Fab |
|---|---|---|---|
| BiaCore SPR | $k_{on}$ (M$^{-1}$s$^{-1}$) | 3.88 × 10$^6$ | 3.78 × 10$^6$ |
| | $k_{off}$ (S$^{-1}$) * | 1.03 × 10$^{-5}$ | 1.32 × 10$^{-5}$ |
| | $K_d$ (pM) * | 2.65 | 3.50 |
| PD-1 binding competition (FACS) | $IC_{50}$ (μg/ml) | 0.050 | 0.053 |
| | Max inhibition | 100% | 100% |
| CD80 binding competition (FACS) | $IC_{50}$ (μg/ml) | 0.045 | 0.062 |
| | Max inhibition | 100% | 100% |
| IL-2 release in HuT78/PD-1[#] | $EC_{50}$ (μL-2) | 0.050 | 0.058 |
| | Top line (pg/ml) | 227.5 | 215.5 |
| IL-2 release in HuT78/P3Z[§] | $IC_{50}$ (μg/ml) | 0.005 | 0.016 |
| | Max inhibition | 100% | 100% |

\* $K_{off}$ might be too slow to be accurately measured during the 5-15 min dissociation time in the SPR experiment. Therefore, the affinity might be too strong to be accurately determined using current instrument/experiment setting.
[#]IL-2 release in HuT78/PD-1: IL-2 release induced by the Fabs in HuT78/PD-1 cells co-cultured with HEK293/OS8/PD-L1 cells
[§]IL-2 release in HuT78/P3Z: IL-2 release induced by the Fabs in HuT78/P3Z cells co-cultured with HEK293/PD-L1 cells

TABLE 12

Comparison of hu333-3A2 and hu333-3C2 and
hu333-3H2 Fabs by SPR and functional assays

| Assay/Parameter | | hu333-3A2 Fab | hu333-3C2 Fab | hu333-3H2 Fab |
|---|---|---|---|---|
| BiaCore SPR | $k_{on}$ (M$^{-1}$s$^{-1}$) | 1.28 × 10$^6$ | 1.42 × 10$^6$ | 1.32 × 10$^6$ |
| | $k_{off}$ (S$^{-1}$) * | 2.2 × 10$^{-7}$ | 1.15 × 10$^{-5}$ | 4.61 × 10$^{-5}$ |
| | $K_d$ (pM) * | 0.17 | 8.09 | 34.9 |
| PD-1 binding competition (FACS) | $IC_{50}$ (μg/ml) | 0.068 | 0.065 | 0.071 |
| | Max inhibition | 100% | 100% | 100% |
| CD80 binding competition (FACS) | $10_{50}$ (μg/ml) | 0.044 | 0.073 | 0.064 |
| | Max inhibition | 99% | 99% | 99% |
| IL-2 release in HuT78/PD-1[#] | $EC_{50}$ (μg/ml) | 0.057 | 0.046 | 0.057 |
| | Top line (pg/ml) | 2551 | 3124 | 3016 |
| IL-2 release in HuT78/P3Z[§] | $IC_{50}$ (μg/ml) | 0.014 | 0.013 | 0.014 |
| | Max inhibition | 95% | 100% | 100% |

\* $k_{off}$ might be too slow to be accurately measured during the 5-15 min dissociation time in the SPR experiment. Therefore, the affinity might be too strong to be accurately determined using current instrument/experiment setting.
[#]IL-2 release in HuT78/PD-1: IL-2 release induced by the Fabs in HuT78/PD-1 cells co-cultured with HEK293/OS8/PD-L1 cells
[§]IL-2 release in HuT78/P3Z: IL-2 release induced by the Fabs in HuT78/P3Z cells co-cultured with HEK293/PD-L1 cells

TABLE 14

Comparison of CDRs among the selected 333 mAbs

| MAbs | CDR1 | SEQ ID NO | CDR2 | SEQ ID NO | CDR3 | SEQ ID NO |
|---|---|---|---|---|---|---|
| mu333, vh | GFSLTSYGVH | 9 | VIWAGGSTNYNSALMS | 10 | AKPYGNSAMDY | 11 |
| hu333-1A, vh | GFSLTSYGVH | 9 | VIWAGGSTNYNSALMS | 10 | AKPYGNSAMDY | 11 |
| hu333-2B, vh | GFSLTSYGVH | 9 | VIWAGGSTNY<u>VDSVKG</u> | 24 | AKPYGNSAMDY | 11 |
| hu333-3A2, vh | GFSLTSYGVH | 9 | VIWAGGSTNY<u>VDSVKG</u> | 24 | AKPYGNSAMDY | 11 |
| hu333-3C2, vh | GFSLTSYGVH | 9 | VIWAGGSTNYADSVKG | 25 | AKPYGNSAMDY | 11 |
| hu333-3H2, vh | GFSLTSYGVH | 9 | VIWAGGSTNYADSVKG | 25 | AKPYGNSAMDY | 11 |
| hu333-4A2, vh | GFSLTSYCVH | 9 | VIWAGGSTNY<u>VDSVKG</u> | 24 | AKPYGTSAMDY | 26 |
| hu333-4B 2, vh | GFSLTSYCVH | 9 | VIWAGGSTNYADSVKG | 25 | AKPYGTSAMDY | 26 |
| mu333, vk | KASQDVCIVVA | 12 | WASIRHT | 13 | QQYSNYPLYT | 14 |
| hu333-1A, vk | KASQDVCIVVA | 12 | WASIRHT | 13 | QQYSNYPLYT | 14 |
| hu333-2B, vk | KASQDVGIVVA | 12 | WASIRHT | 13 | QQYSNYPLYT | 14 |
| hu333-3 A2, vk | KASQDVGIVVA | 12 | WASIRHT | 13 | QQYSNYPLYT | 14 |
| hu333-3 C2, vk | KASQDVGIVVA | 12 | WASIRHT | 13 | QQYSNYPLYT | 14 |
| hu333-3H2, vk | KASQDVGIVVA | 12 | WASIRHT | 13 | QQYSNYPLYT | 14 |
| hu333-4 A2, vk | KASQDVGIVVA | 12 | WASIRHT | 13 | QQYSNYPLYT | 14 |
| hu333-4B 2, vk | KASQDVGIVVA | 12 | WASIRHT | 13 | QQYSNYPLYT | 14 |

Note:
AA residues underlined are changed from murine sequence to human sequence or mutated for improvement of physicochemical properties.

Figure 7A:
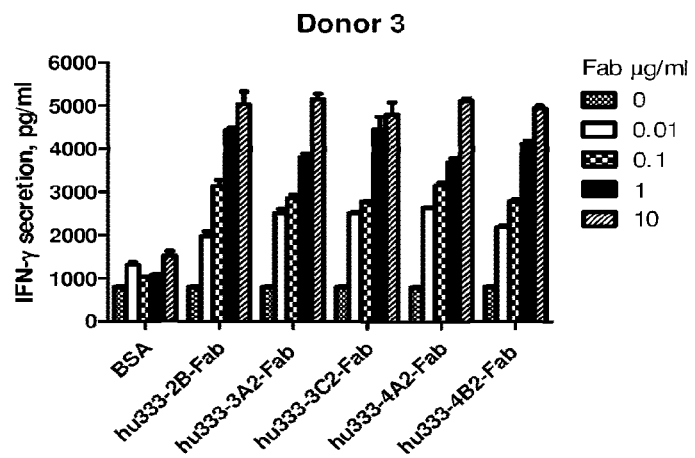
FIG. 7A and FIG. 7B: IFN-γ secretion induced by humanized anti-PD-L1 Fabs in primary human PBMCs from different healthy donors. Donor 3 is shown in FIG. 7A and Donor 17 is shown in FIG. 7B. PBMCs were co-cultured with HEK293/OS8/PD-L1 cells for overnight. IFN-γ in conditioned medium was assayed by ELISA. BSA was used as a negative control.
Figure 7B:
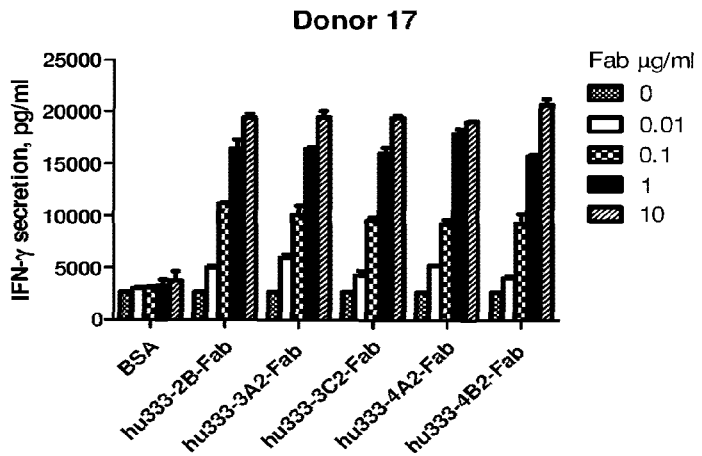

All the humanization mAbs shown above were also confirmed for functional effect on primary human immune cells, peripheral blood mononuclear cells (PBMCs), which were isolated from healthy donors by density gradient centrifugation using ficoll lymphocyte separation medium (Histopaque-1077; Cat. No. 10771, Sigma, St. Louis, USA) according to manufacturer's instruction. PBMCs were then stimulated with 40 ng/mL of anti-CD3 mAb OKT3 (Cat. No. 16-0037, eBioscience, San Diego, Calif., USA) for 3 days prior to the assay. The activated PBMC population mainly consisted of T-cells (50-70%), B-cells and NK cells (15-30%), and monocytes (2-10%). To better mimic the response of T cells to PD-L1 expressing tumor cells upon engagement of TCR/CD3 complex, the activated PBMCs were co-cultured with HEK293/OS8/PD-L1 cells in each well of 96-well plates. Functional effect of anti-PD-L1 mAbs were tested by adding the mAb to the culture, co-cultured for 15-18 hours before harvesting culture supernatants to assess IFN-γ level using Ready-Set-Go! ELISA kits (Cat. No. 88-7316, eBiosciences). As shown in FIG. 7A and FIG. 7B, hu333-2B, hu333-3A2, hu333-3C2, hu333-4A2 and hu333-4B2 all resulted in increase of IFN-γ secretion in a dose-dependent manner. In contrast, negative control, bovine serum albumin (BSA), had no such effect. The results were repeated using PBMCs from two different donors. Although the base level (without mAb) and magnitude changes of IFN-γ secretion with mAb treatment varied among different donors, the fold of increase in IFN-γ secretion remained similarly depending on dose concentration for all hu333.

Example 5. Generation of Recombinant Anti-PD-L1 mAbs without Effector Functions by Fusion to Modified Human IgG1 Constant Region Design of Modified Human IgG1 Constant Region PD-L1 is expressed on a wide range of normal human cells including hematopoietic cells such as T-cells, B-cells, dendritic cells, macrophages, mesenchymal stem cells and bone-marrow derived mast cells, and nonhematopoietic cells and tissues such as lung, hepatocytes, pancreatic islets, placental synctiotrophoblasts and vascular endothelium (Keir et. al. 2006 J Exp Med 203:883-895, Keir et. al. 2008 Ann Rev Immunol 26:677-704, Mu et. al. 2011 Medical Oncology 28:682-688). It is expected that PD-L1 blocking antibodies linked to human wild type IgG-γFc moieties will induce γFc-mediated effector functions, for examples, antibody-dependent cell-mediated cytotoxicity (ADCC) and complement-dependent cytotoxicity (CDC), which might lead to unwanted toxicity to vital organs.

To eliminate effector functions associated with anti-PD-L1mAbs while maintaining optimal physicochemical properties, we constructed hu333-4A2 and hu333-4B2 full antibody by linking the Vh sequences to mutated IgG1 constant regions, and screened for reduced or null Fcγ receptors (FcγRs) binding or C1q binding activities, therefore, attenuating or eliminating ADCC and CDC effector functions. The regions in IgG1 Fc that are involved in interactions with FcγRs and C1q have been studied extensively in the literature (Tao et al. 1993 J Exp Med 178:661-7; Cole et al. 1997 J Immunol 159:3613-21; Armour et. al. 1999 Eur J Immunol 29:2613-2624; Idusogie et. al. 2000 J of Immunol 164:4178-4184; Shields et. al. 2001 J of Biol Chem 276: 6591-6604;

Lund et. al. 2002 Immunol Letters 82:57-65; reviewed by Strohl et. al. 2009 Current Opinion in Biotechnology 20:685-691). Taken together, these data have pointed to the essential role of lower hinge region ($AA_{232-238}$ based on EU nomenclature) for binding to FcγRs and a structurally clustered region ($D_{270}$, $K_{322}$, $P_{329}$ and $P_{331}$ based on EU nomenclature) of CH2 domain for binding to C1q. On the other hand, IgG2 has some sequence variations from IgG1 in the hinge region, which was attributed to weaker binding or no binding to most of the FcγRs except to FcγRIIA$_{H131}$. Indeed, a IgG1/IgG2 hybrid (IgG1Δb) with most of IgG1 hinge sequence incorporating some IgG2 sequences was demonstrated having significantly reduced the binding activities to most FcγRs and attenuated ADCC and CDC effector functions (Armour et. al. 1999 Eur J Immunol 29:2613-2624).

By rational design of mutagenesis with considerations of good pharmaceutical and physicochemical properties, we generated a number of mutants IgG1 in the hinge and Fc regions described above, which were fused to the variable regions of hu333-4A2 and hu333-4B2, respectively, as full antibodies. Two of the IgG1 mutants, IgG1mc and IgG1mf, with favorable features in functional assays were shown in Table 15 in comparison to wild type IgG. The IgG1mc (SEQ. NO. 28) contains a combination of additional mutations, $V_{234}A$, $G_{237}A$ and $P_{239}A$, from the IgG1/IgG2 hybrid described above. The mutations of $V_{234}A$ and $G_{237}A$ were designed to reduce the surface hydrophobic side chain at the γFc/FcγR binding interface to further reduce the binding to FcγRIIA and FcγRIIB, (Lund et. al. 1992 Mol Immunol 29:53-59, Lund et. al. 1996 J Immunol 157:4963-4969, Wines et. al. 2000 J Immunol 164:5313-5318). The $P_{239}A$ mutation was designed to further reduce the C1q binding and CDC (Idusogie et. al. 2000 J of Immunol 164:4178-4184). The IgG1mf (SEQ. NO. 29) was similar to IgG1mc except that the amino acid residue G2 vi was not mutated. The recombinant full length anti-PD-L1 antibodies, hu333-4A2-IgG1mc (SEQ. NO. 30 and 32), hu333-4B2-IgG1mc (SEQ. NO. 31 and 32) and hu333-4B2-IgG1mf (SEQ. NO. 32 and 33) were expressed in HEK293-F cells and purified as described in previous sections.

ELISA Based FcγR and C1 q Binding Assays

It was well documented that IgG mediated effector functions are triggered following on antibody-antigen complex binding to FcγRs or to complement component C1q (Nimmerjahn et. al. 2008 Nature Rev Immunol 8:34-47). For example, ADCC is initiated when an antibody binds to cell surface target protein followed by ligation to FcγRIIIA expressed on effector cells. CDC is activated when an antibody cross-links a cell surface target by binding to C1q protein, which leads to a cascade reaction of complement complex formation and activation and target cell lysis. As proxy of ADCC, CDC and other antibody mediated effector functions, biochemical assays for antibody binding to FcγRs and C1q may serve as the fundamental indicator of ADCC and CDC. We systematically assessed the bindings of the anti-PD-L1 antibodies with modified constant region to all major FcγRs and all known polymorphic variants, including FcγRI, FcγRIIA$_{H131}$, FcγRIIA$_{R131}$, FcγRIIIA$_{F158}$, FcγRIIIA$_{V158}$, FcγRIIB, and FcγRIIIB The extracellular domains of FcγRs were fused to C-terminal His tags as described in previous sections. Recombinant proteins were expressed in 293-F cells by transient transfection and purified using Ni-Sepharose column followed by gel filtration column as described. 2-5 µg/mL of FcγRs were coated on Nunc MaxiSorp ELISA plates (Cat. No. 442404, Nunc, Thermo Fisher) except FcγRIIB and FcγRIIIB, Ni-chelate plates were used (Cat. No. 15242, Pierce, Thermo Fisher). After washing and blocking of the wells, a preformed immune-complex was added to each well and incubated at room temperature for 1-2 hours. The preformed immune-complex contained 60 ng/mL streptavidin-HRP, 60 ng/mL of biotinylated-F(ab')$_2$ goat anti-human IgG (Cat. No. 109-066-097, Jackson ImmunoRes, West Grove, Pa., USA), and 1-5 µg/mL of indicated IgG1 Fc variants fused to the humanized anti-PD-L1 (hu333-4A2 or hu333-4B2) in the blocking buffer. After washing the plate four times, binding signals were detected by chemiluminescence using Immobilon Chemiluminescence Substrate AB (Cat. No. WBKLS0500, Millipore). Table 16 summarized the results of hu333-4A2-IgG1mc (SEQ. NO. 30 and 32), hu333-4B2-IgG1 mc (SEQ. NO. 31 and 32) and hu333-4B2-IgG1mf (SEQ. NO. 32 and 33) binding to various FcγRs. In comparison to the hu333-4A2-IgG1wt, all three IgG1 mutant hu333 mAbs had very low binding activities to FcγRs, which indicated that all three hu333 mAbs above would have significantly reduced effector functions mediated by FcγRs.

TABLE 15

Sequence modifications of IgG1 variants

| | ... 231 | 232 | 233 | 234 | 235 | 236 | 237 | 238 | ... 329 | 330 | 331 | ... |
|---|---|---|---|---|---|---|---|---|---|---|---|---|
| IgG1wt | ... A | P | E | L | L | G | G | P | ... P | A | P | ... |
| IgG2wt | ... A | P | P | V | A | | G | P | ... P | A | P | ... |
| IgG4wt | ... A | P | E | F | L | G | G | P | ... P | S | S | ... |
| IgG1mc | ... A | P | <u>P</u> | <u>A</u> | <u>A</u> | | <u>A</u> | P | ... <u>A</u> | A | P | ... |
| IgG1mf | ... A | P | <u>P</u> | <u>A</u> | <u>A</u> | | G | P | ... <u>A</u> | A | P | ... |

Amino acid numbering is based on EU system. IgG1 sequence modifications are underlined.

TABLE 16

ELISA-based bindings of IgG1 variants to FcγRs

| | hu333-4A2-IgG1wt | | hu333-4A2-IgG1mc | | hu333-4132-IgG1mc | | hu333-4132-IgG1mf | |
|---|---|---|---|---|---|---|---|---|
| FcγRs | Chemiluminescence | Relative binding | Chemiluminescence | Relative binding | Chemiluminescence | Relative binding | Chemiluminescence | Relative binding |
| FcγRI | 42714 | 100% | 136 | 0.3% | 230 | 0.5% | 175 | 0.4% |
| FcγRIIA$_{H131}$ | 54599 | 100% | 61 | 0.1% | 64 | 0.1% | 82 | 0.1% |

TABLE 16-continued

ELISA-based bindings of IgG1 variants to FcγRs

| | hu333-4A2-IgG1wt | | hu333-4A2-IgG1mc | | hu333-4132-IgG1mc | | hu333-4132-IgG1mf | |
|---|---|---|---|---|---|---|---|---|
| FcγRs | Chemiluminescence | Relative binding | Chemiluminescence | Relative binding | Chemiluminescence | Relative binding | Chemiluminescence | Relative binding |
| FcγRIIA$_{R131}$ | 50189 | 100% | 138 | 0.3% | 114 | 0.2% | 158 | 0.3% |
| FcγRIIIA$_{F158}$ | 36402 | 100% | 262 | 0.7% | 252 | 0.7% | 279 | 0.8% |
| FcγRIIIA$_{v158}$ | 57805 | 100% | 323 | 0.6% | 246 | 0.4% | 225 | 0.4% |
| FcγRIIB | 136565 | 100% | 2900 | 2.1% | 2715 | 2.0% | 2069 | 1.5% |
| FcγRIIIB | 40352 | 100% | 2256 | 5.6% | 2009 | 5.0% | 1751 | 4.3% |

Chemiluminescence signal was read using a PheraStar FS microplate reader (BMG Lab ech); For each FcγR, relative binding (percent) was normalized by the chemilumenescence signal of hu333-4A2-IgG1wt binding.

FACS Based FcγR Binding Assays

Bindings of humanized anti-PD-L1 in various IgG1 formats (wt, IgG1mc, IgG1mf, SEQ. NO. 27-29) to FcγRs were also determined by flow cytometry. In brief, a series of stable HEK293 transfectants expressing human FcγRs were established. These stable cell lines expressed FcγRI, FcγRIIA$_{H131}$, FcγRIIA$_{R131}$, FcγRIIB, FcγRIIIA$_{F158}$ or FcγRIIIA$_{F158}$, respectively. Multi-subunit FcγRs (i.e., FcγRI and FcγRIIIA) were co-expressed with FcRγ subunit. A secondary antibody (goat anti-human IgG F(ab')2-Alexa Fluor 488, Cat. No. 109-546-097, Jackson ImmunoResearch, West Grove, Pa., USA) was used to detect the binding of monomeric anti-PD-L1 mAbs with the IgG1 variants (Table 17) to FcγR expressing HEK293 cells. As expected, hu333-4A2 in IgG1wt format (hu333-4A2-IgG1wt) had strong binding signals (MFI) to FcγRI, FcγRIIA$_{H131}$ and FcγRIIIA$_{V158}$. and weak but significant binding signals to FcγRIIA$_{R131}$, FcγRIIB and FcγRIIIA$_{F158}$ (Table 17). The modified IgG1 variants (hu333-4A2-IgG1mc, hu333-4B2-IgG line and hu333-4B2-IgG1mf, SEQ. NO. 30-33) had significantly reduced binding signals which were close to backgrounds.

strength between monomeric γFc and most of the FcγRs is very weak. Human immune system also takes advantage of this mechanism to avoid non-specific activation of FcγRs by monomeric IgG which are present at high levels in serum. In order to assess the bindings to FcγRs in the form of immune-complexes, 10 μg/mL of humanized 333 mAb as various IgG1 mutant forms were premixed with 3 μg/mL of biotin-PD-L1/His and 1.5 μg/mL of neutravidin (Cat. No. A-2666, Invitrogen) in FACS buffer to form the multivalent immune-complexes, before incubating with FcγR-expressing HEK293 cells. Goat anti-human IgG F(ab')2-Alexa Fluor 488 (Cat. No. 109-546-097, Jackson ImmunoResearch) was used to detect the bindings. As shown in Table 18, hu333-4A2-IgG1wt in preformed immune-complex bound to the low affinity FcγRs (FcγRIIA, FcγRIIB, and FcγRIIIA) with much better strength than monomeric IgG1 does (Table 18 data vs. Table 17 data). And again, the anti-PD-L1 mAbs in selected IgG1 mutants (hu333-4A2-IgG1mc, hu333-4B2-IgG1mc and hu333-4B2-IgG1mf,

TABLE 17

Binding strength (MFI*) of monomeric IgG1 variants to FcγRs determined by FACS

| mAbs | FcγRI | FcγRIIA$^{H131}$ | FcγRIIA$_{R131}$ | FcγRIIB | FcγRIIIA$_{F158}$ | FcγRIIIA$_{V158}$ |
|---|---|---|---|---|---|---|
| hu333-4A2-IgG1wt | 1169.42 | 40.52 | 15.14 | 19.00 | 29.45 | 91.65 |
| hu333-4A2-IgG1mc | 4.29 | 5.78 | 3.80 | 3.71 | 5.20 | 3.87 |
| hu333-4B2-IgG1mc | 4.78 | 6.16 | 3.64 | 4.49 | 5.42 | 4.14 |
| hu333-4B2-IgG1mf | 4.56 | 6.12 | 3.99 | 3.73 | 5.09 | 3.91 |

MFI: Mean flourescence intensity from FACS analysis

It has been shown that antibodies bind to FcγRs with much bigger strength in the forms of immune-complexes, which is due to the multivalent effect (Bruhns et. at. 2009 Blood 113:3716-3725). Such bindings are thought to be more relevant under physiological condition, as the binding SEQ. NO. 30-33) had significantly reduced binding signals which were close to backgrounds. Taken together, the humanized 333 in modified IgG1 formats had very little bindings to FcγRs, therefore they should have little FcγRs-mediated effector functions under physiological conditions.

TABLE 18

Binding strength (MFI*) of IgG1 variants as immune-complexes to FcγRs determined by FACS

| mAbs | FcγRI | FcγRIIA$_{H131}$ | FcγRIIA$_{R131}$ | FcγRIIB | FcγRIIIA$_{F158}$ | FcγRIIIA$_{V158}$ |
|---|---|---|---|---|---|---|
| hu333-4A2-IgG1wt | 3261.14 | 599.41 | 159.32 | 539.42 | 74.15 | 308.98 |
| hu333-4A2-IgG1mc | 7.00 | 7.53 | 5.38 | 5.05 | 6.44 | 5.43 |
| hu333-4B2-IgG1mc | 7.01 | 8.09 | 5.28 | 5.03 | 6.81 | 4.89 |
| hu333-4B2-IgG1mf | 7.11 | 7.27 | 4.92 | 5.00 | 6.76 | 4.83 |

MFI: Mean flourescence intensity from FACS analysis

Figure 8:
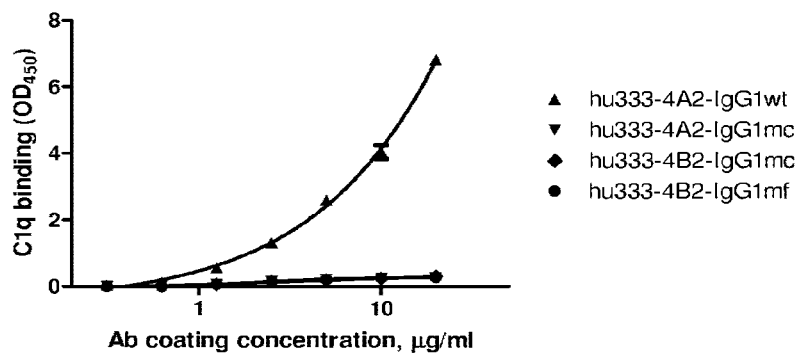
FIG. 8. C1q bindings of humanized anti-PD-L1 mAbs in wild type (IgG1wt) or mutant human IgG1 formates (IgG1mc and IgG1me. Fifty microliters of a serial dilution (x-axis) of humanized anti-PD-L1 mAb were coated on MaxiSorp ELISA plate. Human C1q bindings (y-axis) were assessed by ELISA $OD_{450}$ readings using a specific monoclonal antibody to human C1q.

The ELISA-based C1q binding assay was done by conventional ELISA method with minor modification. Briefly, indicated amounts of the humanized 333 antibodies fused to either wild type or modified IgG1 constant regions were coated onto the Maxisorp ELISA plate. After blocking and washing, the wells were incubated with 2 µg/mL of human C1q (Cat. No. A400, Quidel, San Diego, USA) at room temperature for 2 hours. After washing, the bound C1q was detected using a murine monoclonal antibody against human C1q (Cat. No. A201, Quidel) and HRP conjugated anti-murine IgG (Cat. No. A0168, Sigma, Shanghai, China). As shown in FIG. 8, in contrast to hu333-4A2-IgG1 wt, there were no detectable C1q bindings for the three mAbs with modified IgG1 Fc variants including hu333-4A2-IgG1mc (SEQ. NO. 30 and 32), hu333-4B2-IgG1mc (SEQ. NO. 31 and 32) and hu333-4B2-IgG1 mf (SEQ. NO. 32 and 33). The data indicated that humanized 333 antibodies either in IgG1mc (SEQ. NO. 28) or in IgG1mf format (SEQ. NO. 29) would have very low or null CDC effector function.

ADCC

Classical antibody-dependent cellular cytotoxicity (ADCC) involves activation of NK cells by antibodies engaging to FcγRIIIA (CD16). To test whether humanized anti-PD-L1 antibodies fused to selected human IgG1 variants induce ADCC, NK92MI/CD16V cells, which were generated from NK92MI cells (Cat. No. CRL-2408, ATCC) by co-transducing expression plasmids containing CD16 (V158 allele) and FcRγ genes, were used as effector cells, and PD-L1-expressing HEK293 cell line, HEK293/PD-L1, was used as target cells. The effector cells (105 cells/well) were co-cultured with target cells ($10^4$ cells/well, E:T=10) in 96-well V-bottom plates in the presence of hu333-IgG1 variants (0.0001-1 µg/ml) for 5 h. Cytotoxicity of NK92MI/CD16 cells exerted against HEK293/PD-L1 cells was determined by lactate dehydrogenase (LDH) release assay using the CytoTox 96 Non-Radioactive Cytotoxicity Assay kit (Promega, Madison, Wis.). Specific lysis was determined by the following equation.

$$\% \text{ Specific lysis} = \frac{\text{Experimental} - \text{Effector } Spotaneous - \text{Target } Spotaneous}{\text{Target maximum} - \text{Target } Spotaneous} \times 100$$

Figure 9:
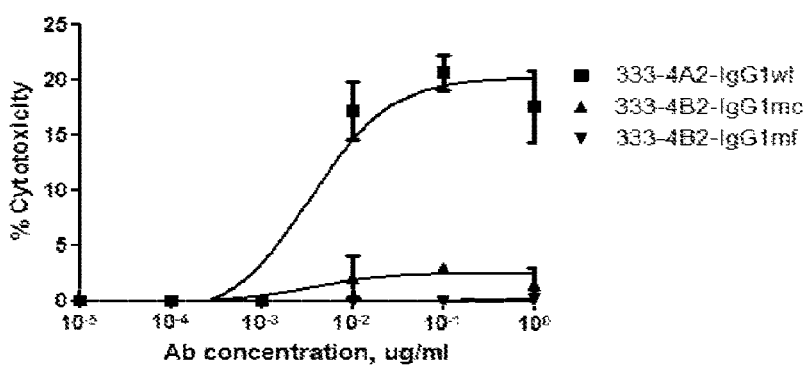
FIG. 9. Antibody-dependent cell-cytotoxicity (ADCC) induced by humanized anti-PD-L1 mAbs in wild type (IgG1wt) or mutant human IgG1 formats (IgG1mc and IgG1mf). Human NK92MI cells transfected with FcγRIIIA were used as effector cells and HEK293/PD-L1 cells were used as target cells. Percentage of cytotoxicity (y-axis) was calculated based on lactate dehydrogenase (LDH) release assay as described in Example 5.

Consistent with the fact that hu333 in IgG1mc and IgG1mf formats had no or significantly reduced bindings to FcγRIIIA (see above section), the ADCC assays showed that both hu333-4B2-IgG1mc (SEQ. NO. 31 and 32) and hu333-4B2-IgG1mf (SEQ. NO. 32 and 33) had only base level of ADCC. In contrast, 333-4A2-IgG1wt with wild type IgG1 Fc induced 20% specific cell lysis at the concentration of 1 µg/mL (FIG. 9).

CDC

Figure 10:
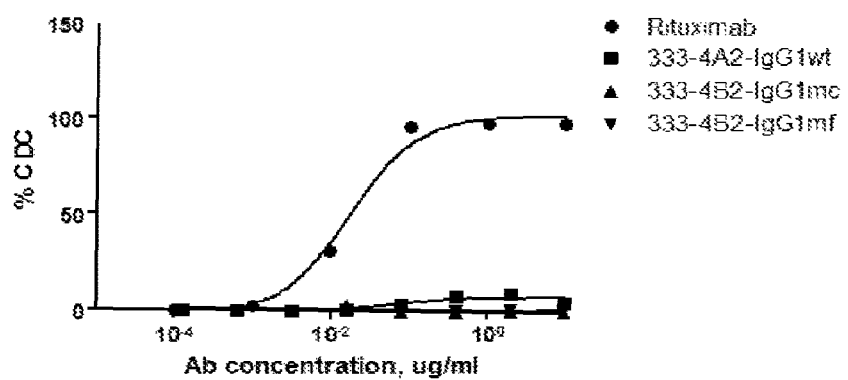
FIG. 10. Complement-dependent cytotoxicity (CDC) activities of humanized anti-PD-L1 mAbs in wild type (IgG1wt) or mutant human IgG1 formats (IgG1mc and IgG1mf). Daudi/PD-L1 cells were used as target cells and human sera from healthy donors were used as the source of complement components. Rituximab (Roche) was used as positive control in classical CDC assay. Percentage of CDC (y-axis) was calculated based on cell-titer glow assay as described in Example 5.

Human IgG1 antibodies, in general, induce significant complement-dependent cytotoxicity (CDC) via classical pathway. Whether the humanized anti-PD-L1 antibodies in selected IgG1 mutant formats (IgG1mc and IgG1mf) trigger CDC was evaluated using a PD-L1-expressing B cell line, Daudi/PD-L1, and fresh human serum from healthy donors, which contains all necessary components for CDC. Cell lysis by CDC was determined by Celltiter glo assay kits (Promega). In brief, Daudi/PD-L1 cells ($2 \times 10^4$ cells/well) were incubated in serum-free RPMI1640 (Invitrogen) with anti-PD-L1 Abs (0.001-10 µg/mL) at 37° C. for 15 minutes before adding normal human serum to the final concentration of 16.6% in 96-well flat-bottom plates in a total volume of 120 µL. After overnight incubation at 37° C., cells were lysed and assayed for ATP concentration. Anti-CD20 mAb Rituximab (Roche) was used as a positive control as Daudi cells constitutively express CD20. The amount of ATP is directly proportional to the number of cells present in culture. Fluorescence was read using a 96-well fluorometer (PHERA Star FS, BMG LABTECH). The results are expressed in relative fluoresence units (RFU) that are proportional to the number of viable cells. The percent CDC activity was calculated as follows: % CDC activity=[(RFU test–RFU background)/(RFU at total cell lysis–RFU background)]×100. As shown in FIG. 10, Rituximab induced robust CDC in $CD20^+$ Daudi/PD-L1 cells. In contrast, both hu333-4B2-IgG1mc (SEQ. NO. 31 and 32) and hu333-4B2-IgG1mf (SEQ. NO. 32 and 33) showed no CDC. Ab 333-4A2-IgG1 wt with wild type IgG1 Fc demonstrated low but above base level of CDC activities especially at concentrations of above 0.3 µg/mL. These data were consistent with the fact that IgG1mc and IgG1mf Fc formats had very little or significantly reduced bindings to complement component C1q (see the previous section).

Example 6. Functional Activities of Humanized mAb 333 in Modified IgG1 Formats

The three humanized mAbs in modified IgG1 formats described above were characterized in cell-based binding assays and functional assessment. Table 19 summarized the study results about hu333-4A2-IgG1mc, hu333-4B2-IgG1mc and hu333-4B2-IgG1mf (SEQ. NO. 30-33).

FACS binding analysis was performed as described in previous sections. Serial dilutions of antibodies were incubated with HEK293/PD-L1 cells and the bindings were detected using the Goat anti-human IgGF(ab')2-Alexa Fluor 488 (Cat. No. 109-546-097, Jackson ImmunoResearch). Dose-dependent binding activities were observed for the selected mAbs to native PD-L1 protein expressed on surface of HEK293 cells. As shown in Table 19, hu333-4A2-IgG1mc, hu333-4B2-IgG1mc and hu333-4B2-IgG1mf showed similar dose-dependent binding activities to the HEK293/PD-L1 cells with $EC_{50}$ (effective concentration at 50% activity) around 0.1 µg/mL.

FACS based competition assays was performed as described earlier. The results shown in Table 19 demonstrated that hu333-4A2-IgG1mc, hu333-4B2-IgG1mc and hu333-4B2-IgG1mf compete off both PD-1/Fc binding ($IC_{50}$s of 0.167-0.174 µg/mL) and CD80/Fc binding ($IC_{50}$s of 0.078-0.118 µg/mL) to HEK293/PD-L1 cells almost equally well.

The functionalities of the purified anti-PD-L1. mAbs were assessed in the HuT78/PD-1 and HEK293/OS8/PD-L1 co-culture system as described in previous section. As shown in Table 19, the humanized 333 mAbs were potent antagonists of PD-L1/PD-1 signaling in this co-culture system, and induced increased IL-2 secretions. Consistent with the result of FACS-based competition assay, hu333-4A2-IgG1 mc, hu333-4B2-IgG1 mc and hu333-4B2-IgG1mf showed similar potencies in this assay with very close $EC_{50}$ (0.075-0.087 µg/mL) and maximum induction of IL-2 levels (287-300 pg/mL).

The functionalities of the purified anti-PD-L1 inAbs were also assessed in the reversed signaling system in which HuT78/P3Z and HEK293/PD-L1 were co-cultured as described. Consistently, the humanized 333 mAbs were potent inhibitor of PD-L1/P3Z signaling in this co-culture system, and inhibited IL-2 secretions induced by PD-L1/

P3Z engagement. And again, hu333-4A2-IgG1mc, hu333-4B2-IgG1mc and hu333-4B2-IgG1mf showed similar potencies in the assay, as shown by similar $IC_{50}$s (0.037-0.045 µg/mL) and maximum inhibition levels (99%) (Table 19).

TABLE 19

Activities of hu333-4A2-IgG1mc, hu333-4B2-IgG1mc and hu333-4B2-IgG1 mf in cell based assays

| Assay/Parameter | | hu333-4A2-IgG1mc | hu333-4B2-IgG1mc | hu333-4B2-IgG1mf |
|---|---|---|---|---|
| FACS binding | $EC_{50}$(µg/ml) | 0.098 | 0.092 | 0.102 |
|  | Top MFI* | 1363 | 1391 | 1342 |
| PD-1 binding | $IC_{50}$(µg/ml) | 0.172 | 0.167 | 0.174 |
| competition (FACS) | Max inhibition | 100% | 100% | 100% |
| CD80 binding | $IC_{50}$ (µg/ml) | 0.078 | 0.103 | 0.118 |
| competition (FACS) | Max inhibition | 100% | 100% | 100% |
| IL-2 release in | $EC_{50}$(µg/ml) | 0.087 | 0.084 | 0.075 |
| HuT78/PD-1[#] | Top line (pg/ml) | 299 | 300 | 287 |
| IL-2 release in | $IC_{50}$(µg/ml) | 0.045 | 0.039 | 0.037 |
| HuT78/P3Z[§] | Max inhibition | 99% | 99% | 99% |

Figure 11A:
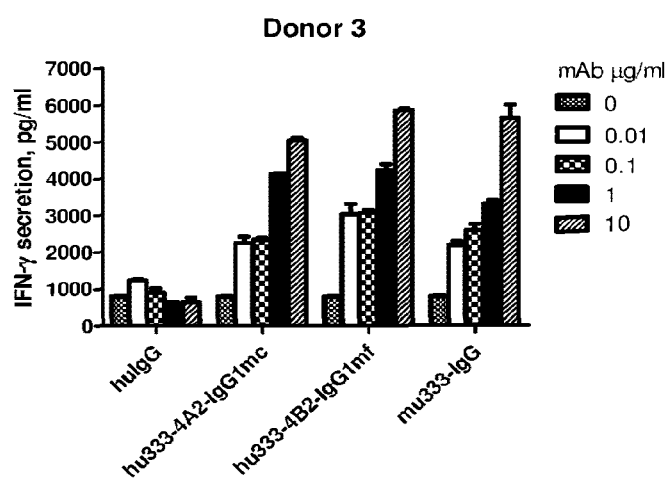
FIG. 11A and FIG. 11B: IFN-γ secretion induced by humanized anti-PD-L1 mAbs in primary human PBMCs from different healthy donors. Donor 3 is shown in FIG. 11A and Donor 17 is shown in FIG. 11B. PBMCs were co-cultured with HEK293/OS8/PD-L1 cells for overnight. IFN-γ in conditioned medium was assayed by ELISA. Human IgG served as a negative control.
Figure 11B:
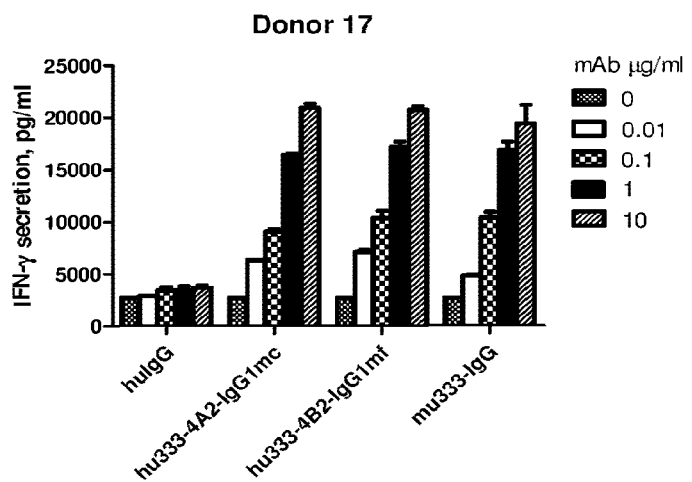

*MFI: Mean fluorescence intensity from FACS analysis.
[#]IL-2 release in HuT78/PD-1: IL-2 release induced by the Fabs in HuT78/PD-1 cells co-cultured with HEK293/OS8/PD-L1 cells.
[§]IL-2 release in HuT78/P3Z: IL-2 release induced by the Fabs in HuT78/P3Z cells co-cultured with HEK293/PD-L1 cells To verify if the humanized 333 antibodies also exert functional effect on primary human immune cells, we assayed the antibody function using freshly isolated peripheral blood mononuclear cells (PBMCs), which are mainly consisted of T-cells (50-70%), B-cells and NK cells (15-30%), and monocytes (2-10%). Human PBMCs were isolated from healthy donors by density gradient centrifugation using ficoll lymphocyte separation medium (Histopaque-1077; Cat. No. 10771, Sigma) according to manufacturer's instruction. The human blood collections were done followed the Internal Procedure of BeiGene. PBMCs were then stimulated with 40 ng/mL of anti-CD3 mAb OKT3 (Cat. No. 16-0037, eBioscience, CA) for 3 days prior to the assay. To mimic the response of pre-activated T cells to PD-L1 expressing tumor cells upon engagement of TCR/CD3 complex, PBMCs ($1 \times 10^4$ cells) were co-cultured with HEK293/OS8/PD-L1 cells ($3 \times 10^4$ cells) in each well of 96-well flat-bottom plates. Indicated concentrations of anti-PD-L1 antibodies were added to the culture. After 15-18 hours of co-culture, culture supernatants were assayed for IFN-γ level by ELISA using Ready-Set-Go! ELISA kits (Cat. No. 88-7316, eBiosciences), which is the most prominent indicator of T-cell activation, as well as of other immune cell activation (Thakur et. al. 2012 Vaccine 30:4907-4920). As shown in FIG. 11A and FIG. 11B, the presence of rnAb hu333-4A2-IgG1mc or hu333-4B2-IgG1mf in the co-culture of pre-activated PBMCs and HEK293/OS8/PD-L1 cells resulted in increasing IFN-γ production in a dose-dependent manner. As a control, huIgG had no such effect of stimulating IFN-γ secretion. The potencies of hu333-4A2-IgG1mc and hu333-4B2-IgG1mf were comparable to the parental murine antibody mu333-IgG. Although the base level of IFN-γ without antibody treatment varied among different donors, the increase of IFN-γ secretion in PBMCs treated by hu333-4A2-IgG1mc, hu333-4B2-IgG1mf and mu333-IgG was statistically significant in the range of 0.01 to 10 µg/mL of antibody treatment (about 5-8 fold induction at 10 µg/mL depending on the donor).

Taken together, these data demonstrated that hu333-4A2-IgGmc, hu333-4B2-IgGmc and hu333-4B2-IgG1mf were potent antagonists blocking PD-L1/PD-1 interactions and downstream signaling in all the cell line and primary immune cell-based assays. They were very similar in their functional activities and potencies, as they were very similar in sequences (only minor difference in framework regions), shared identical binding epitope and had very similar binding affinities and specificity (sec below section).

Example 7. Binding Affinity and Specificity of Humanized Anti-PD-L1 mAbs

Binding Specificity of Anti-PD-L1 mAbs to PD-L1 Proteins from Different Species

Figure 12A:
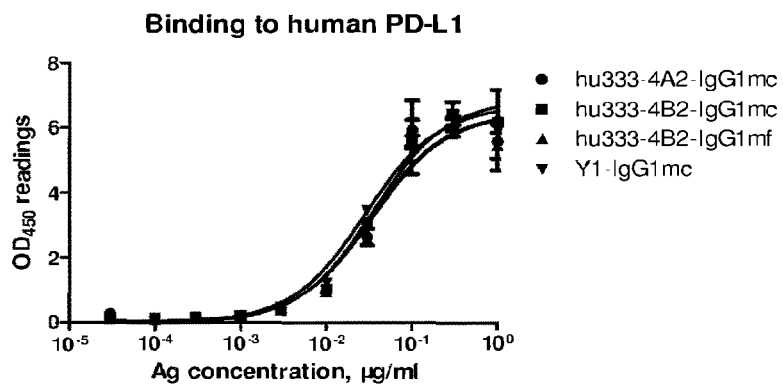
FIG. 12A, FIG. 12B, and FIG. 12C: Dose-dependent bindings of anti-PD-L1 mAbs to the purified human PD-L1/His (FIG. 12A), cynomolgus monkey PD-L1/His (FIG. 12B), and mouse PD-L1/His (FIG. 12C) in ELISA. MaxiSorp ELISA plates were coated with 50 microliters of human, monkey and mouse PD-L1/His, respectively. Concentrations of anti-PD-L1 mAbs were indicated by x-axis. The binding signal strength was indicated by direct $OD_{450}$ readings (y-axis).
Figure 12B:
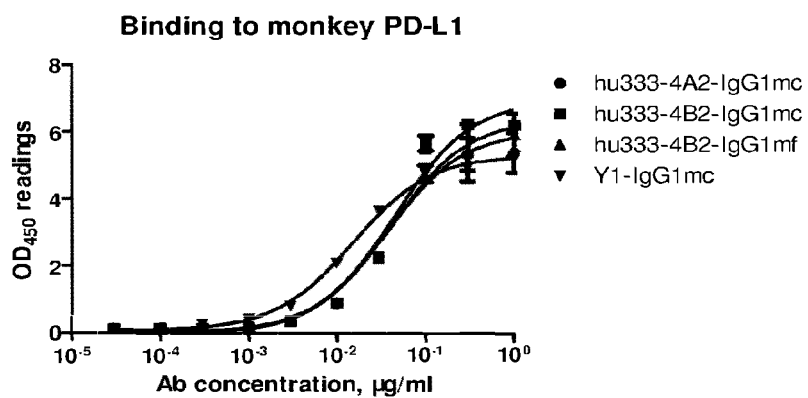
Figure 12C:
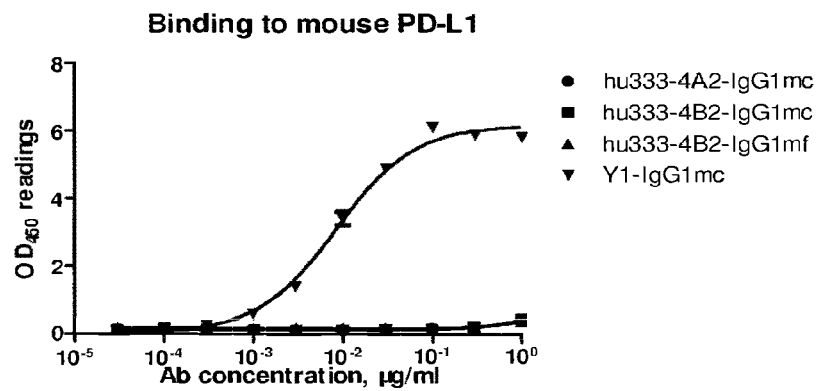

The binding specificity was studied for the mAbs hu333 (hu333-4A2-IgG1mc, hu333-4B2-IgG1mc and hu333-4B2-IgGlmf) using human, cynomolgus monkey (*Macaca fascicularis*) and mouse (*Mus musculus*) PD-L1 as target proteins. The monkey PD-L1/His and murine PD-L1/His were expressed and purified in a similar way to the human PD-L1/His as described earlier. Y1 was a reference functional anti-PD-L1 mAb which was synthesized according to a published patent (US 2010/0203056 A1) and fused to human IgG1mc variant. The synthesized full length mAb was named as Y1-IgG1mc. The ELISA assay was performed essentially in the same way as described in the previous section. Briefly, 200 ng of PD-L1 protein was coated on each well of Nunc MaxiSorp ELISA plate (Cat. No. 442404, Nunc, Thermo Fisher). After washing and blocking, indicated concentrations of anti-PD-L1 mAbs were added and incubated at room temperature for 1 hour. After washing, the bound anti-PD-L1 mAbs were detected using a HRP-conjugated goat anti-human Fc antibody (Cat. No. A0170, Sigma). As shown in FIG. 12A, FIG. 12B, and FIG. 12C, hu333-4A2-IgG1mc (SEQ. NO. 30 and 32), hu333-4B2-IgG1mc (SEQ. NO. 31 and 32) and hu333-4B2-IgG1mf (SEQ. NO. 32 and 33) bound to human and monkey PD-L1 in a dose-dependent manner, but not to murine PD-L1, which was consistent with the fact that the original mu333 was generated from mouse immunized with human PD-L1/Fc and that human and monkey PD-1 shares high degree of sequence homology (96%). In contrast, Y1-IgG1mc bound to all PD-L1 proteins from human, monkey and mouse.

Affinity Determination of Humanized Anti-PD-L1 Fabs by SPR

Hu333-4A2 (SEQ. NO. 21 and 23), hu333-4B2 (SEQ. NO. 22 and 23) and the reference antibody Y1 were constructed as human IgG1 Fab format in which the Vh and Vk were fused to the N-terminus of human IgG1-CH1 and constant region of kappa chain, respectively. The IgG1-CH1 was fused to a C-terminal His6 tag to facilitate purification. Expression and purification of recombinant Fabs were performed as described in the previous section.

For affinity determinations of anti-PD-L1 Fabs, SPR assays were conducted using BIAcore™ T-200 instrument (GE Life Sciences, Shanghai, China) as described earlier. Association rates ($k_{on}$) and dissociation rates ($k_{off}$) were calculated using the one-to-one Langmuir binding model (BIA Evaluation Software, GE Life Sciences). The equilibrium dissociation constant ($K_d$) was calculated as the ratio $k_{off}/k_{on}$.

The SPR-determined binding affinities of anti-PD-L1 Fabs were listed in Table 20. Hu333-4A2 and hu333-4B2 Fabs bind to human PD-L1 with higher affinities than Y1 Fab does, which was indicated by the faster $k_{on}$, slower $k_{off}$ and much smaller $K_d$ value. The hu333-4A2 and hu333-4B2 Fabs hind to monkey PD-L1 almost equally well as their binding to human PD-L1. In contrast, Y1 Fab binds to the monkey PD-L1 with about 100-fold lower affinity than its binding to human PD-L1 ($K_d$ of 0.18 nM to human PD-L1 and $K_d$ of 16.2 nM to monkey PD-L1).

TABLE 20

Affinities of anti-PD-L1 Fabs to human and monkey PD-L1 determined by SPR

| Binding kinetics/parameter | | hu333-4A2 Fab | hu333-4B2 Fab | Y1 Fab |
|---|---|---|---|---|
| Affinity to human PD-L1 | $k_{on}$ (M$^{-1}$s$^{-1}$) | 3.88 × 10$^6$ | 3.78 × 10$^6$ | 4.97 × 10$^5$ |
| | $k_{off}$ (S$^{-1}$) * | 1.03 × 10$^{-5}$ | 1.32 × 10$^{-5}$ | 9.00 × 10$^{-5}$ |
| | $K_d$ * | 2.65 pM | 3.50 pM | 0.18 nM |
| Affinity to monkey PD-L1 | $k_{on}$ (M$^{-1}$s$^{-1}$) | 3.19 × 10$^6$ | 3.20 × 10$^6$ | 2.35 × 10$^5$ |
| | $k_{off}$ (S$^{-1}$) * | 0.93 × 10$^{-5}$ | 0.80 × 10$^{-5}$ | 3.79 × 10$^{-3}$ |
| | $K_d$ * | 2.91 pM | 2.5 pM | 16.2 nM |

* koff might be too slow to be accurately measured during the 5-15 min dissociation time in the SPR experiment. Therefore, the affinity might be too strong to be accurately determined for hu333-4A2 Fab and hu333-4B2 Fab using current instrument/experiment setting.

Epitope Mapping of Anti-PD-L1 mAbs

The previous reports about the crystal structures of PD-1/PD-L1 complexes shed light on the critical amino acid (AA) residues of PD-L1 that directly interact with receptor PD-1 (Zhang et. al. 2004 Immunity 20:337-347; Lin et. al. 2008 PNAS 105:3011-3016; Lazar-Molnar et. al. 2008 PNAS 105:10483-10488). Through point mutation analysis, eight AA residues in PD-L1 sequence were identified being required for its binding to PD-1. Based on the information from the structure-guided mutation analysis, we hypothesized that most effective way for the functional mAbs to block PD-L1 mediated signaling is to compete with PD-1 by binding to the eight critical AA residues, therefore, occupying the binding epitopes required for its binding to PD-1 receptor. To explore the hypothesis and to understand the mechanism of action by functional PD-L1 mAbs, we made eight mutants of PD-L1 by replacing each of the eight critical AAs to Ala, individually, i.e. $F_{19}A$, $I_{54}A$, $R_{113}A$, $M_{115}A$, $D_{122}A$, $Y_{123}A$, $K_{124}A$ and $R_{125}A$ (AA residue numbering based on Lin et. al. 2008 PNAS 105:3011-3016). The wild-type PD-L1/His (FIG. 1) was used as template for rolling-circle mutagenesis using Fast Mutagenesis kit (Cat. No. FM111, Transgen Biotech, Beijing, China). All mutants were sub-cloned in our pcDNA-based expression vectors, and verified by sequencing. The mutant and wild-type PD-L1/His proteins were expressed by transient transfection as described in previous sections. The conditioned media (CM) were collected after 4 to 6 days of culture, and analyzed by Western blot to verify the PD-L1/His protein expression in terms of quality and quantity. The supernatants (CM), after clearing cell debris, were directly used in ELISA analysis or Western blot for epitope-mapping.

ELISA assays using the wild-type and mutant PD-L1/His were performed to study the binding epitopes of the anti-PD-L1 mAbs. For comparison of antibody binding epitopes, several murine mAbs from us and one reference antibody Y1-IgG1 (adapted from US 2010/0203056 A1 and fused to human IgG1kappa constant regions) were included in the study. Equal volume of CM containing wild type or mutant PD-L1/His was coated in 96-well plate for all mAbs in the same ELISA assay. The ELISA results were normalized using the mean ELISA readings of wild type PD-L1 binding signals as the standard. ELISA binding signals to a specific mutant PD-L1 were further normalized against the highest antibody binding read-out (set as 100%) to the specific mutant PD-L1 to even out expression variations between PD-L1 mutants. For convenience of data analysis, when a mAb's ELISA binding signal for a specific PD-L1 mutant dropped below 50% relative to wild type PD-L1, it was defined that the binding function is significantly impaired due to the corresponding amino acid mutation. Likewise, if a mAb's ELISA binding signal for a specific mutant dropped below 25%, it was defined to be very significant.

Figure 13:
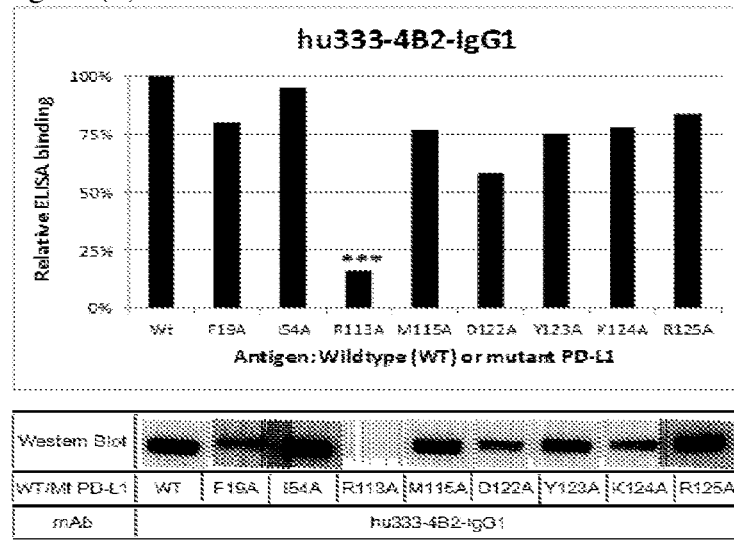
FIG. 13A and FIG. 13B: Mapping the binding epitopes of anti-PD-L1 mAbs by ELISA (upper panel) and Western Blot (lower panel).
FIG. 13C: Binding activities to D26A mutant PD-L1 by anti-PD-L1 mAbs. Conditioned media containing wild type or mutant PD-L1/His proteins were used to assess binding activity by ELISA and Western Blot.  indicates the PD-L1 mutant to which the mAb binding activity reduced to 25-50% of that to wild type PD-L1. * indicates the PD-L1 mutant to which the mAb binding activity reduced below 25% of that to wild type PD-L1.
Figure 13:
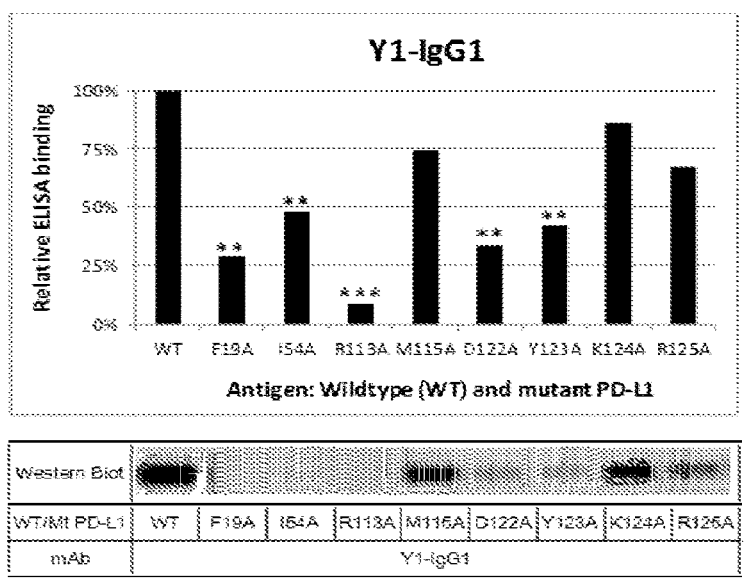

As shown in FIG. 13A, amino acid residues R113 in PD-L1 is critical for hu333-4B2-IgG1 binding to PD-L1, whose mutation significantly impaired the hu333-4B2-IgG1 binding to PD-L1. On the other hand, the reference antibody Y1-IgG1 had distinctive binding epitopes. $F_{19}$, $I_{54}$, $D_{122}$ and $Y_{123}$ were all significant epitopes for its binding besides R113 (FIG. 13B). Different signatures of binding epitopes were also observed in other anti-PD-L1 mAbs from our study. The data from Western blot for both hu333-4B2-IgG1 and Y1-IgG1 antibodies confirmed these results although the antigen proteins were denatured.

Figure 13C:
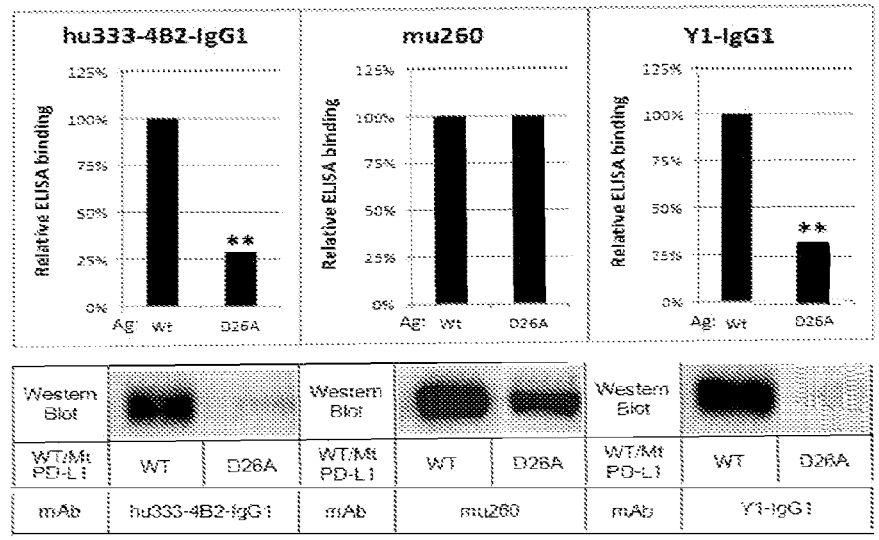

Apart from the above key binding epitope mutations, we also made the mutation D26A. ELISA and Western blot results showed the mutation D26A in PD-L1 significantly inhibited the binding activities of all functional anti-PD-L1 mAbs including mAbs mu333, hu333-4B2-IgG1 and Y1-IgGI, but not inhibited the binding of non-functional antibodies, such as mu260 (FIG. 13C). As summarized in Table 21, similar to mu333 and its derivative humanization mAbs, hu333-4B2 binds to two key amino acid residues (epitopes) of human PD-L1, D26 and R113; in contrast, mAb Y1 binds to at least six amino acid residues.

TABLE 21

Summary of epitope-mapping results

| mAb | F19A | D26A | I54A | R113A | M115A | D122A | Y123A | K124A | R125A |
|---|---|---|---|---|---|---|---|---|---|
| hu333-4B2-IgG1 | | ** | | *** | | | | | |
| Y1-IgG1 | ** | ** | ** | *** | | ** | ** | | |

** Mutations inhibited >50% binding comparing to wildtype PD-L1.
*** Mutations inhibited >75% binding comparing to wildtype PD-L1.

Through the epitope mapping study, we have demonstrated that anti-PD-L1 mAbs are capable of binding to different epitope signatures through molecular recognition, which might have profound impact on binding affinity, binding specificity and functional activity, e.g. hu333-4A2 and hu333-4B2 can only bind to human PD-L1 (FIG. 12A), but not to mouse PD-L1 (FIG. 12C); in contrast, Y1 binds to both human and mouse PD-L1 (FIGS. 12A and 12C) although human and mouse PD-L1 have 26% sequence divergence.

Non-Specific Binding to Human Serum Proteins

Figure 14A:
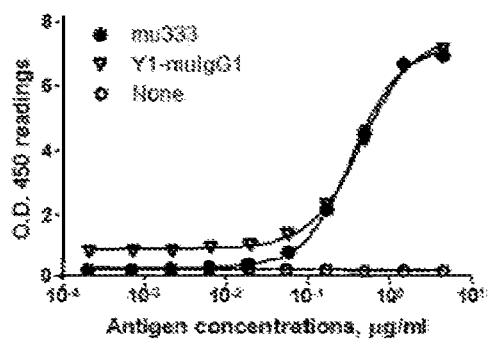
FIG. 14A and FIG. 14B: Binding assays of anti-PD-L1 mAbs to a mixture of human serum protein and PD-L1 antigen by ELISA.
Figure 14B:
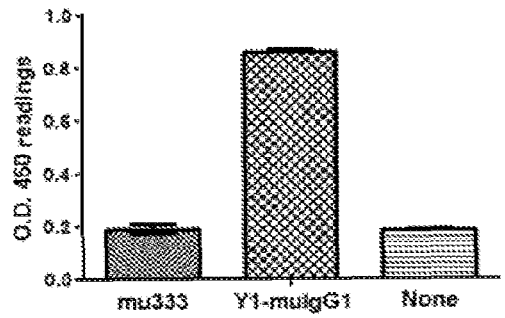

In order to check whether mAb mu333 has non-specific binding to human serum proteins, ELISA study was performed using 96-well Nunc Maxisorp ELISA plates coated with 5% human serum (from healthy donors) and various concentrations of PD-L1/His antigen as indicated in FIG. 14A, x-axis. Same amount of murine PD-L1 Abs or a chimeric Y1 (named as Y1-muIgG1), which was made of Y1 variable domains fused to murine IgG1kappa constant regions) were added in the ELISA reaction, and the bindings were detected with anti-mouse Fc-HRP (Cat. No. A9309, Sigma). The PBS buffer without any antibody was included as negative control (FIG. 14).

As shown in FIG. 14A, the baseline O.D. reading (the reading at very low antigen concentration) for mu333 was almost identical to the negative control, while the baseline O.D. reading for Y1-muIgG1 is 4 folds higher than the negative control (PBS), indicating a differential property between mu333 and Y1-mIgG1 in binding selectivity. The humanized mAb hu333-4B2-IgG1mc and hu333-4B2-IgG1mf were also assessed for non-specific binding in similar assay method using fetal bovine serum (FBS) instead of human serum. Reminiscent to its parental mouse hybridoma mAb, hu333-4B2-IgG1mc and hu333-4B2-IgG1mf had no binding to FBS.

Example 8. Pharmacokinetics

Pharmacokinetics of Hu333-4B2-IgG1mf in Mice

All animal studies were performed following BeiGene Animal Care and Use Procedure. Ten to twelve week-old female Balb/c nude mice (18-25 g) were used to study the pharmacokinetics of the humanized mAb hu333-4B2-IgG1mf (SEQ. NO. 32 and 33). Mice were dosed with 10 mg/kg of mAb hu333-4B2-IgG1mf either as a single intravenous (i.v.) or subcutaneous (s.c.) injection. Intravenous injections were administered via a tail vein, and subcutaneous injections were administered in the flank. In each injection group, mice were separated into different subgroups and in each subgroup blood sera were collected at certain time points. For i.v. injection group, serum was harvested 2 days predose, and postdose at 15 min, 30 min, 60 min, 90 min, 6 h, 24 h and once on days 2, 3, 4, 5, 7, 10, 14, 21 and 28. For s.c. injection group, serum was harvested 2 days predose, and postdose at 1.5 h, 6 h, 24 h and once on days 2, 3, 4, 5, 7, 10, 14, 21, and 28.

Serum level of hu333-4B2-IgG1mf was determined by ELISA using human PD-L1/His protein. Briefly, Nunc MaxiSorp ELISA plates (Cat. No. 442404, Nunc, Thermo Fisher) were coated overnight at 4° C. with 100 μL per well of 3 μg/mL human PD-L1/His protein. Plates were blocked with 3% bovine serum albumin, 0.05% Tween 20 in PBS (blocking buffer) at room temperature for 1 hour. After washing, serially diluted serum samples and purified hu333-4B2-IgG1mf standards were added and incubated at room temperature for 1 hour. After washing, the bound hu333-4B2-IgG1mf was detected using a HRP-conjugated goat anti-human Fc antibody (Cat. No. A0170, Sigma) and color developed using TMB substrate (Cat. No. 10440, Sigma). A standard curve was fit using nonlinear regression and the serum concentrations of hu333-4B2-IgG1mf were deduced from the standard curve and dilution factors.

The serum concentrations of hu333-4B2-IgG1mf versus time data were analyzed using the non-compartment model for the i.v. and s.c. doses (WinNonlin, Pharsight). The clearance, volume of distribution, half-lives, mean residence time and bioavailability were deduced from WinNonlin data fitting.

The pharmacokinetics of hu333-4B2-IgG1mf in mice was summarized in Table 22. After i.v. administration, hu333-4B2-IgG1mf (SEQ. NO. 32 and 33) concentrations were cleared from the serum in a biphasic manner. The terminal half-life was about 10-14 days. After an i.v. dose of 10 mg/kg, the clearance was 7.9 mL/day/kg in mice. After s.c. administration, peak concentrations of hu333-4B2-IgG1mf in the serum as approximately 30-50% of that noted after i.v. administration of the same dose. Comparison of the AUC after the 10 mg/kg s.c. and i.v. dose indicated a bioavailability of 90%. All these PK parameters were close to those of typical humanized monoclonal antibodies, indicating that hu333-4B2-IgG1mf (SEQ. NO. 32 and 33) had good in vivo stability in mice.

Pharmacokinetics of Hu333-4B2-IgG1mc in Cynomolgus Monkey

The pharmacokinetics of hu333-4B2-IgG1mc (SEQ. NO. 31 and 32) was studied in cynomolgus monkeys. As humanized 333 bound to human and monkey PD-L1 with almost identical affinities, the pharmacokinetic profile in cynomolgus monkeys should be very informative and scalable to predict the pharmacokinetic profile in humans. The drug administrations and blood serum collections were done at 3D BioOptima Co. Ltd (Suzhou, China) following 3D BioOptima's Animal Care and Use Procedure. Briefly, two 3-5 year-old male monkeys were dosed with 10 mg/kg of mAb hu333-4B2-IgG1mc as a single intravenous (i.v.) dose. Blood samples (~1 mL) were collected at 2 days pre-dosing, 5 min, 30 min, 2 h, 6 h, 12 h, 24 h, 36 h, and 2, 3, 5, 7, 10, 15, 22, 30 days post-dosing via cephalic vein into tubes.

ELISA based bioanalyses and pharmacokinetic analyses were performed essentially as described above. At each time point, the averaged serum concentration from 2 monkeys was used for fitting except for the time points of 22 and 30 days post dose, where the data from only one monkey were used, as another monkey showed accelerated clearance and undetectable hu333-4B2-IgG1mc serum levels, presumably due to a monkey anti-drug immune response, at these two time points. The serum concentration of hu333-4B2-IgG1mc versus time data were analyzed using the non-compartment model for the i.v. dose.

TABLE 22

Pharmacokinetics of hu333-4B2-IgG1mc after s.c./i.v. administration in nude mice

| Parameters | 10 mg/kg i.v. | 10 mg/kg s.c. |
| --- | --- | --- |
| $C_{max}$ (mg/mL) | 250 | 70.6 |
| $V_{ss}V$ (mL/kg) | 105 | N/A |
| CL/W (mL/day/kg) | 7.9 | N/A |
| $T_{1/2}$ terminal (day) | 9.6 | 11.3 |
| $AUC_{0-inf}$ (mg/mL*day) | 1266 | 1147 |

TABLE 22-continued

Pharmacokinetics of hu333-4B2-IgG1mc after s.c./i.v. administration in nude mice

| Parameters | 10 mg/kg i.v. | 10 mg/kg s.c. |
|---|---|---|
| MRT (day) | 13.3 | 16.5 |
| Bioavailability (%) | N/A | 90% |

$C_{max}$, maximum observed concentration;
$V_{ss}/W$, steady-state volume of distribution;
CL/W, serum clearance;
$T_{1/2}$, half life;
AUC, area under the curve;
MRT, mean residence time in the body;
N/A: not applicable

TABLE 23

Pharmacokinetics of hu333-4B2-IgG1mc after i.v. administration in cynomolgus monkeys

| Parameters | 10 mg/kg i.v. |
|---|---|
| $C_{max}$ (mg/mL) | 283.4 |
| $V_{ss}/W$ (mL/kg) | 80 |
| CL/W (mL/day/kg) | 6.4 |
| $T_{1/2}$ terminal (day) | |
| $AUC_{0-inf}$ (mg/mL*day) | |
| MRT (day) | |

$C_{max}$, maximum observed concentration;
$V_{ss}/W$, steady-state volume of distribution;
CL/W, serum clearance;
$T_{1/2}$, half life;
AUC, area under the curve;
MRT, mean residence time in the body The pharmacokinetics of hu333-4B2-IgG1mc in cynomolgus monkeys was summarized in Table 23. After i.v. administration, hu333-4B2-IgGlmc concentrations were cleared from the sera in a biphasic manner. The terminal half-life was about 9 days. After an i.v. dose of 10 mg/kg, the clearance was 6.4 mL/day/kg in cynomolgus monkeys. After i.v. administration, peak concentration of hu333-4B2-IgG1mc was 283 pg/mL at 5 min post dose. These PK parameters indicated that hu333-4B2-IgGlmc had normal pharmacokinetic profile in cynomolgus monkeys, which predicted normal pharmacokinetic behavior in humans (Deng et. al. 2011 mAbs 3:61-66).

Example 9. Humanized Anti-PD-L1 mAb Inhibits Tumor Growth in a Mouse Xenograft Cancer Model In Vivo The T-cell line and PBMC-based experiments indicated that the anti-PD-L1 mAb might work in mouse cancer models utilizing immune-compromised mice xenografted with human cancer cells, subsequently implanting human PBMCs and applying the mAb treatment to inhibit cancer cell growth in vivo. An allogeneic mouse cancer model was designed as follows. Female NOD/SCID mice (6-7 weeks) were pre-treated with cyclophosphamide. Human peripheral blood mononuclear cells (PBMCs) were isolated from blood of healthy human volunteer, mixed with A431 epidermoid carcinoma cells (Cat. No. CRL-1555 ATCC) and matrigel, and injected subcutaneously into the right front flank of the animals. Starting from day 0 after cell inoculation, animals were randomly assigned into 3 groups with 8 mice per group. Mice were treated twice weekly (BIW i.p.) with vehicle (PBS) or 10 mg/kg hu333-4B2-IgG1mf (SEQ. NO. 32 and 33) for 4 weeks. Individual animal body weight and tumor volume were recorded twice weekly, with mice being monitored daily for clinical signs of toxicity for the duration of the study. Tumor volumes were calculated using the following formula: $[D \times (d^2)]/2$, in which D represents the large diameter of the tumor, and d represents the small diameter.

Figure 15:
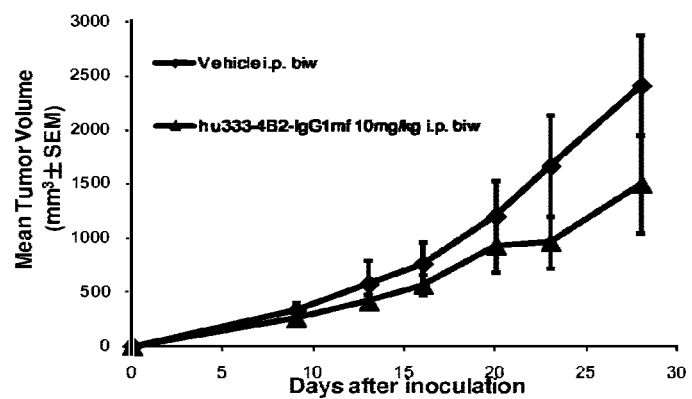
FIG. 15. Mean tumor growth curves upon treatment with hu333-4B2-IgG1mf or vehicle. NOD/SCID mice implanted with human cancer cells A431 and PBMCs from healthy donors were treated with hu333-4B2-IgG1mf at the dose regimen of 10 mg/kg, twice/week.

As shown in FIG. 15, in the anti-PD-L1 mAb (hu333-4B2-IgG1mf)-treated group, the A431 tumor growth was slower compared to that in the PBS-treated group. The results indicated that the anti-PD-L1 mAb described can activate human immune cells to inhibit tumor cells growth in the mouse in vivo cancer model, which is consistent with the in vitro experimental results described in previous sections.

What is claimed is:

1. An antibody or fragment thereof that specifically binds to PD-L1, wherein the antibody or fragment thereof comprises a heavy chain complementary determining region (CDR) 1 according to SEQ ID NO: 9, a heavy chain CDR2 according to SEQ ID NO: 25, a heavy chain CDR3 according to SEQ ID NO: 26, a light chain CDR1 according to SEQ ID NO: 12, a light chain CDR2 according to SEQ ID NO: 13, and a light chain CDR3 according to SEQ ID NO: 14.

2. The antibody or fragment thereof according to claim 1, comprising a heavy chain variable region having at least 80% homology to SEQ ID NO: 22.

3. The antibody or fragment thereof according to claim 1, comprising a light chain variable region having at least 80% homology to SEQ ID NO: 23.

4. The antibody or fragment thereof according to claim 1, comprising a heavy chain variable region according to SEQ ID NO: 22 and a light chain variable region according to SEQ ID NO: NO: 23.

5. The antibody or fragment thereof according to claim 1, wherein the antibody is a monoclonal antibody.

6. The antibody of claim 5, wherein the monoclonal antibody is an IgG1 antibody.

7. The antibody or fragment thereof according to claim 1, comprising a heavy chain having at least 80% homology to SEQ ID NO: 33.

8. The antibody or fragment thereof according to claim 1, comprising a light chain having at least 80% homology to SEQ ID NO: 32.

9. The antibody or fragment thereof according to claim 1, comprising a heavy chain according to SEQ ID NO: 33 and a light chain according to SEQ ID NO: 32.

10. The antibody or fragment thereof according to claim 1, wherein the fragment is selected from the group consisting of a Fab fragment, a Fab' fragment, a F(ab')2 fragment, an Fv fragment, and a single chain fragment.

11. A composition comprising the antibody or fragment thereof of claim 1.

12. A polynucleotide encoding the antibody or fragment thereof of claim 1.

13. A method of producing an anti-PD-L1 antibody or fragment thereof, the method comprising:
    culturing a cell comprising one or more nucleic acids encoding the antibody or fragment thereof, wherein the antibody or fragment thereof comprises a heavy chain complementary determining region (CDR) 1 according to SEQ ID NO: 9, a heavy chain CDR2 according to SEQ ID NO: 25, a heavy chain CDR3 according to SEQ ID NO: 26, a light chain CDR1 according to SEQ ID NO: 12, a light chain CDR2 according to SEQ ID NO: 13, and a light chain CDR3 according to SEQ ID NO: 14, under conditions wherein the antibody or antigen-binding fragment thereof is produced; and
    recovering the antibody or fragment thereof from the cell.

14. The method of claim 13, wherein the one or more nucleic acids are incorporated into one or more expression vector.

* * * * *

SEQUENCE LISTING

<160> NUMBER OF SEQ ID NOS: 33

<210> SEQ ID NO 1
<211> LENGTH: 870
<212> TYPE: DNA
<213> ORGANISM: Homo sapiens

<400> SEQUENCE: 1

```
atgaggatat ttgctgtctt tatattcatg acctactggc atttgctgaa cgcatttact      60
gtcacggttc ccaaggacct atatgtggta gagtatggta gcaatatgac aattgaatgc     120
aaattcccag tagaaaaaca attagacctg gctgcactaa ttgtctattg ggaaatggag     180
gataagaaca ttattcaatt tgtgcatgga gaggaagacc tgaaggttca gcatagtagc     240
tacagacaga gggcccggct gttgaaggac cagctctccc tgggaaatgc tgcacttcag     300
atcacagatg tgaaattgca ggatgcaggg gtgtaccgct gcatgatcag ctatggtggt     360
gccgactaca agcgaattac tgtgaaagtc aatgccccat acaacaaaat caaccaaaga     420
attttggttg tggatccagt cacctctgaa catgaactga catgtcaggc tgagggctac     480
cccaaggccg aagtcatctg gacaagcagt gaccatcaag tcctgagtgg taagaccacc     540
```

-continued

```
accaccaatt ccaagagaga ggagaagctt tcaatgtga ccagcacact gagaatcaac    600
acaacaacta atgagatttt ctactgcact tttaggagat tagatcctga ggaaaaccat    660
acagctgaat tggtcatccc agaactacct ctggcacatc ctccaaatga aaggactcac    720
ttggtaattc tgggagccat cttattatgc cttggtgtag cactgacatt catcttccgt    780
ttaagaaaag ggagaatgat ggatgtgaaa aatgtggca tccaagatac aaactcaaag    840
aagcaaagtg atacacattt ggaggagacg                                     870
```

<210> SEQ ID NO 2
<211> LENGTH: 290
<212> TYPE: PRT
<213> ORGANISM: Homo sapiens

<400> SEQUENCE: 2

```
Met Arg Ile Phe Ala Val Phe Ile Phe Met Thr Tyr Trp His Leu Leu
1               5                  10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290
```

<210> SEQ ID NO 3

<211> LENGTH: 717
<212> TYPE: DNA
<213> ORGANISM: Homo sapiens

<400> SEQUENCE: 3

```
atgaggatat ttgctgtctt tatattcatg acctactggc atttgctgaa cgcatttact      60
gtcacggttc ccaaggacct atatgtggta gagtatggta gcaatatgac aattgaatgc     120
aaattcccag tagaaaaaca attagacctg gctgcactaa ttgtctattg ggaaatggag     180
gataagaaca ttattcaatt tgtgcatgga gaggaagacc tgaaggttca gcatagtagc     240
tacagacaga gggcccggct gttgaaggac cagctctccc tgggaaatgc tgcacttcag     300
atcacagatg tgaaattgca ggatgcaggg gtgtaccgct gcatgatcag ctatggtggt     360
gccgactaca gcgaattac tgtgaaagtc aatgccccat acaacaaaat caaccaaaga     420
attttggttg tggatccagt cacctctgaa catgaactga catgtcaggc tgagggctac     480
cccaaggccg aagtcatctg gacaagcagt gaccatcaag tcctgagtgg taagaccacc     540
accaccaatt ccaagagaga ggagaagctt ttcaatgtga ccagcacact gagaatcaac     600
acaacaacta atgagatttt ctactgcact tttaggagat tagatcctga ggaaaaccat     660
acagctgaat tggtcatccc agaactacct ctggcacatc ctccaaatga aaggact      717
```

<210> SEQ ID NO 4
<211> LENGTH: 239
<212> TYPE: PRT
<213> ORGANISM: Homo sapiens

<400> SEQUENCE: 4

```
Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220
```

Val Ile Pro Glu Leu Pro Leu Ala His Pro Pro Asn Glu Arg Thr
225                 230                 235

<210> SEQ ID NO 5
<211> LENGTH: 351
<212> TYPE: DNA
<213> ORGANISM: Mus musculus

<400> SEQUENCE: 5
caggtgcagc tgaaggagtc aggacctggc ctggtggcgc cctcacagag cctgtccatc      60
acttgcactg tctctggctt ttctttaacc agctatggtg tacactgggt tcgccagcct     120
ccaggaaagg gtctggagtg gctgggagta atatgggctg gtggaagtac aaattataat     180
tcggctctca tgtccagact gagcatcagt aaagacaact ccaagagcca agttgtctta     240
aaaatgaaca gtctgcaaac tgatgacaca gccatgtact actgtgccaa accatatggt     300
aattctgcta tggactactg gggtcaagga acctcagtca ccgtctcctc c              351

<210> SEQ ID NO 6
<211> LENGTH: 117
<212> TYPE: PRT
<213> ORGANISM: Mus musculus

<400> SEQUENCE: 6

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Gln Pro Pro Gly Lys Gly Leu Glu Trp Leu
        35                  40                  45

Gly Val Ile Trp Ala Gly Gly Ser Thr Asn Tyr Asn Ser Ala Leu Met
    50                  55                  60

Ser Arg Leu Ser Ile Ser Lys Asp Asn Ser Lys Ser Gln Val Val Leu
65                  70                  75                  80

Lys Met Asn Ser Leu Gln Thr Asp Asp Thr Ala Met Tyr Tyr Cys Ala
                85                  90                  95

Lys Pro Tyr Gly Asn Ser Ala Met Asp Tyr Trp Gly Gln Gly Thr Ser
            100                 105                 110

Val Thr Val Ser Ser
        115

<210> SEQ ID NO 7
<211> LENGTH: 324
<212> TYPE: DNA
<213> ORGANISM: Mus musculus

<400> SEQUENCE: 7
gacattctga tgacccagtc tcacaaattc atgtccacat cagtaggaga cacggtcagc      60
atcacctgca aggccagtca ggatgtgggt attgttgtag cctggtatca acagaaacca     120
ggccaatctc ctaaactact gatttactgg gcatctatcc ggcacactgg agtccctgat     180
cgcttcacag gcagtggatc tgggacagat ttcactctca ccattagcaa tgtgcagtct     240
gaagacttgg cagattattt ctgtcagcaa tatagcaact atcctctgta cacgttcgga     300
ggggggacca agctggaaat aaaa                                            324

<210> SEQ ID NO 8
<211> LENGTH: 108

```
<212> TYPE: PRT
<213> ORGANISM: Mus musculus

<400> SEQUENCE: 8

Asp Ile Leu Met Thr Gln Ser His Lys Phe Met Ser Thr Ser Val Gly
1               5                   10                  15

Asp Thr Val Ser Ile Thr Cys Lys Ala Ser Gln Asp Val Gly Ile Val
            20                  25                  30

Val Ala Trp Tyr Gln Gln Lys Pro Gly Gln Ser Pro Lys Leu Leu Ile
        35                  40                  45

Tyr Trp Ala Ser Ile Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Asn Tyr Pro Leu
                85                  90                  95

Tyr Thr Phe Gly Gly Gly Thr Lys Leu Glu Ile Lys
            100                 105

<210> SEQ ID NO 9
<211> LENGTH: 10
<212> TYPE: PRT
<213> ORGANISM: Mus musculus

<400> SEQUENCE: 9

Gly Phe Ser Leu Thr Ser Tyr Gly Val His
1               5                   10

<210> SEQ ID NO 10
<211> LENGTH: 16
<212> TYPE: PRT
<213> ORGANISM: Mus musculus

<400> SEQUENCE: 10

Val Ile Trp Ala Gly Gly Ser Thr Asn Tyr Asn Ser Ala Leu Met Ser
1               5                   10                  15

<210> SEQ ID NO 11
<211> LENGTH: 11
<212> TYPE: PRT
<213> ORGANISM: Mus musculus

<400> SEQUENCE: 11

Ala Lys Pro Tyr Gly Asn Ser Ala Met Asp Tyr
1               5                   10

<210> SEQ ID NO 12
<211> LENGTH: 11
<212> TYPE: PRT
<213> ORGANISM: Mus musculus

<400> SEQUENCE: 12

Lys Ala Ser Gln Asp Val Gly Ile Val Val Ala
1               5                   10

<210> SEQ ID NO 13
<211> LENGTH: 7
<212> TYPE: PRT
<213> ORGANISM: Mus musculus

<400> SEQUENCE: 13

Trp Ala Ser Ile Arg His Thr
```

<210> SEQ ID NO 14
<211> LENGTH: 10
<212> TYPE: PRT
<213> ORGANISM: Mus musculus

<400> SEQUENCE: 14

Gln Gln Tyr Ser Asn Tyr Pro Leu Tyr Thr
1               5                   10

<210> SEQ ID NO 15
<211> LENGTH: 117
<212> TYPE: PRT
<213> ORGANISM: Artificial Sequence
<220> FEATURE:
<223> OTHER INFORMATION: hu333-1A pro-vh

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Thr Ser Tyr
            20                  25                  30

Gly Val His Trp Val Arg Gln Ala Pro Gly Lys Gly Leu Glu Trp Val
        35                  40                  45

Ala Val Ile Trp Ala Gly Gly Ser Thr Asn Tyr Asn Ser Ala Leu Met
    50                  55                  60

Ser Arg Leu Thr Ile Ser Lys Asp Asn Ala Lys Asn Ser Val Tyr Leu
65                  70                  75                  80

Gln Met Asn Ser Leu Arg Ala Glu Asp Thr Ala Val Tyr Tyr Cys Ala
                85                  90                  95

Lys Pro Tyr Gly Asn Ser Ala Met Asp Tyr Trp Gly Gln Gly Thr Leu
            100                 105                 110

Val Thr Val Ser Ser
        115

<210> SEQ ID NO 16
<211> LENGTH: 108
<212> TYPE: PRT
<213> ORGANISM: Artificial Sequence
<220> FEATURE:
<223> OTHER INFORMATION: hu333-1A pro-vk

<400> SEQUENCE: 16

Asp Ile Gln Met Thr Gln Ser Pro Ser Thr Leu Ser Ala Ser Val Gly
1               5                   10                  15

Asp Arg Val Thr Ile Thr Cys Lys Ala Ser Gln Asp Val Gly Ile Val
            20                  25                  30

Val Ala Trp Tyr Gln Gln Lys Pro Gly Lys Ala Pro Lys Leu Leu Ile
        35                  40                  45

Tyr Trp Ala Ser Ile Arg His Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ser Asn Tyr Pro Leu
                85                  90                  95

Tyr Thr Phe Gly Gln Gly Thr Lys Leu Glu Ile Lys
            100                 105

```
<210> SEQ ID NO 17
<211> LENGTH: 117
<212> TYPE: PRT
<213> ORGANISM: Artificial Sequence
<220> FEATURE:
<223> OTHER INFORMATION: hu333-2B pro-vh

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Thr Ser Tyr
            20                  25                  30

Gly Val His Trp Val Arg Gln Ala Pro Gly Lys Gly Leu Glu Trp Val
        35                  40                  45

Ala Val Ile Trp Ala Gly Gly Ser Thr Asn Tyr Val Asp Ser Val Lys
    50                  55                  60

Gly Arg Phe Thr Ile Ser Lys Asp Asn Ala Lys Asn Ser Val Tyr Leu
65                  70                  75                  80

Gln Met Asn Ser Leu Arg Ala Glu Asp Thr Ala Val Tyr Tyr Cys Ala
                85                  90                  95

Lys Pro Tyr Gly Asn Ser Ala Met Asp Tyr Trp Gly Gln Gly Thr Leu
            100                 105                 110

Val Thr Val Ser Ser
        115

<210> SEQ ID NO 18
<211> LENGTH: 117
<212> TYPE: PRT
<213> ORGANISM: Artificial Sequence
<220> FEATURE:
<223> OTHER INFORMATION: hu333-3A2 pro-vh

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Thr Ser Tyr
            20                  25                  30

Gly Val His Trp Val Arg Gln Ala Pro Gly Lys Gly Leu Glu Trp Val
        35                  40                  45

Ala Val Ile Trp Ala Gly Gly Ser Thr Asn Tyr Val Asp Ser Val Lys
    50                  55                  60

Gly Arg Leu Thr Ile Ser Lys Asp Asn Ala Lys Asn Thr Val Tyr Leu
65                  70                  75                  80

Gln Met Asn Ser Leu Arg Ala Glu Asp Thr Ala Val Tyr Tyr Cys Ala
                85                  90                  95

Lys Pro Tyr Gly Asn Ser Ala Met Asp Tyr Trp Gly Gln Gly Thr Leu
            100                 105                 110

Val Thr Val Ser Ser
        115

<210> SEQ ID NO 19
<211> LENGTH: 117
<212> TYPE: PRT
<213> ORGANISM: Artificial Sequence
<220> FEATURE:
<223> OTHER INFORMATION: hu333-3C2 pro-vh

<400> SEQUENCE: 19

Glu Val Gln Leu Val Glu Ser Gly Gly Gly Leu Val Gln Pro Gly Gly
1               5                   10                  15
```

-continued

Ser Leu Arg Leu Ser Cys Ala Val Ser Gly Phe Ser Leu Thr Ser Tyr
            20                  25                  30

Gly Val His Trp Val Arg Gln Ala Pro Gly Lys Gly Leu Glu Trp Val
        35                  40                  45

Ala Val Ile Trp Ala Gly Gly Ser Thr Asn Tyr Ala Asp Ser Val Lys
    50                  55                  60

Gly Arg Phe Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Lys Pro Tyr Gly Asn Ser Ala Met Asp Tyr Trp Gly Gln Gly Thr Leu
            100                 105                 110

Val Thr Val Ser Ser
        115

<210> SEQ ID NO 20
<211> LENGTH: 117
<212> TYPE: PRT
<213> ORGANISM: Artificial Sequence
<220> FEATURE:
<223> OTHER INFORMATION: hu333-3H2 pro-vh

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Thr Ser Tyr
            20                  25                  30

Gly Val His Trp Val Arg Gln Ala Pro Gly Lys Gly Leu Glu Trp Val
        35                  40                  45

Ala Val Ile Trp Ala Gly Gly Ser Thr Asn Tyr Ala Asp Ser Val Lys
    50                  55                  60

Gly Arg Phe Thr Ile Ser Lys Asp Thr Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Lys Pro Tyr Gly Asn Ser Ala Met Asp Tyr Trp Gly Gln Gly Thr Leu
            100                 105                 110

Val Thr Val Ser Ser
        115

<210> SEQ ID NO 21
<211> LENGTH: 117
<212> TYPE: PRT
<213> ORGANISM: Artificial Sequence
<220> FEATURE:
<223> OTHER INFORMATION: hu333-4A2 pro-vh

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Thr Ser Tyr
            20                  25                  30

Gly Val His Trp Val Arg Gln Ala Pro Gly Lys Gly Leu Glu Trp Val
        35                  40                  45

Ala Val Ile Trp Ala Gly Gly Ser Thr Asn Tyr Val Asp Ser Val Lys
    50                  55                  60

Gly Arg Phe Thr Ile Ser Lys Asp Asn Ala Lys Asn Thr Val Tyr Leu

```
              65                  70                  75                  80
Gln Met Asn Ser Leu Arg Ala Glu Asp Thr Ala Val Tyr Tyr Cys Ala
                    85                  90                  95

Lys Pro Tyr Gly Thr Ser Ala Met Asp Tyr Trp Gly Gln Gly Thr Leu
               100                 105                 110

Val Thr Val Ser Ser
            115

<210> SEQ ID NO 22
<211> LENGTH: 117
<212> TYPE: PRT
<213> ORGANISM: Artificial Sequence
<220> FEATURE:
<223> OTHER INFORMATION: hu333-4B2 pro-vh

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Thr Ser Tyr
            20                  25                  30

Gly Val His Trp Val Arg Gln Ala Pro Gly Lys Gly Leu Glu Trp Val
        35                  40                  45

Ala Val Ile Trp Ala Gly Gly Ser Thr Asn Tyr Ala Asp Ser Val Lys
    50                  55                  60

Gly Arg Phe Thr Ile Ser Lys Asp Thr Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Lys Pro Tyr Gly Thr Ser Ala Met Asp Tyr Trp Gly Gln Gly Thr Leu
               100                 105                 110

Val Thr Val Ser Ser
            115

<210> SEQ ID NO 23
<211> LENGTH: 108
<212> TYPE: PRT
<213> ORGANISM: Artificial Sequence
<220> FEATURE:
<223> OTHER INFORMATION: hu333-4B2 pro-vk

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Ile Val
            20                  25                  30

Val Ala Trp Tyr Gln Gln Lys Pro Gly Lys Ala Pro Lys Leu Leu Ile
        35                  40                  45

Tyr Trp Ala Ser Ile Arg His Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ser Asn Tyr Pro Leu
                85                  90                  95

Tyr Thr Phe Gly Gln Gly Thr Lys Val Glu Ile Lys
               100                 105

<210> SEQ ID NO 24
<211> LENGTH: 16
```

```
<212> TYPE: PRT
<213> ORGANISM: Artificial Sequence
<220> FEATURE:
<223> OTHER INFORMATION: hu333-4A2 H-CDR2

<400> SEQUENCE: 24

Val Ile Trp Ala Gly Gly Ser Thr Asn Tyr Val Asp Ser Val Lys Gly
 1               5                  10                  15

<210> SEQ ID NO 25
<211> LENGTH: 16
<212> TYPE: PRT
<213> ORGANISM: Artificial Sequence
<220> FEATURE:
<223> OTHER INFORMATION: hu333-4B2 HCDR2

<400> SEQUENCE: 25

Val Ile Trp Ala Gly Gly Ser Thr Asn Tyr Ala Asp Ser Val Lys Gly
 1               5                  10                  15

<210> SEQ ID NO 26
<211> LENGTH: 11
<212> TYPE: PRT
<213> ORGANISM: Artificial Sequence
<220> FEATURE:
<223> OTHER INFORMATION: hu333-4B2 H-CDR3

<400> SEQUENCE: 26

Ala Lys Pro Tyr Gly Thr Ser Ala Met Asp Tyr
 1               5                  10

<210> SEQ ID NO 27
<211> LENGTH: 330
<212> TYPE: PRT
<213> ORGANISM: Homo sapiens

<400> SEQUENCE: 27

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190
```

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 28
<211> LENGTH: 329
<212> TYPE: PRT
<213> ORGANISM: Artificial Sequence
<220> FEATURE:
<223> OTHER INFORMATION: huIgG1mc pro

<400> SEQUENCE: 28

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Pro Ala Ala Ala Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Ala Ala Pro Ile Glu Lys Thr Ile Ser Lys Ala Lys Gly Gln
    210                 215                 220

| | | | | | | | | | | | |
|---|---|---|---|---|---|---|---|---|---|---|---|
| Pro | Arg | Glu | Pro | Gln | Val | Tyr | Thr | Leu | Pro | Pro | Ser | Arg | Asp | Glu | Leu |
| 225 | | | | 230 | | | | | 235 | | | | | | 240 |

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 29
<211> LENGTH: 329
<212> TYPE: PRT
<213> ORGANISM: Artificial Sequence
<220> FEATURE:
<223> OTHER INFORMATION: huIgG1mf pro

<400> SEQUENCE: 29

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Pro Ala Ala Gly Pro Ser Val Phe Leu Phe Pro Pro Lys
        115                 120                 125

Pro Lys Asp Thr Leu Met Ile Ser Arg Thr Pro Glu Val Thr Cys Val
130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Ala Ala Pro Ile Glu Lys Thr Ile Ser Lys Ala Lys Gly Gln
    210                 215                 220

Pro Arg Glu Pro Gln Val Tyr Thr Leu Pro Pro Ser Arg Asp Glu Leu
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 30
<211> LENGTH: 446
<212> TYPE: PRT
<213> ORGANISM: Artificial Sequence
<220> FEATURE:
<223> OTHER INFORMATION: hu333-4A2-IgG1mc HC pro

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Thr Ser Tyr
            20                  25                  30

Gly Val His Trp Val Arg Gln Ala Pro Gly Lys Gly Leu Glu Trp Val
        35                  40                  45

Ala Val Ile Trp Ala Gly Gly Ser Thr Asn Tyr Val Asp Ser Val Lys
    50                  55                  60

Gly Arg Phe Thr Ile Ser Lys Asp Asn Ala Lys Asn Thr Val Tyr Leu
65                  70                  75                  80

Gln Met Asn Ser Leu Arg Ala Glu Asp Thr Ala Val Tyr Tyr Cys Ala
                85                  90                  95

Lys Pro Tyr Gly Thr Ser Ala Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Ala Ala Ala Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

```
Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Ala Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 31
<211> LENGTH: 446
<212> TYPE: PRT
<213> ORGANISM: Artificial Sequence
<220> FEATURE:
<223> OTHER INFORMATION: hu333-4B2-IgG1mc HC pro

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Thr Ser Tyr
            20                  25                  30

Gly Val His Trp Val Arg Gln Ala Pro Gly Lys Gly Leu Glu Trp Val
        35                  40                  45

Ala Val Ile Trp Ala Gly Gly Ser Thr Asn Tyr Ala Asp Ser Val Lys
    50                  55                  60

Gly Arg Phe Thr Ile Ser Lys Asp Thr Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Lys Pro Tyr Gly Thr Ser Ala Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205
```

```
Thr Lys Val Asp Lys Lys Val Glu Pro Lys Ser Cys Asp Lys Thr His
    210                 215                 220
Thr Cys Pro Pro Cys Pro Ala Pro Pro Ala Ala Ala Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser His Glu Asp Pro Glu Val
            260                 265                 270
Lys Phe Asn Trp Tyr Val Asp Gly Val Glu Val His Asn Ala Lys Thr
        275                 280                 285
Lys Pro Arg Glu Glu Gln Tyr Asn Ser Thr Tyr Arg Val Val Ser Val
290                 295                 300
Leu Thr Val Leu His Gln Asp Trp Leu Asn Gly Lys Glu Tyr Lys Cys
305                 310                 315                 320
Lys Val Ser Asn Lys Ala Leu Ala Ala Pro Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Arg Asp Glu Leu Thr Lys Asn Gln Val Ser Leu Thr Cys Leu Val
        355                 360                 365
Lys Gly Phe Tyr Pro Ser Asp Ile Ala Val Glu Trp Glu Ser Asn Gly
    370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro Gly Lys
        435                 440                 445

<210> SEQ ID NO 32
<211> LENGTH: 215
<212> TYPE: PRT
<213> ORGANISM: Artificial Sequence
<220> FEATURE:
<223> OTHER INFORMATION: hu333-4B2-IgG1mf LC pro

<400> SEQUENCE: 32

Asp Ile Gln Met Thr Gln Ser Pro Ser Ser Leu Ser Ala Ser Val Gly
1               5                   10                  15
Asp Arg Val Thr Ile Thr Cys Lys Ala Ser Gln Asp Val Gly Ile Val
            20                  25                  30
Val Ala Trp Tyr Gln Gln Lys Pro Gly Lys Ala Pro Lys Leu Leu Ile
        35                  40                  45
Tyr Trp Ala Ser Ile Arg His Thr Gly Val Pro Ser Arg Phe Ser Gly
    50                  55                  60
Ser Gly Ser Gly Thr Glu Phe Thr Leu Thr Ile Ser Ser Leu Gln Pro
65                  70                  75                  80
Asp Asp Phe Ala Thr Tyr Tyr Cys Gln Gln Tyr Ser Asn Tyr Pro Leu
                85                  90                  95
Tyr Thr Phe Gly Gln Gly Thr Lys Val Glu Ile Lys Arg Thr Val Ala
            100                 105                 110
Ala Pro Ser Val Phe Ile Phe Pro Pro Ser Asp Glu Gln Leu Lys Ser
        115                 120                 125
```

```
Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 33
<211> LENGTH: 446
<212> TYPE: PRT
<213> ORGANISM: Artificial Sequence
<220> FEATURE:
<223> OTHER INFORMATION: hu333-4B2-IgG1mf HC pro

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Thr Ser Tyr
            20                  25                  30

Gly Val His Trp Val Arg Gln Ala Pro Gly Lys Gly Leu Glu Trp Val
        35                  40                  45

Ala Val Ile Trp Ala Gly Gly Ser Thr Asn Tyr Ala Asp Ser Val Lys
    50                  55                  60

Gly Arg Phe Thr Ile Ser Lys Asp Thr Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Lys Pro Tyr Gly Thr Ser Ala Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Pro Ala Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270
```

-continued

```
Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Ala Ala Pro Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445
```